(12) United States Patent
van Gorcom et al.

(10) Patent No.: US 6,586,209 B1
(45) Date of Patent: Jul. 1, 2003

(54) XYLANASE PRODUCTION

(75) Inventors: Robert F. M. van Gorcom, Delft (NL); Johanna G. M. Hessing, Delft (NL); Jan Maat, Monster (NL); Martinus Roza, Strijen (NL); Johannes Maria A. Verbakel, Maasland (NL)

(73) Assignee: Quest International, B.V., Naarden (NL)

( * ) Notice: Subject to any disclaimer, the term of this patent is extended or adjusted under 35 U.S.C. 154(b) by 0 days.

(21) Appl. No.: 07/955,726

(22) PCT Filed: Jun. 18, 1991

(86) PCT No.: PCT/EP91/01135

§ 371 (c)(1), (2), (4) Date: Feb. 18, 1993

(87) PCT Pub. No.: WO91/19782

PCT Pub. Date: Dec. 26, 1991

(30) Foreign Application Priority Data

Jun. 19, 1990 (NL) ............................................ 9001388

(51) Int. Cl.⁷ .......................... C12N 15/09; C12N 9/30; C12N 9/42; C12N 1/22

(52) U.S. Cl. ...................... 435/69.2; 435/69.1; 435/203; 435/209; 435/252.3; 435/325; 536/23.74; 536/23.2; 530/324; 426/549; 426/592; 426/660; 426/656; 426/496

(58) Field of Search .............................. 536/23.2, 23.74; 435/69.1, 201, 203, 252.3, 252.31, 254.2, 254.3, 254.6, 254.23, 254.21, 209, 69.2, 325; 426/549, 656, 496, 660, 592; 530/324

(56) References Cited

U.S. PATENT DOCUMENTS

| | | | | |
|---|---|---|---|---|
| 4,725,544 A | * | 2/1988 | Tan et al. ................... | 435/209 |
| 4,894,338 A | * | 1/1990 | Knowles et al. ............ | 435/209 |
| 4,966,850 A | * | 10/1990 | Yu et al. ...................... | 435/209 |
| 5,024,941 A | * | 6/1991 | Maine et al. ................ | 435/203 |
| 5,108,765 A | * | 4/1992 | Maat et al. .................. | 426/549 |
| 5,238,833 A | * | 8/1993 | Sanders et al. ............. | 435/69.1 |
| 5,252,726 A | * | 10/1993 | Wöldike ...................... | 435/203 |
| 5,358,864 A | * | 10/1994 | van den Broeck .......... | 435/209 |

FOREIGN PATENT DOCUMENTS

| | | |
|---|---|---|
| AU | 77910/91 | 11/1991 |
| AU | 78698/91 | 11/1991 |
| AU | 654147 | 2/1992 |
| AU | 647170 | 3/1994 |
| EP | 0 121 138 | 10/1984 |
| EP | 0 163 491 | 12/1985 |
| EP | 0 187 382 | 7/1986 |
| EP | 0 311 469 | 4/1989 |
| EP | 316023 | 5/1989 |
| EP | 0 338 452 | 10/1989 |
| EP | 338452 | 10/1989 |
| EP | 0 357 127 | 3/1990 |
| EP | 0 396 162 | 11/1990 |
| EP | 0463706 | 10/1996 |
| FR | 2 555 602 | 5/1985 |
| GB | 2091268 | 7/1982 |
| GB | 2 091 268 | 7/1982 |
| GB | 2 150 933 | 7/1985 |
| WO | WO 86/07091 | 12/1986 |
| WO | WO 91/17244 | 11/1991 |

OTHER PUBLICATIONS

Tavobilov et al., "Purification of Endo–1, 4–B–Xylanase from . . . A. Niger", App. Biochem. Microbiol. 17(3):320–324.*

Changas et al., "Cloning at a *Thermonospora fusca* Xylanase Gene and Its Expression . . . " J. Bacteriology 171(6):2963–2969, (Jun. 1989).*

Shamala et al., "Production of cellulases and D–xylanae by some selected fungal isolates", Enz. Microb. Technol. 8:178–182 (Mar. 1986).*

Chen et al., "B–1, 3–Xylanase and B–1,4–Xylanase Action on Rhodymenan" Agric. Biol. Chem. 50(5):1195–1200, (May 1986).*

Rodzevich et al., Prikl. Biokhim. Mikrobiol. 10(6):861–867 (1974) abstracted in Biol. Abst. 61:3471. #33645, (Mar. 1976).*

Smith et al., "Isolation of mutants of *Aspergillus awanori*. . . " World J. Microbiol. Biotech. 7(3):343–354 (May 1991).*

Watson et al., Molecular Biology of the Gene, pp. 313, Benj. Cummings Publ. Co., CA, (1987).*

John et al, Can J. Biochem., 57:125–134 (1979.

BioMed Net Journal Collection (1990).

Kuhn et al, Journal of Food Science, 53(3):889–895 (1988).

Finkelstein et al, Antonie Van Leeuwenhoek, 53(5):349–352 (1987).

Penttila et al, Curr. Genet., 12:413–420 (1987).

Panbangred et al, Mol. Gen. Genet., 192:335–341 (1983).

Fukusaki et al, FEBS Letters, 171(2):197–201 (1984).

Yang et al, Nucleic Acid Research, 16(14):7187–7217 (1988).

Genbank Accession No. X07723.

Paice et al, Arch. Microbiol., 144:201–206 (1986).

Leathers et al, Biotechnology Letters, 10(11):775–780 (1988).

Li et al, Applied & Environmental Microbiology, 60(9): 3160–3166 (1994).

Frederick et al, Carbohydrate Research, 97:87–103 (1981).

Frederick et al, Biotechnology & Bioengineering, 27:525–532 (1985).

(List continued on next page.)

Primary Examiner—Yvonne Eyler
(74) Attorney, Agent, or Firm—Fitch, Even, Tabin & Flannery

(57) ABSTRACT

An isolated DNA with a nucleotide sequence encoding a ripening form of a xylanase fungal origin having bread improving activity. Cells are transformed with this DNA and used to produce the ripening form of xylanase which itself is suitable for use in flour and dough.

41 Claims, 30 Drawing Sheets

OTHER PUBLICATIONS

Shei et al, Biotechnology & Bioengineering, 27:533–538 (1985).
Fournier et al, Biotechnology & Bioengineering, 27:539–546 (1985).
Dictionary of Microbiology & Molecular Biology, John Wiley & Sons, p. 971 (1987).
Sambrook et al, "Synthetic Oligonucleotide Probes", Molecular Cloning: A Labaoratory Manual, 2nd Ed., Cold Spring Harbor Laboratory Press, 11.2, 1987.
Wong et al, Microbiological Reviews, 52(3):305–317 (1988).
Poutanen et al, Journal of Biotechnology, 6:49–60 (1987).
Nucleic Acids Research, 16:9874–9890 (1988).
Bertrand et al, Biotechnol. Bioeng., 33:791–794 (1989).
Kitpreechavanich et al, J. Ferment. Technol., 62:63–69 (1984).
Yu et al, Enzyme Microb. Technol., 9:16–24 (1987).
Kudo et al, J. Gen. Microbiol., 131:2825–2830 (1985).
Bailey et al, Appl. Microbiol. Biotechnol., 30:5–10 (1989).
Leathers, J. Ind. Microbiol., 4:341–348 (1989).
Morosoli et al, FEMS Microbiol. Lett., 51:217–224 (1988).
Morosoli et al., Biochim. Biophys. Acta., 870:473–478 (1986).
Noe et al, Journal of Wood Chemistry & Technology, 6(2):167–184 (1986).
Ito et al, Biosci. Biotech. Biochem., 56:547–550 (1992).
Knowles, Science, 236:1252–1258 (1987).
Poutanen, Techn. Res. Cent. Finl. Publ., 47:3–59 (1988).
Kellet et al, Biochem. J., 272:369–376 (1990).
Ghanges et al, J. Bacteriol., 171(6):2963–2969 (1989).
Iwasaki et al, Journal of Antibiotics, XXXIX(7):985–993 (1986).
Kudo et al, Chemical Abstracts, 103:272 (1985).
Vats–Mehta et al, Gene, 86:119–122 (1990).
Luthi et al, Applied & Environmental Microbiology, 56(4):1017–1024 (1990).
Bernier, Jr. et al, Gene 26:59–65 (1983).
Mondou et al, Gene, 49:323–329 (1986).
McCleary, Int. J. Biol. Macromol., 8:349–354 (1986).
Boucher et al, Nucleic Acids Research, 16:9874 (1988).
Nagashima et al, Trends Actinomycetologia, 91–96 (1989).
Zappe et al, Nucleic Acids Res., 18:2179–2182 (1990).
Ostanin et al, Journal of Biological Chemistry, 270(31):18491–18499 (1995).
Amoresano et al, Glycobiology, 10:451–458 (2000).
Biotechnol. Lett., 10:755–780 (1988).
Bourbonnais et al, Arch. Microbiol., 144:201–202 (1986).
Grepinet et al, J. Bacteriol, 170:4852–4588 (1988).
Hamamoto et al, Agric. Biol. Chem., 51:953–955 (1987).
Fukumoto et al, Nippon Nogeikagakii Kaishi, 44:447–456 (1970.
Iwamoto et al, Mem. Coll. Agric. Ehime Univ., 17:185–197 (1973).
Gorbacheva et al, Biochem. Biophys. Acta, 484:79–93 (1977).
Gorbacheva et al, Biochim. Biophys. Acta, 484:94–102 (1977).
Rodionova et al, Biochemistry, 42:505–516 (1977).
Takenishi et al, Agric. Biol. Chem., 39:2315–2323 (1975).
Tavobilov et al, Appl. Biochem. Microbiol., 17:320–324 (1981).
Kluepfel et al, Biochem. J., 267:45–50 (1990).
Berenger et al, Can. J. Microbiol., 31:635–643 (1985).
Esteban et al, Can. J. Microbiol., 28:733–739 (1982).
Tan et al, Can. J. Microbiol., 33:689–692 (1987).
Sinner et al, Holzforshung, 29:168–177 (1975).
Sinner et al, Holzforshung, 29:207–214 (1975).
Sinner et al, Holzforshung, 30:50–59 (1976).
Gibson et al, Carbohydr. Polymers, 7:225–240 (1987).
Hashimoto et al, Agric. Biol. Chem., 35:501–508 (1971).
Reilly, Basic Life Sci., 18:111–129 (1981).
Tan et al, Enzyme Microb. Technol., 7:431–436 (1985).
Tan et al, Biotechnol. Bioeng., 30:96–100 (1987).
Yang, et al, Nucleic Acids Research, vol. 16, No. 14, 1988, p. 7187.
Leathers, "Amino Acid Compositio and Partial Sequence of Xylanase from Aureobasidium", Biotechnology Letters, vol. 10, No. 11, 775–780 (1988).
Paice, et al, "A Xylanase Gene from *Bacillus Subtilis*: Nucleotide Sequence and Comparison with *B.pumilus* gene", Arch Microbiol (1986) 144:201–206.
Ballance, "Sequence Important for Gene Expression in Filamentous Fungi", Yeast vol. 2: 229–236 (1986).
Fukusaki et al, "The Complete Nucleotide Sequence of the Xylanase Gene (xynA) of *Bacillus Pumilus*", FEBS Letters, vol. 171, No. 2, Jun. 1984. pp 197–201.
Panbangred, et al, "Molecular Cloning of the Genes for Xylan Degradation of *Bacillus pumilus* and Their Expression in *Escherichia coli*", Mol Gen Genet (1983) 192:335–341.
Fournier, et al, "Purification and Characterization of Endo–Xylanases from *Aspergillus niger*.III An Enzyme of pI 3.65", Biotechnology & Bioengineering, vol. XXVII, pp. 539–536 (1985).
Kuhn et al, "Influence of the Enzymatic Modification of the Nonstarchy Polysaccharide Fractions on the Baking Properties of Reconstituted Rye Flour", Journal of Food Science, vol. 53, No. 3, 1988, pp. 889–895.
Penttila et al, "Construction of Brewer's Yeasts Secreting Fungal endo–beta–glucanase", Current Genetics, vol. 12, No. 6, 1987 pp. 413–420.

* cited by examiner

FIG. 1

```
                   .         20              .        40              .         60
       ATGAAGGTCACTGCGGCTTTTGCAGGTCTTTTGGTCACGGCATTCGCCGCTCCTGTGCCG
       --------------+---------------+---------------+---------------+---------------|
        M   K   V   T   A   A   F   A   G   L   L   V   T   A   F   A   A   P   V   P
                   .         80              .       100              .        120
       GAACCTGTTCTGGTGTCGCGAAGTGCTGGTATTAACTACGTGCAAAACTACAACGGCAAC
       --------------+---------------+---------------+---------------+---------------|
        E   P   V   L   V   S   R   S   A   G   I   N   Y   V   Q   N   Y   G   N
                                       |=> mature xylanase
                   .        140              .       160              .        180
       CTTGGTGATTTCACCTATGACGAGAGTGCCGGAACATTTTCCATGTACTGGGAAGATGGA
       --------------+---------------+---------------+---------------+---------------+
        L   G   D   F   T   Y   D   E   S   A   G   T   F   S   M   Y   W   E   D   G
                   .        200              .       220              .        240
       GTGAGCTCCGACTTTGTCGTTGGTCTGGGCTGGACCACTGGTTCTTCTAAGTGAGTGACT
       --------------+---------------+---------------+---------------+---------------+
        V   S   S   D   F   V   V   G   L   G   W   T   T   G   S   S   N
                   .        260              .       280              .        300
       GTATTCTTTAACCAAAGTCTAGGATCTAACGTTTTCTAGCGCTATCACCTACTCTGCCGA
       --------------+---------------+---------------+---------------+---------------+
                                                         A   I   T   Y   S   A   E
                   .        320              .       340              .        360
       ATACAGTGCTTCTGGCTCCTCTTCCTACCTCGCTGTGTACGGCTGGGTCAACTATCCTCA
       --------------+---------------+---------------+---------------+---------------+
        Y   S   A   S   G   S   S   S   Y   L   A   V   Y   G   W   V   N   Y   P   Q
                   .        380              .       400              .        420
       GGCTGAATACTACATCGTCGAGGATTACGGTGATTACAACCCTTGCAGCTCGGCCACAAG
       --------------+---------------+---------------+---------------+---------------+
        A   E   Y   Y   I   V   E   D   Y   G   D   Y   N   P   C   S   S   A   T   S
                   .        440              .       460              .        480
       CCTTGGTACCGTGTACTCTGATGGAAGCACCTACCAAGTCTGCACCGACACTCGAACTAA
       --------------+---------------+---------------+---------------+---------------+
        L   G   T   V   Y   S   D   G   S   T   Y   Q   V   C   T   D   T   R   T   N
                   .        500              .       520              .        540
       CGAACCGTCCATCACGGGAACAAGCACGTTCACGCAGTACTTCTCCGTTCGAGAGAGCAC
       --------------+---------------+---------------+---------------+---------------+
        E   P   S   I   T   G   T   S   T   F   T   Q   Y   F   S   V   R   E   S   T
                   .        560              .       580              .        600
       GCGCACATCTGGAACGGTGACTGTTGCCAACCATTTCAACTTCTGGGCGCAGCATGGGTT
       --------------+---------------+---------------+---------------+---------------+
        R   T   S   G   T   V   T   V   A   N   H   F   N   F   W   A   Q   H   G   F
                   .        620              .       640              .        660
       CGGAAATAGCGACTTCAATTATCAGGTCATGGCAGTGGAAGCATGGAGCGGTGCTGGCAG
       --------------+---------------+---------------+---------------+---------------+
        G   N   S   D   F   N   Y   Q   V   M   A   V   E   A   W   S   G   A   G   S
                   .        680
       CGCCAGTGTCACGATCTCCTCTTAA
       --------------+---------------+---------
        A   S   V   T   I   S   S   *
```

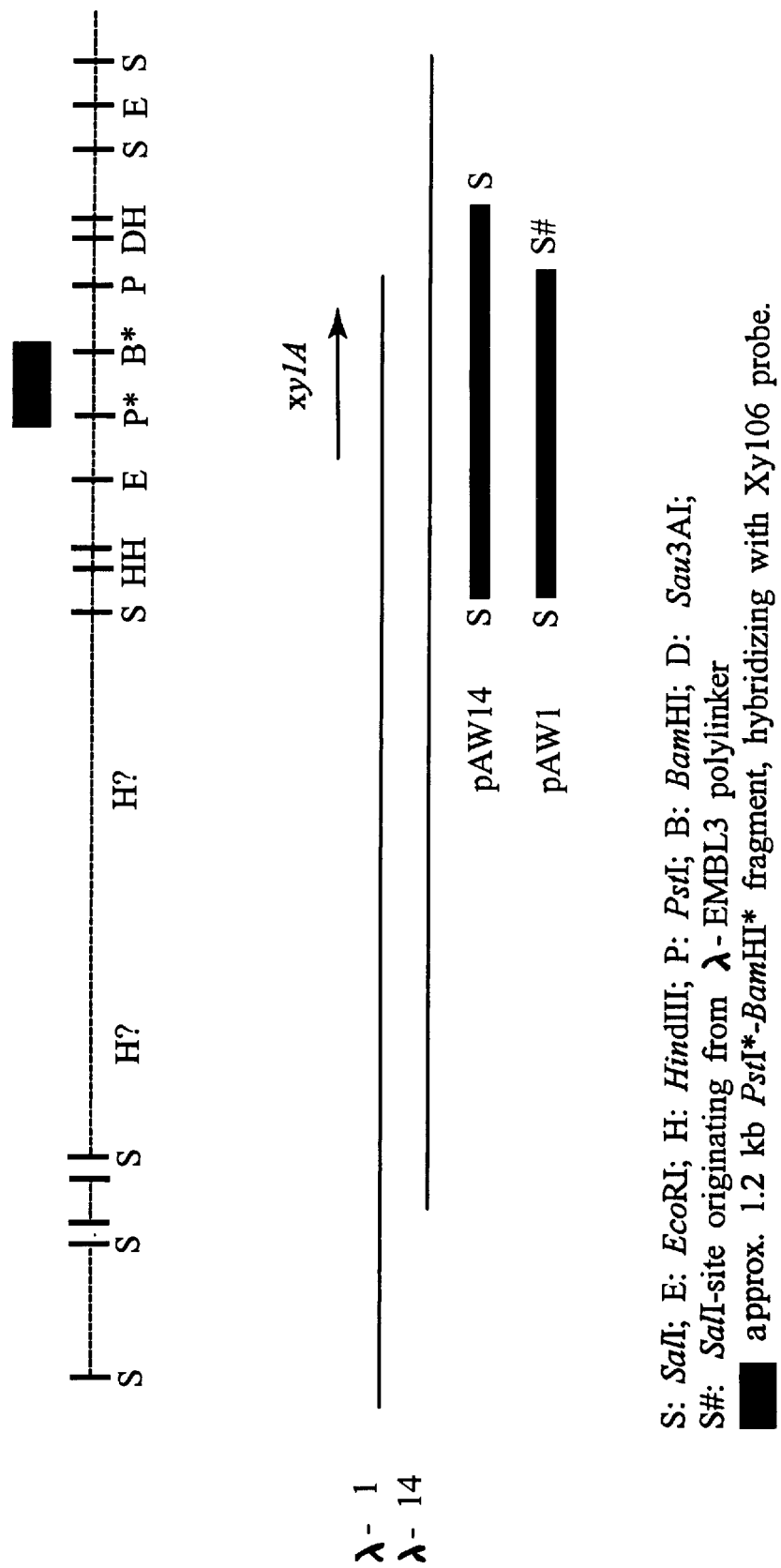

FIG. 8

```
              10         20    23   30         40         50         60
     G|AATTCCTCG AGCGACTTTG TCGTTGGTCT GGGCTGGACC ACTGGTTCT|T CTAACGCTAT
      CTTAA|GGAGC TCGCTGAAAC AGCAACCAGA C|CCGACCTGG TGACCAAGAA GATTGCGATA
                      24                                              10
      02    70         80         90         100   03    110        120
      CACCTACTCT GCCGAATACA GT|GCTTCTGG CTCCTCTTCC TACCTCGCTG TGTACGGCTG
      GTGGATG|AGA CGGCTTATGT CACGAAGACC GAGGAGAAGG ATG|GAGCGAC ACATGCCGAC
                                                         09
              130        140   04   150        160        170        180
      G|GTCAACTAT CCTCAGGCTG AATACTACAT CGTCGAGGAT TAC|GGTGATT ACAACCCTTG
      CCAGTTGATA GGAGTCCGAC TT|ATGATGTA GCAGCTCCTA ATGCCACTAA TGTTG|GGAAC
           08                                              07
         05    190        200
      CAGCTCGGCC ACAAGCCTTG GTAC|C
      GTCGAGCCGG TGTTCGGAAC|CATGG
              06
```

| code      | length | 5' <----- sequence -----> 3'                            | A  | G  | C  | T  |
|-----------|--------|---------------------------------------------------------|----|----|----|----|
| BAK 23 AM | (48)   | AAT TCC TCG AGC GAC TTT GTC GTT GGT CTG GGC TGG ACC ACT GGT TCT | 6  | 14 | 12 | 16 |
| BAK 02 JV | (33)   | TCT AAC GCT ATC ACC TAC TCT GCC GAA TAC AGT             | 9  | 4  | 11 | 9  |
| BAK 03 JV | (39)   | GCT TCT GGC TCC TCT TCC TAC CTC GCT GTG TAC GGC TGG     | 2  | 10 | 14 | 13 |
| BAK 04 JV | (42)   | GTC AAC TAT CCT CAG GCT GAA TAC TAC ATC GTC GAG GAT TAC | 12 | 8  | 11 | 11 |
| BAK 05 JV | (41)   | GGT GAT TAC AAC CCT TGC AGC TCG GCC ACA AGC TTG GTA C   | 9  | 10 | 13 | 9  |
| BAK 24 AM | (26)   | CAG ACC AAC GAC AAA GTC GCT CGA GG                      | 9  | 7  | 8  | 2  |
| BAK 10 JV | (36)   | GTA GGT GAT AGC GTT AGA AGA ACC AGT GGT CCA GCC         | 10 | 12 | 7  | 7  |
| BAK 09 JV | (36)   | GTA GGA AGA GGA GCC AGA AGC ACT GTA TTC GGC AGA         | 12 | 13 | 6  | 5  |
| BAK 08 JV | (39)   | TTC AGC CTG AGG ATA GTT GAC CCA GCC GTA CAC AGC GAG     | 10 | 11 | 11 | 7  |
| BAK 07 JV | (33)   | GTT GTA ATC ACC GTA ATC CTC GAC GAT GTA GTA             | 9  | 7  | 7  | 10 |
| BAK 06 JV | (25)   | CAA GGC TTG TGG CCG AGC TGC AAG G                       | 5  | 10 | 6  | 4  |

FIG. 10

```
          10         20    25    30          40          50          60
GAATTCGAGC TCATCACACA AACAAACAAA ACAAAATGAT GCTTTTGCAA GCCTTCCTTT
CTTAAGCTCG AGTAGTGTGT TTGTTTGTTT TGTTTTACTA CGAAAACGTT CGGAAGGAAA
                            28                                   21

70    13    80          90         100         110    14   120
TCCTTTTGGC TGGTTTTGCA GCCAAAATAT CTGCGAGTGC TGGTATTAAC TACGTGCAAA
AGGAAAACCG ACCAAAACGT CGGTTTTATA GACGCTCACG ACCATAATTG ATGCACGTTT
                                 20

130         140    15   150         160         170         180
ACTACAACGG CAACCTTGGT GATTTCACCT ATGACGAGAG TGCCGGAACA TTTTCCATGT
TGATGTTGCC GTTGGAACCA CTAAAGTGGA TACTGCTCTC ACGGCCTTGT AAAAGGTACA
 19                                                18

26       190         200
ACTGGGAAGA TGGAGTCTCG AG
TGACCCTTCT ACCTCAGAGC TC
        27
```

| code | length | 5' <----- sequence -----> 3' | A | G | C | T |
|---|---|---|---|---|---|---|
| BAK 25 AM | (52) | AAT TCG AGC TCA TCA CAC AAA CAA ACA AAA CAA AAT GAT GCT TTT GCA AGC C | 23 | 6 | 13 | 10 |
| BAK 13 JV | (36) | TTC CTT TTC CTT TTG GCT GGT TTT GCA GCC AAA ATA | 6 | 6 | 8 | 16 |
| BAK 14 JV | (36) | TCT GCG AGT GCT GGT ATT AAC TAC GTG CAA AAC TAC | 10 | 8 | 8 | 10 |
| BAK 15 JV | (36) | AAC GGC AAC CTT GGT GAT TTC ACC TAT GAC GAG AGT | 10 | 9 | 8 | 9 |
| BAK 26 AM | (36) | GCC GGA ACA TTT TCC ATG TAC TGG GAA GAT GGA GTC | 9 | 11 | 7 | 9 |
| BAK 28 AM | (33) | CAT TTT GTT TTG TTT GTT TGT GTG ATG AGC TCG | 3 | 9 | 3 | 18 |
| BAK 21 JV | (33) | AGC CAA AAG GAA AAG GAA GGC TTG CAA AAG CAT | 16 | 9 | 5 | 3 |
| BAK 20 JV | (36) | AAT ACC AGC ACT CGC AGA TAT TTT GGC TGC AAA ACC | 12 | 6 | 10 | 8 |
| BAK 19 JV | (33) | ACC AAG GTT GCC GTT GTA GTT TGC ACG TAG TT | 6 | 9 | 6 | 12 |
| BAK 18 JV | (36) | GGA AAA TGT TCC GGC ACT CTC GTC ATA GGT GAA ATC | 10 | 9 | 8 | 9 |
| BAK 27 AM | (25) | TCG AGA CTC CAT CTT CCC AGT ACA T | 6 | 3 | 9 | 7 |

FIG. 15

```
         10         20   42    30         40              50      15   60
GAATTCGCCG CGGGTATTAA CTACGTGCAA AACTACAACG GCAACCTTGG TGATTTCACC
CTTAAGCGGC GCCCATAATT GATGCACGTT TTGATGTTGC CGTTGGAACC ACTAAAGTGG
                          41
         70         80         90    26   100             110
TATGACGAGA GTGCCGGAAC ATTTTCCATG TACTGGGAAG ATGGAGTGTC GAG
ATACTGCTCT CACGGCCTTG TAAAAGGTAC ATGACCCTTC TACCTCAGAG CTC
    18                                         27
```

| code | length | 5' <----- sequence -----> 3' | A | G | C | T |
|---|---|---|---|---|---|---|
| BAK 42 | (34) | AAT TCG CCG CGG GTA TTA ACT ACG TGC AAA ACT A | 11 | 7 | 8 | 8 |
| BAK 15 | (37) | CAA CGG CAA CCT TGG TGA TTT CAC CTA TGA CGA GAG T | 10 | 9 | 9 | 9 |
| BAK 26 | (36) | GCC GGA ACA TTT TCC ATG TAC TGG GAA GAT GGA GTC | 9 | 11 | 7 | 9 |
| BAK 41 | (46) | ACC AAG GTT GCC GTT GTA GTT TTG CAC GTA GTT AAT ACC CGC GGC G | 9 | 13 | 11 | 13 |
| BAK 18 | (36) | GGA AAA TGT TCC GGC ACT CTC GTC ATA GGT GAA ATC | 10 | 9 | 8 | 9 |
| BAK 27 | (25) | TCG AGA CTC CAT CTT CCC AGT ACA T | 6 | 3 | 9 | 7 |

FIG. 18

```
         EcoRI   BglII                                                                                                  .                   90
  1  GGAATTCAGATCTTGAATTGATGTTACCCTCATAAAGCACGTGGCCTCTTATCGAGAAAGAAATTACCGTCGCTCGTGATTGTTGCAA
     CCTTAAGTCTAGAACTTAACTACAATGGGAGTATTTCGTGCACCGGAGAATAGCTCTTTCTTTAATGGCAGCGAGCACTAAACAACGTT

.                  180
 91  AAAGAACAAAACTGAAAAAACCAGACACGCTCGACTTCCTGTCTTCCTATTGATTGCAGCTTCCAATTCGTCACACAACAAGGTCCTA
     TTTCTTGTTTTGACTTTTTTGGTCTGTGCGAGCTGAAGGACAGAAGGATAACTAACGTCGAAGGTTAAGCAGTGTGTGTTCCAGGAT

.                  270
181  GCGACGGCTCACAGGTTTGTAACAAGCAATGCAAGGTTCTGAATGGCGGGAAAGGGTTTAGTACCACATGCTATGATGCCACTGTGA
     CGCTGCCGAGTGTCCAAACATTGTTCGTTAGCTTCCAAGACCTTACCGCCCTTTCCAAATCATGGTACGATACTACGGTGACACT

.                  360
271  TCTCCAGAGCAAAGTTCGTTCGATCGTACTGTTACTCTCTCTCTTCAAACAGAATTGTCCGAATGTGTGACAACACAGCCTGTTCTC
     AGAGGTCTCGTTTCAAGCAAGCTAGCATGACAATGAGAGAGAAAGTTGTCTTAACAGGCTTAGCACACTGTTGTGTCGACAAGAG

.                  450
361  ACACACTCTTTTCTTCTAACCAAGGGGGTGGTTTAGTAGAACCTCGTGAAACTTACATTACATATATAAACTTGCATAAATT
     TGTGTGAGAAAGAAGAGATTGGTCCCCACCAAATCATCTTGGAGCACTTGAATGTATATATATATTTGAACGTATTTAA

.                  540
451  GGTCAATGCAAGAAATACATATTTGGTCTTTTCTAATTCGTAGTTTTCAAGTTTTCAGATGCTTTCTTTTTCTTTTTTACAGATCAT
     CCAGTTACGTTCGTTCTTATGTATAAACCAGAAAAGATTAAGCATCAAAAAGTTCAAGAATCTACGAAAAGAGAAAAATGTCTAGTA

HindIII
                                                                                                                        .
541  CAAGGAAGTAATTATCTACTTTTTACAACAAATATAAACAATGCGCAGCAGGTAAGCTTGGG  603
     GTTCCTTCATTAATAGATGAAAAATGTTGTTTATATTTGTTACGCGTCGTCCATTCGAACCC
                                                         BspMI
```

FIG. 20

```
         10         20         30         40         50    51     60
GAATTCGAGC TCATCACACA AACAAACAAA ACAAAATGAT GCTTTTGCAA GCCTTCCTTT
CTTAAGCTCG AGTAGTGTGT TTGTTTGTTT TGTTTTACTA CGAAAACGTT CGGAAGGAAA
                                                         21

70         80         90        100        110    14    120
TCCTTTTGGC TGGTTTTGCA GCCAAAATAT CTGCGTAGTGC TGGTATTAAC TACGTGCAAA
AGGAAAACCG ACCAAAACGT CGGTTTTATA GACGCTCACTG ACCATAATTG ATGCACGTTT
                                  20

130        140   15   150        160        170         180
ACTACAACGG CAACCTTGGT GATTTCACCT ATGACGAGAG TGCCGGAACA TTTTCCATGT
TGATGTTGCC GTTGGAACCA CTAAAGTGGA TACTGCTCTC ACGGCCTTGT AAAAGGTACA
 19                                        18

52       190        200
ACTGGGAAGA TGGAGTCTCG AGAAGCTT
TGACCCTTCT ACCTCAGAGC TCTTCGAA
         53
```

| code | length | 5' <----- sequence -----> 3' | A | G | C | T |
|---|---|---|---|---|---|---|
| BAK 51 AM | (55) | AAT GAT GCT TTT GCA AGC CTT CCT TTT CCT TTT GGC TGG TTT TGC AGC CAA AAT A | 11 | 10 | 12 | 22 |
| BAK 14 AM | (36) | TCT GCG AGT GCT GGT ATT AAC TAC GTG CAA AAC TAC | 10 | 8 | 8 | 10 |
| BAK 15 AM | (36) | AAC GGC AAC CTT GGT GAT TTC ACC TAT GAC GAG AGT | 10 | 9 | 8 | 9 |
| BAK 52 AM | (42) | GCC GGA ACA TTT TCC ATG TAC TGG GAA GAT GGA GTC TCG AGA | 11 | 13 | 8 | 10 |
| BAK 21 AM | (33) | AGC CAA AAG GAA AAG GAA GGC TTG CAA AAG CAT | 16 | 9 | 5 | 3 |
| BAK 20 AM | (36) | AAT ACC AGC ACT CGC AGA TAT TTT GGC TGC AAA ACC | 12 | 6 | 10 | 8 |
| BAK 19 AM | (33) | ACC AAG GTT GCC GTT GTA GTT TTG CAC GTA GTT | 6 | 9 | 6 | 12 |
| BAK 18 AM | (36) | GGA AAA TGT TCC GGC ACT CTC GTC ATA GGT GAA ATC | 10 | 9 | 8 | 9 |
| BAK 53 AM | (31) | AGC TTC TCG AGA CTC CAT CTT CCC AGT ACA T | 7 | 4 | 11 | 9 |

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 17 amino acids
      (B) TYPE: amino acid
      (C) STRANDEDNESS: single

```
              (D) TOPOLOGY: linear (ii) MOLECULE TYPE: protein (v) FRAGMENT TYPE: N-terminal (vi) ORIGINAL SOURCE:
              (A) ORGANISM: Aspergillus niger var. awamori
              (B) STRAIN: CBS 115.52 (ATCC 11358)

(vii) IMMEDIATE SOURCE:
              (B) CLONE: purified xylanase (xi) SEQUENCE DESCRIPTION: SEQ ID NO:1:

Ser Ala Gly Ile Asn Tyr Val Gln Asn Tyr Asn Gly Asn Leu Gly Asp
1               5                  10                  15
Phe (2) INFORMATION FOR SEQ ID NO:2:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: oligo Xyl01

(xi) SEQUENCE DESCRIPTION: SEQ ID NO:2:

CCRTTRTART TYTGNACRTA RTT                                               23

(2) INFORMATION FOR SEQ ID NO:3:

(i) SEQUENCE CHARACTERISTICS:
              (A) LENGTH: 47 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: oligo Xyl04

(xi) SEQUENCE DESCRIPTION: SEQ ID NO:3:

AAGTCGCCCA GGTTGCCGTT GTAGTTCTGG ACGTAGTTGA TGCCGGC                     47

(2) INFORMATION FOR SEQ ID NO:4:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: oligo Xyl05

(xi) SEQUENCE DESCRIPTION: SEQ ID NO:4:

AAGTCVCCNA RRTTVCCGTT GTA                                               23

(2) INFORMATION FOR SEQ ID NO:5:

(i) SEQUENCE CHARACTERISTICS:
              (A) LENGTH: 47 base pairs
```

```
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: oligo Xyl06

(xi) SEQUENCE DESCRIPTION: SEQ ID NO:5:

AAGTCSCCSA GGTTSCCGTT GTAGTTYTGS ACGTAGTTSA TSCCSGC                47

(2) INFORMATION FOR SEQ ID NO:6:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(vii) IMMEDIATE SOURCE:
          (B) CLONE: primer Xyl11

(xi) SEQUENCE DESCRIPTION: SEQ ID NO:6:

GCATATGATT AAGCTGC                                                17

(2) INFORMATION FOR SEQ ID NO:7:

(i) SEQUENCE CHARACTERISTICS:
          (A) LENGTH: 685 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Aspergillus niger var. awamori
          (B) STRAIN: CBS 115.52 (ATCC 11358)

(vii) IMMEDIATE SOURCE:
          (B) CLONE: pAW14, pAW1

(ix) FEATURE:
          (A) NAME/KEY: intron
          (B) LOCATION: 231..279
          (C) IDENTIFICATION METHOD: experimental
          (D) OTHER INFORMATION: /evidence= EXPERIMENTAL (ix) FEATURE:
          (A) NAME/KEY: sig_peptide
          (B) LOCATION: 1..81

(ix) FEATURE:
          (A) NAME/KEY: mat_peptide
          (B) LOCATION: join(82..230, 280..682)
          (C) IDENTIFICATION METHOD: experimental
          (D) OTHER INFORMATION: /EC_number= 3.2.1.8
              /product= "endo-xylanase II"
              /evidence= EXPERIMENTAL
              /gene= "xylA"

(ix) FEATURE:
          (A) NAME/KEY: CDS
          (B) LOCATION: join(1..230, 280..685)
          (C) IDENTIFICATION METHOD: experimental
          (D) OTHER INFORMATION: /EC_number= 3.2.1.8
              /product= "pre-pro endo-xylanase II"
              /evidence= EXPERIMENTAL
              /gene= "xylA"

(xi) SEQUENCE DESCRIPTION: SEQ ID NO:7:
```

```
ATG AAG GTC ACT GCG GCT TTT GCA GGT CTT TTG GTC ACG GCA TTC GCC        48
Met Lys Val Thr Ala Ala Phe Ala Gly Leu Leu Val Thr Ala Phe Ala
-27     -25                 -20                 -15

GCT CCT GTG CCG GAA CCT GTT CTG GTG TCG CGA AGT GCT GGT ATT AAC        96
Ala Pro Val Pro Glu Pro Val Leu Val Ser Arg Ser Ala Gly Ile Asn
    -10             -5                   1                   5

TAC GTG CAA AAC TAC AAC GGC AAC CTT GGT GAT TTC ACC TAT GAC GAG       144
Tyr Val Gln Asn Tyr Asn Gly Asn Leu Gly Asp Phe Thr Tyr Asp Glu
                10                  15                  20

AGT GCC GGA ACA TTT TCC ATG TAC TGG GAA GAT GGA GTG AGC TCC GAC       192
Ser Ala Gly Thr Phe Ser Met Tyr Trp Glu Asp Gly Val Ser Ser Asp
            25                  30                  35

TTT GTC GTT GGT CTG GGC TGG ACC ACT GGT TCT TCT    AA  GTGAGTGACT    240
Phe Val Val Gly Leu Gly Trp Thr Thr Gly Ser Ser   Asn
        40                  45                     50

GTATTCTTTA ACCAAAGTCT AGGATCTAAC GTTTTCTAG C GCT ATC ACC TAC TCT      295
                                           Ala Ile Thr Tyr Ser
                                                           55

GCC GAA TAC AGT GCT TCT GGC TCC TCT TCC TAC CTC GCT GTG TAC GGC       343
Ala Glu Tyr Ser Ala Ser Gly Ser Ser Ser Tyr Leu Ala Val Tyr Gly
                60                  65                  70

TGG GTC AAC TAT CCT CAG GCT GAA TAC TAC ATC GTC GAG GAT TAC GGT       391
Trp Val Asn Tyr Pro Gln Ala Glu Tyr Tyr Ile Val Glu Asp Tyr Gly
            75                  80                  85

GAT TAC AAC CCT TGC AGC TCG GCC ACA AGC CTT GGT ACC GTG TAC TCT       439
Asp Tyr Asn Pro Cys Ser Ser Ala Thr Ser Leu Gly Thr Val Tyr Ser
        90                  95                  100

GAT GGA AGC ACC TAC CAA GTC TGC ACC GAC ACT CGA ACT AAC GAA CCG       487
Asp Gly Ser Thr Tyr Gln Val Cys Thr Asp Thr Arg Thr Asn Glu Pro
    105                 110                 115

TCC ATC ACG GGA ACA AGC ACG TTC ACG CAG TAC TTC TCC GTT CGA GAG       535
Ser Ile Thr Gly Thr Ser Thr Phe Thr Gln Tyr Phe Ser Val Arg Glu
120                 125                 130                 135

AGC ACG CGC ACA TCT GGA ACG GTG ACT GTT GCC AAC CAT TTC AAC TTC       583
Ser Thr Arg Thr Ser Gly Thr Val Thr Val Ala Asn His Phe Asn Phe
            140                 145                 150

TGG GCG CAG CAT GGG TTC GGA AAT AGC GAC TTC AAT TAT CAG GTC ATG       631
Trp Ala Gln His Gly Phe Gly Asn Ser Asp Phe Asn Tyr Gln Val Met
                155                 160                 165

GCA GTG GAA GCA TGG AGC GGT GCT GGC AGC GCC AGT GTC ACG ATC TCC       679
Ala Val Glu Ala Trp Ser Gly Ala Gly Ser Ala Ser Val Thr Ile Ser
        170                 175                 180

TCT TAA                                                               685
Ser
    185

(2) INFORMATION FOR SEQ ID NO:8:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO:8:

Met Lys Val Thr Ala Ala Phe Ala Gly Leu Leu Val Thr Ala Phe Ala
-27     -25                 -20                 -15

Ala Pro Val Pro Glu Pro Val Leu Val Ser Arg Ser Ala Gly Ile Asn
    -10             -5                   1                   5

Tyr Val Gln Asn Tyr Asn Gly Asn Leu Gly Asp Phe Thr Tyr Asp Glu
```

```
                        10                  15                  20
Ser Ala Gly Thr Phe Ser Met Tyr Trp Glu Asp Gly Val Ser Ser Asp
                    25                  30                  35

Phe Val Val Gly Leu Gly Trp Thr Thr Gly Ser Ser Asn Ala Ile Thr
                40                  45                  50

Tyr Ser Ala Glu Tyr Ser Ala Ser Gly Ser Ser Tyr Leu Ala Val
            55                  60                  65

Tyr Gly Trp Val Asn Tyr Pro Gln Ala Glu Tyr Tyr Ile Val Glu Asp
            70                  75                  80                  85

Tyr Gly Asp Tyr Asn Pro Cys Ser Ser Ala Thr Ser Leu Gly Thr Val
                    90                  95                  100

Tyr Ser Asp Gly Ser Thr Tyr Gln Val Cys Thr Asp Thr Arg Thr Asn
                105                 110                 115

Glu Pro Ser Ile Thr Gly Thr Ser Thr Phe Thr Gln Tyr Phe Ser Val
                120                 125                 130

Arg Glu Ser Thr Arg Thr Ser Gly Thr Val Thr Val Ala Asn His Phe
                135                 140                 145

Asn Phe Trp Ala Gln His Gly Phe Gly Asn Ser Asp Phe Asn Tyr Gln
150                 155                 160                 165

Val Met Ala Val Glu Ala Trp Ser Gly Ala Gly Ser Ala Ser Val Thr
                170                 175                 180

Ile Ser Ser
```

(2) INFORMATION FOR SEQ ID NO:9:

(i) SEQUENCE CHARACTERISTICS:
        (A) LENGTH: 205 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: synthetic fragment BAK1

(xi) SEQUENCE DESCRIPTION: SEQ ID NO:9:

```
GAATTCCTCG AGCGACTTTG TCGTTGGTCT GGGCTGGACC ACTGGTTCTT CTAACGCTAT      60

CACCTACTCT GCCGAATACA GTGCTTCTGG CTCCTCTTCC TACCTCGCTG TGTACGGCTG     120

GGTCAACTAT CCTCAGGCTG AATACTACAT CGTCGAGGAT TACGGTGATT ACAACCCTTG     180

CAGCTCGGCC ACAAGCCTTG GTACC                                           205
```

(2) INFORMATION FOR SEQ ID NO:10:

(i) SEQUENCE CHARACTERISTICS:
        (A) LENGTH: 202 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: synthetic fragment BAK2

(xi) SEQUENCE DESCRIPTION: SEQ ID NO:10:

```
GAATTCGAGC TCATCACACA AACAAACAAA ACAAAATGAT GCTTTTGCAA GCCTTCCTTT      60

TCCTTTTGGC TGGTTTTGCA GCCAAAATAT CTGCGAGTGC TGGTATTAAC TACGTGCAAA     120

ACTACAACGG CAACCTTGGT GATTTCACCT ATGACGAGAG TGCCGGAACA TTTTCCATGT     180
```

ACTGGGAAGA TGGAGTCTCG AG                                                      202

(2) INFORMATION FOR SEQ ID NO:11:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
         (B) CLONE: synthetic fragment BAK4

(xi) SEQUENCE DESCRIPTION: SEQ ID NO:11:

GAATTCGCCG CGGGTATTAA CTACGTGCAA AACTACAACG GCAACCTTGG TGATTTCACC              60

TATGACGAGA GTGCCGGAAC ATTTTCCATG TACTGGGAAG ATGGAGTCTC GAG                    113

(2) INFORMATION FOR SEQ ID NO:12:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
         (B) CLONE: PGK1 promoter (PCR)

(xi) SEQUENCE DESCRIPTION: SEQ ID NO:12:

GGAATTCAGA TCTTGAATTG ATGTTACCCT CATAAAGCAC GTGGCCTCTT ATCGAGAAAG              60

AAATTACCGT CGCTCGTGAT TTGTTTGCAA AAAGAACAAA ACTGAAAAAA CCCAGACACG             120

CTCGACTTCC TGTCTTCCTA TTGATTGCAG CTTCCAATTT CGTCACACAA CAAGGTCCTA             180

GCGACGGCTC ACAGGTTTTG TAACAAGCAA TCGAAGGTTC TGGAATGGCG GGAAAGGGTT             240

TAGTACCACA TGCTATGATG CCCACTGTGA TCTCCAGAGC AAAGTTCGTT CGATCGTACT             300

GTTACTCTCT CTCTTTCAAA CAGAATTGTC CGAATCGTGT GACAACAACA GCCTGTTCTC             360

ACACACTCTT TTCTTCTAAC CAAGGGGGTG GTTTAGTTTA GTAGAACCTC GTGAAACTTA             420

CATTTACATA TATATAAACT TGCATAAATT GGTCAATGCA AGAAATACAT ATTTGGTCTT             480

TTCTAATTCG TAGTTTTTCA AGTTCTTAGA TGCTTTCTTT TTCTCTTTTT TACAGATCAT             540

CAAGGAAGTA ATTATCTACT TTTTACAACA AATATAAAAC AATGCGCAGC AGGTAAGCTT             600

GGG                                                                          603

(2) INFORMATION FOR SEQ ID NO:13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
         (B) CLONE: primer PGP01

(xi) SEQUENCE DESCRIPTION: SEQ ID NO:13:

GGAATTCAGA TCTTGAATTG ATGTTACCCT CATAAAGCAC GTG                                43

(2) INFORMATION FOR SEQ ID NO:14:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: primer PGP02

(xi) SEQUENCE DESCRIPTION: SEQ ID NO:14:

```
CCCAAGCTTA CCTGCTGCGC ATTGTTTTAT ATTTGTTGTA AAAAGTAGAT AATTACTTCC      60
```

(2) INFORMATION FOR SEQ ID NO:15:

(i) SEQUENCE CHARACTERISTICS:
        (A) LENGTH: 208 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: synthetic fragment BAK5

(xi) SEQUENCE DESCRIPTION: SEQ ID NO:15:

```
GAATTCGAGC TCATCACACA AACAAACAAA ACAAAATGAT GCTTTTGCAA GCCTTCCTTT      60
TCCTTTTGGC TGGTTTTGCA GCCAAAATAT CTGCGAGTGC TGGTATTAAC TACGTGCAAA     120
ACTACAACGG CAACCTTGGT GATTTCACCT ATGACGAGAG TGCCGGAACA TTTTCCATGT     180
ACTGGGAAGA TGGAGTCTCG AGAAGCTT                                         208
```

(2) INFORMATION FOR SEQ ID NO:16:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
AATTCGAGCT CATCACACAA ACAAACAAAA CAAAATGATG CTTTTGCAAG CC              52
```

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
TTCCTTTTCC TTTTGGCTGG TTTTGCAGCC AAAATA                                36
```

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:18:

TCTGCGAGTG CTGGTATTAA CTACGTGCAA AACTAC                                    36

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AACGGCAACC TTGGTGATTT CACCTATGAC GAGAGT                                    36

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GCCGGAACAT TTTCCATGTA CTGGGAAGAT GGAGTC                                    36

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CATTTTGTTT TGTTTGTTTG TGTGATGAGC TCG                                       33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

AGCCAAAAGG AAAAGGAAGG CTTGCAAAAG CAT                                       33

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

AATACCAGCA CTCGCAGATA TTTTGGCTGC AAAACC                             36

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ACCAAGGTTG CCGTTGTAGT TTTGCACGTA GTT                                33

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GGAAAATGTT CCGGCACTCT CGTCATAGGT GAAATC                             36

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TCGAGACTCC ATCTTCCCAG TACAT                                         25

(2) INFORMATION FOR SEQ ID NO:27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

AATTCGCCGC GGGTATTAAC TACGTGCAAA ACTA                               34

(2) INFORMATION FOR SEQ ID NO:28:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

ACCAAGGTTG CCGTTGTAGT TTTGCACGTA GTTAATACCC GCGGCG                  46

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TCGAGACTCC ATCTTCCCAG TACAT                                            25

(2) INFORMATION FOR SEQ ID NO:30:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

AATGATGCTT TTGCAAGCCT TCCTTTTCCT TTTGGCTGGT TTTGCAGCCA AAATA        55

(2) INFORMATION FOR SEQ ID NO:31:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GCCGGAACAT TTTCCATGTA CTGGGAAGAT GGAGTCTCGA GA                    42

(2) INFORMATION FOR SEQ ID NO:32:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

AGCTTCTCGA GACTCCATCT TCCCAGTACA T                                  31

(2) INFORMATION FOR SEQ ID NO:33:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

AATTCCTCGA GCGACTTTGT CGTTGGTCTG GGCTGGACCA CTGGTTCT              48

(2) INFORMATION FOR SEQ ID NO:34:

(i) SEQUENCE CHARACTERISTICS:

(A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TCTAACGCTA TCACCTACTC TGCCGAATAC AGT                    33

(2) INFORMATION FOR SEQ ID NO:35:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GCTTCTGGCT CCTCTTCCTA CCTCGCTGTG TACGGCTGG             39

(2) INFORMATION FOR SEQ ID NO:36:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GTCAACTATC CTCAGGCTGA ATACTACATC GTCGAGGATT AC          42

(2) INFORMATION FOR SEQ ID NO:37:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GGTGATTACA ACCCTTGCAG CTCGGCCACA AGCCTTGGTA C           41

(2) INFORMATION FOR SEQ ID NO:38:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CAGACCAACG ACAAAGTCGC TCGAGG                            26

(2) INFORMATION FOR SEQ ID NO:39:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

GTAGGTGATA GCGTTAGAAG AACCAGTGGT CCAGCC        36

(2) INFORMATION FOR SEQ ID NO:40:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GTAGGAAGAG GAGCCAGAAG CACTGTATTC GGCAGA        36

(2) INFORMATION FOR SEQ ID NO:41:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

TTCAGCCTGA GGATAGTTGA CCCAGCCGTA CACAGCGAG        39

(2) INFORMATION FOR SEQ ID NO:42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GTTGTAATCA CCGTAATCCT CGACGATGTA GTA        33

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

CAAGGCTTGT GGCCGAGCTG CAAGG        25

XYLANASE PRODUCTION

This invention lies in the field of recombinant DNA technology and is directed at a cell having a certain function in a process, containing recombinant DNA encoding at least one enzyme. The invention is directed especially at a cell having a function in the field of food processing and also at cells with a function in processes in which a cellulose-containing raw material is used, such as processes for preparing beer, paper, starch, gluten etc, and processes for decomposing cellulose-containing waste such as agricultural waste, waste from paper rills etc.

In particular the invention is directed at cells having a function in the process of fermentation, more especially at cells with a function in the process of preparing bakery products.

The cell according to the invention is characterized in that the cell becomes polyfunctional for the process in which it has a function, upon expression of the recombinant DNA encoding at least one enzyme. In the case of a fermentation process for example, such as the preparation of bread, yeast is used as a cell with a particular function in said process. A yeast cell according to the invention does not only have its normal function, i.c. a function that a yeast lacking the recombinant DNA can also carry out, but also has another function in said process of bread preparation. An example of such an additional function is the expression and secretion of a bread improving enzyme.

The present invention is directed in particular at a cell with a function in the preparation of bakery products. Cells containing recombinant DNA encoding enzymes selected from the group of enzymes with amylolytic and/or hemicellulolytic and/or cellulolytic activity are suitable.

The invention is also directed at a process for the production of at least one enzyme by a polyfunctional cell as described above comprising culturing such a polyfunctional cell in a suitable nutrient medium and optionally isolating the resulting enzyme form. In such a process, said enzyme is preferably selected from the group of enzymes with amylolytic and/or hemicellulolytic and/or cellulolytic activity. A suitable medium for carrying out the process according to the invention can consist of the medium in which the process for which the cell is polyfunctional is carried out. In the process of the preparation of a bakery product for example said medium can be the dough that it to be baked. Naturally the other usual media for culturing cells can also be used. The choice of media will depend on whether the enzyme is to be used in situ or has to be isolated. In some cases it will suffice to use the medium containing said enzyme and in other cases the enzyme will have to be isolated from the medium.

The invention is also directed at an enzyme encoded by the recombinant DNA in said polyfunctional cell, whereby said enzyme is obtainable from such a polyfunctional cell via the afore mentioned process for producing an enzyme. The invention is further directed at the use of such a polyfunctional cell or such an enzyme, for example in the processes described above, such as food processing and processes using a cellulose containing raw material, preferably in a process for the preparation of a bakery product.

Flour, yeast, water and salt are the basic ingredients of bread and other bakery products. For centuries materials having a positive effect on the manageability of the dough or the quality of the baked product have been added in the manufacture of bread and similar bakery products, for the sake of convenience further referred to as bread making. Said additives, referred to as "bread improvers", contain enzymes from malt or of microbial origin which play an important part in the different phases of bread making, namely, the preparation of the bread batter, fermentation, baking, and storage of the bread product.

One of the relevant characteristics of bread that is influenced by adding specific enzymes is the so-called bread volume. In order to obtain a high bread volume in practice compositions containing cellulolytic, hemicellulolytic and/or amylolytic enzymes are added. The commercially available compositions of microbial origin, mostly originating from a fungus o; one of the genera Aspergillus and Trichoderma, are substantially unpurified complex mixtures of different enzyme activities, whereby it is not exactly known which enzymes are present in the composition and which have a bread improving activity. This lack of knowledge impedes further bread improvement and especially impedes the control of the different dough processing and bread properties, such as the bread volume.

Further investigation into the process of preparation of bakery products resulted in the discovery that, in addition to α-amylase, at least a xylanase enzyme is also of importance for the bread volume. A xylanase is an enzyme that catalyzes the degradation of xylans occurring in the pentosan part of starch "tailings". The term "tailings" is directed at a fraction of, e.g., wheat starch consisting of water-insoluble hemicellulose (pentosans and arabinoxylans) and damaged starch. This fraction is formed as the intermediate or top layer of the starch pellet during centrifugation of a dough suspension obtained by washing dough to remove the gluten fraction.

Different xylanases have already been described in the literature, including xylanases of the bacterial species *Bacillus pumilus* (Panbangred et al., Mol. Gen. Genet. 192, 335–341, 1983, and Fukusaki et al., FEBS Lett. 321, 197–201, 1984), *Bacillus subtilis* (Paice et al., Arch. Microbiol. 144, 201–206, 1986), and *Bacillus circulans* (Yang et al., Nucl. Acids Res. 16, 7187, 1988), of the yeast Aureobasidium (Leathers, Biotech. Lett. 12, 775–780, 1988) and of the fungus *Aspergillus niger* (Fournier et al., Biotechnology and Bioengineering 27, 539–546, 1985).

It is known from European patent application EP-A-0338452 that the properties of dough and the quality of bread can be improved by adding different enzyme compositions to the dough, including an enzyme composition having hemicellulose degrading or xylanase activity, the origin of which is not further specified. Such a hemicellulolytic enzyme composition is a relatively undefined enzyme mixture which may contain different hemicellulolytic enzymes having various effects on the dough and bread properties. The presence of xylanases having bread improving activity to a smaller or greater extent is the coincidental result of the manner in which the enzyme composition that is intended as a bread improver has been obtained. A controlled further optimization of bread improvers, however, was not possible due to the lack of the required knowledge and of suitable recombinant DNA constructs encoding a xylanase having broad improving activity that could be used for a high production of such a xylanase.

For the purpose of this invention, "bread improving activity" is generally taken to mean a favourable effect on any property of the prepared bakery product (including bread) or of the dough from which the bakery or bread product is made, and is particularly taken to mean a favourable effect on the bread volume.

The investigation on which the invention is based has extended to the identification and cloning of a gene (xylA) encoding an enzyme, xylanase having bread improving activity, originating from a fungus of the species *Aspergillus* niger var. awamori, as well as to the transformation of different species of host cells in such a manner that the gene is expressed or can be expressed in said host cells. The invention, however, comprises all xylanase genes originating from fungi and especially from fungal strains from the same genus and therefore the invention is not limited to the actually cloned gene.

The present invention is therefore also directed at recombinant DNA material comprising DNA with a nucleotide sequence encoding at least a ripening form of a xylanase of fungal origin.

The term "ripening form" refers to the different forms in which the enzyme may occur after expression of the associated gene. More in particular, it refers to both the naturally and the not naturally occurring prepro-, pre- and pro-forms and to the ultimate mature form of the enzyme resulting after cleavage of a "leader" peptide.

More in particular, the invention, relates to recombinant DNA material comprising DNA with a nucleotide sequence encoding at least a ripening form of a xylanase of Aspergillus origin.

Preferably, this aspect of the invention is concerned with recombinant DNA material comprising DNA with a nucleotide sequence encoding a ripening form of a xylanase of Aspergillus niger origin, especially of Aspergillus niger var. awamori origin.

A preferred embodiment of this aspect of the invention is recombinant DNA material comprising DNA with a nucleotide sequence encoding at least a ripening form of xylanase with an amino acid sequence as shown in FIG. 1 (SEQ ID NO:7), and more in particular recombinant DNA material comprising DNA with a nucleotide sequence encoding a ripening form of xylanase, as shown in FIG. 1 (SEQ ID NO:7). The invention is also directed at recombinant DNA material comprising DNA with a nucleotide sequence encoding at least a ripening form of xylanase with a nucleotide sequence that is equivalent to the nucleotide sequence of FIG. 1 (SEQ ID NO:7) with deletions, insertions or alterations in comparison to the nucleotide sequence of FIG. 1 (SEQ ID NO:7) such that the nucleotide sequence with deletions, insertions or alterations corresponds either to the amino acid sequence as shown in FIG. 1 (SEQ ID NO:7) or to those parts of the amino acid sequence of FIG. 1 (SEQ ID NO:7) essential for an active ripening form of xylanase such as mature xylanase or active pre(pro) xylanase or the nucleotide sequence with deletions, insertions or alterations has a complementary strand capable of hybridizing under hybridizing conditions to the nucleotide sequence of FIG. 1 (SEQ ID NO:7).

The the recombinant DNA according to the invention contains at least a sequence encoding the fungal, in particular the Aspergillus xylanase ripening form. In addition, the recombinant DNA may contain many other types of information, such as regulating sequences (especially a transcription promoter) and a vector part usually provided with one or more marker genes. These other types of information will often be connect d with the selected host. Thus, for instance, the vector, the marker genes and the regulating sequences will be selected depending on the selected host.

The recombinant DNA encoding at least a ripening xylanase of fungal origin, however, may also contain other genes to be expressed in the selected host. Such a gene may advantageously encode at least one other enzyme, wherein said other enzyme has amylolytic and/or hemicellulolytic and/or cellulolytic activity.

Another aspect of the invention is a cell containing genetic material derived from recombinant DNA material according to the invention as defined above, and more in particular such a cell capable of expression of at least the xylanase ripening form encoded on said recombinant DNA material. A preference exists for such a cell that is also a polyfunctional cell according to the invention and more especially for such a polyfunctional cell capable of expressing the recombinant DNA material encoding a ripening form of xylanase of fungal origin under conditions present in raw material during preparation of a bakery product.

Both a polyfunctional cell containing recombinant DNA encoding at least one enzyme according to the invention, and a cell containing recombinant DNA material encoding a ripening form of xylanase of fungal origin according to the invention (as well as the combination thereof) may either be a cell which is itself the direct result of gene manipulation or be a cell originating in any manner from a cell that has been transformed by such gene manipulation. The invention further extends to both live cells and cells that are no longer alive.

In principle the invention knows no special limitations with respect to the nature of the cells, whereby those cells capable of expression of a xylanase ripening form of fungal origin are preferred. However the cells are preferably selected from the group consisting of bacterial cells, fungal cells, yeast cells, and plant cells.

Preferred examples of eminently suited host cells are
(a) fungal cells of one of the genera Aspergillus and Trichoderma, in particular fungal cells of one of the species *Aspergillus niger* var. niger, *Aspergillus niger* var. awamori, *Aspergillus nidulans, Aspergillus oryzae Trichoderma reisei* and *Trichoderma viride;*
(b) yeast cells of one of the genera *Saccharomyces, Kluyveromyces, Hansenula* and *Pichia,* in particular yeast cells of one of the species *Saccharomyces cerevisiae, Saccharomyces carlbergensis, Kluyveromyces lactis, Kluyveromyces marxianus, Hansenula polymorpha* and *Pichia I storis;*
(c) plant cells of a plant genus selected from the group consisting of wheat, barley, oats, maize, pea, potato and tobacco, such as plant cells of one of the species *Solanum tuberosum* and *Nicotiana tabacum;* and
(d) bacterial cells of one of the bacterial genera *Bacillus, Lactobacillus* and *Streptococcus,* such as bacteria of the species *Bacillus subtilis.*

Cells according to the invention as defined above (polyfunctional and/or simply containing recombinant DNA encoding a ripening form of xylanase of fungal origin) may be important as agents for multiplying the recombinant DNA or as agents for producing at least one enzyme encoded on said recombinant DNA, such as the ripening form of xylanase.

In the case of enzyme production it is possible to use the cell to produce enzyme and either isolate the enzyme from the culturing medium or use the medium containing the enzyme after removal of the cells as such, or in the case of the polyfunctional cells to use the cells themselves to produce the enzyme in situ in the process for which they are poly-functional.

A direct use of the cells themselves is possible, e.g., if the host strain can be admitted without objection, in the production of foodstuffs as is the case for various fungal, yeast, plant, and bacterial species. In connection with bread making the yeast strains that are genetically manipulated in accordance with the present invention can for example be used directly.

Partly depending on the selected host the gene encoding xylanase will be used, either with or without introns occurring in said gene, either with its own transcription termination signals or originating from another gene, and either with its own leader sequence or with a signal sequence originating from another gene. For transformation of yeast, such as *Saccharomyces cerevisiae* (baker's yeast), it is preferable that the introns are removed and that the own leader sequence is replaced by a signal sequence suitable for yeast, such as the signal sequence of the invertase gene, ensuring correct processing and secretion of the mature protein.

The removal of introns is necessary upon transformation of bacteria, such as *Bacillus subtilis*. In this case e.g. the α-amylase signal sequence can be used as signal sequence.

Suitable transformation methods and suitable expression vectors provided with, e.g., a suitable transcription promoter, suitable transcription termination signals, and suitable marker genes for selecting transformed cells are already known for many organisms, including different bacterial, yeast, fungal, and plant species. Reference may be made for yeast for example to Tajima et al., Yeast 1, 67–77, 1985, which shows expression of a foreign gene under control of the GAL7 promoter inducible by galactose in yeast, and for *Bacillus subtilis* for example to EP-A-0 157 441, describing a plasmid pMS48 containing the SPO2 promoter as an expression vector. For other possibilities in these and other organisms reference is made to the general literature.

In another aspect the present invention consists of a ripening form of a xylanase of a fungus, in particular of Aspergillus origin, obtained by expression of recombinant DNA material according to the invention, as defined above. Herein, special preference is given to a mature xylanase with an amino acid sequence as illustrated in FIG. 1, as well as to a pre(pro)-xylanase with an amino acid sequence as illustrated in FIG. 1 (SEQ ID Nos: 7 and 8) and to any amino acid sequence of an active equivalent form of xylanase comprising the amino acids of the sequence of FIG. 1 which are essential for xylanase activity. The invention is therefore directed at an amino acid structure leading to a tertiary enzyme structure with the same enzyme activity as the enzyme with the sequence of FIG. 1.

Yet another aspect of the invention consists of a process for producing a ripening form of a xylanase of a fungus, in particular of Aspergillus origin, comprising culturing a polyfunctional cell capable of expressing a xylanase ripening form and or a cell capable of expressing the recombinant DNA material according to the invention encoding a ripening form of xylanase of fungal origin in a suitable nutrient medium, and optionally isolating the resulting xylanase ripening form. The term "isolating the resulting xylanase ripening form" also comprises a partial purification in which an enzyme composition is recovered comprising the relevant xylanase.

Further aspects of the present invention are a bread improver composition comprising an enzyme selected from the group of enzymes with amylolytic and/or hemicellulolytic and/or cellulolytic activity such as a ripening form of xylanase, in particular a mature xylanase of a fungus, especially of Aspergillus origin, whereby said enzyme is obtainable from a polyfunctional cell according to the invention and/or from expression of recombinant DNA according to the invention encoding a ripening form of a xylanase of fungal origin and a bread improver composition comprising a polyfunctional cell according to the invention; a flour and dough composition comprising an enzyme selected from the group of enzymes with amylolytic and/or hemicellulolytic and/or cellulolytic activity such as a ripening form of xylanase, in particular a mature xylanase of a fungus, especially of Aspergillus origin, whereby said enzyme is obtainable from a polyfunctional cell according to the invention and/or from expression of recombinant DNA according to the invention encoding a ripening form of a xylanase of fungal origin; a flour and dough composition comprising a polyfunctional cell according to the invention; a bakery product obtained using such flour or dough compositions as described above; and a process for the preparation of a bakery product, using such flour or dough compositions especially in which a mature xylanase of a fungus, in particular of Aspergillus origin is included.

The invention, however, also extends to other uses of fungal xylanases, such as use within the scope of beer making, particularly the preparation of beers on the basis of wheat, in order to improve filterability, use in the papermaking industry to reduce water absorption by the paper material, use in the treatment of agricultural waste, etc.

The invention will now be elucidated by means of an extensive description of the identification, cloning and expression of a xylanase suitable as a bread improver. In the experimental work described in the examples the fungal strain *Aspergillus niger* var. *awamori* CBS 115.52 (ATCC 11358) is used as a source for the xylanase. According to investigations carried out by the inventors, said strain, after induction with wheat bran, is capable of producing a xylanase having bread improving properties, while the culture medium exhibits an α-amylase activity, a low glucanase activity and a low protease activity under these induction conditions. The amount of xylanase produced by the wild-type strain, however, is too low for use in a commercial process. For this reason the invention also provides gene manipulations enabling a biotechnological production of the xylanase on a commercial scale.

The conducted experimental work comprises the isolation of the gene encoding a xylanase enzyme (the xylA gene) from a gene library of chromosomal *Aspergillus niger* var. *awamori* DNA made in a λ vector. For said isolation a probe was made with a composition derived from the N-terminal amino acid sequence of the purified mature protein as determined by the inventors. By means of this probe a number of λ clones were isolated which possibly contained the gene. A DNA fragment from these positive λ clones was subcloned. Subsequently, the DNA sequence of part of the cloned chromosomal DNA fragment was determined. By means of these results and those of mRNA analysis, the length of the xylA gene, the length of the mRNA, and the presence and position of an intron have been determined. It could be derived from the data that the xylA gene encodes a protein of 211 amino acids (a pre(pro)-form) in which the mature protein of 184 amino acids is preceded by a "leader" peptide of 27 residues.

Three expression vectors containing the xylanase gene including the xylA terminator have been constructed. In one of these vectors the xylA gene is preceded by its own expression signals. In the second vector the xylA expression signals (up to the ATG codon) have been replaced by the constitutive expression signals of the *Aspergillus nidulans* glyceraldehyde 3-phosphate dehydrogenase (gpdA) gene (see Punt et al., Gene 69, 49–57, 1988), while in the third vector the xylA gene is preceded by the inducible expression signals of the *Aspergillus niger* var. *niger* glucoamylase (glaA) gene. All the expression vectors contain the *Aspergillus nidulans* acetamidase (amdS) gene as selection marker as described by K. Wernars, "DNA mediated transformation of the filamentous fungus Aspergillus nidulans", thesis, Landbouw Hogeschool Wageningen 1986. By means of this selection marker transformants can be obtained in which the vector, and consequently also the xylA gene, is integrated into the genome in a large number of copies.

Multicopy transformants were obtained by transformation of the Aspergillus strains *A. niger* var. *awamori* and *A. niger* var. *niger* N402 with the above mentioned expression vectors. In shaking flask experiments the production of xylanase was measured after culturing the resulting transformants in different media. The results (maximum production levels) are listed in Table A given below, in which the xylanase activity is expressed in $10^3$ units (U) per ml. A unit is defined as the amount of enzyme which, per 1 minute, releases an amount of reducing groups from xylan equivalent to 1 mg xylose.

Survey of the maximum xylanase production levels in shaking flask experiments after culturing in different media

| strain | promoter xylan | rich medium | starchbran |
|---|---|---|---|
| A. niger var. awamori | xyl A s.c. | 15 | 0 0 14 |
| A. niger var. niger N402 | xyl A s.c. | 5 | n.d. n.d. |
| A. niger var. awamori | xyl A m.c. | 59 | 78 |
| A. niger var. niger N402 | xyl A m.c. | n.d. | 120 |
| A. niger var. niger AB4.1 | xyl A m.c. | 36 | 140 |
| A. niger var. awamori | gpdA m.c. | 20 | 32 |
| A. niger var. niger N402 | gpdA m.c. | 11 | 12 |
| A. niger var. awamori | glaA m.c. | 71 | 45 |
| A. niger var. niger N402 | glaA m.c. | 54 | 72 | s.c.: single copy wild type strain
m.c.: multicopy transformants
n.d.: not determined After induction with xylan the *A. niger* var. *awamori* and *A. niger* var. *niger* N402 "xylA" multicopy transformants with xylA promoter produce much more xylanase than the wild type *A. niger* var. *awamori* and *A. niger* var. *niger* strains. From this and from data obtained in the molecular analysis of the gene it can be derived that the cloned gene encodes a functional xylanase. Furthermore it is apparent from the afore mentioned that the multicopy transformants are capable of overproduction of the active enzyme. In baking tests this enzyme composition also has the desired properties.

Multicopy transformants of the host strains with the heterologous gpdA or glaA promoter are also capable of an increased production of active xylanase. In rich medium the "gpdA" transformants produce a clearly larger amount of xylanase than the wild type *A. niger* var. *awamori* strain. However, the production levels observed in the conducted tests are substantially lower than the level obtained in the tests with "xylA" multicopy transformants. After induction with starch the production levels of "glaA" multicopy transformants are comparable to those of "xylA" multicopy transformants in xylan medium.

In medium with wheat bran the best *A. niger* var. *awamori* "xylA" multicopy transformants produce much more xylanase than is the case in xylan medium. In this medium the best *A. niger* var. *niger* N402 "xylA" transformants reach a very high xylanase production level. The highest producing "gpdA" multicopy transformants of both *A. niger* var. *awamori* and of *A. niger* var. *niger* N402 in bran produce as much xylanase as in rich medium. In medium with wheat bran the production by *A. niger* var. *awamori* "glaA" transformants is lower than in starch. In this medium, however, *A. niger* var. *niger* N402 "glaA" transformants produce more than in starch.

The production reached by *Aspergillus niger* var. *niger* N402 transformants is higher than that of *Aspergillus niger* var. *awamori* transformants. The production level of the *A. niger* var. *awamori* transformants, however, can be further increased by using suitable *A. niger* var. *awamori* mutant strains, such as *A. niger* var. *awamori* #40, which produces clearly more xylanase than the wild type strain. The mutant *A. niger* var. *awamori* #40 has been obtained by mutagenesis of *A. niger* var. *awamori* spores and selection for xylanase production. In bran medium the "xylA" *A. niger* var. *awamori* #40 transformant produced 190 000 U xylanase, which is a considerable increase over the best producing *A. niger* var. *awamori* transformant.

Further experiments relate to the isolation and use of the thus produced xylanase as a bread improver (see example II) and expression experiments in a yeast strain and a bacterium (examples III and IV, respectively). While example V demonstrates the use of a polyfunctional yeast according to the invention in the preparation of bread, whereby said yeast produces xylanase during fermentation of lean bread dough.

BRIEF DESCRIPTION OF THE DRAWINGS

FIG. 1 (SEQ ID NO:7) shows the DNA sequence of a part of a ca 2.1 kb PtI-PstI *Aspergillus niger* var. *awamori* fragment present in the plasmid pAW14B, which fragment contains a gene encoding a xylanase, indicated as the xylA gene. The translation start and the stop codon are doubly underlined; The 49 bp intron is underlined. The start of the mature protein is indicated. The amino acid acid sequence of the protein (both of the pre(pro-form and of the mature protein) is also mentioned in FIG. 1 (SEQ ID NO: 7), using the one-letter code.

FIG. 2 shows the restriction map of the genomic DNA region of *A. niger* var. *awamori*, comprising the xylA gene cloned in the phages λ-1 and λ-14. The used abbreviations stand for: S: SalI; E: EcoRI; H: HindIII; P: PstI; B: BamHI; S#: SalI site originating from the polylinker of λ-EMBL3; D: Sau3A. The massive bar indicates a 1.2 kb PstI*-BamHI fragment hybridizing with Xy106.

FIG. 8 (SEQ ID NO:s 9 and 33–43) shows the nucleotide sequences of the DNA fragment BAK1 and of the synthetic oligonucleotides from which this fragment is built up.

FIG. 10 shows the nucleotide sequences of the DNA fragment BAK2 and of the synthetic oligonucleotides from which this fragment is built up.

FIG. 15 (SEQ ID NO:s11, 27,19,20,28,25 and 29) shows the nucleotide sequences of the DNA fragment BAK4 and of the synthetic oligonucleotides from which this fragment is built up.

FIG. 18 shows the nucleotide sequence of the in vitro amplified *S. cerevisiae* PGK promoter. In the double stranded sequence the primers are shown bold, the ATG start codon is on a shaded background, and the restriction sites EcoRI, BqlII, BspMI and HindIII are indicated.

FIG. 20 (SEQ ID NO:s 15,30,18,19,31,22,23,24,25 and 32) shows the nucleotide sequences of the DNA fragment BAK5 and of the synthetic oligonucleotides from which this fragment is built up.

EXAMPLE I

Figure 3:
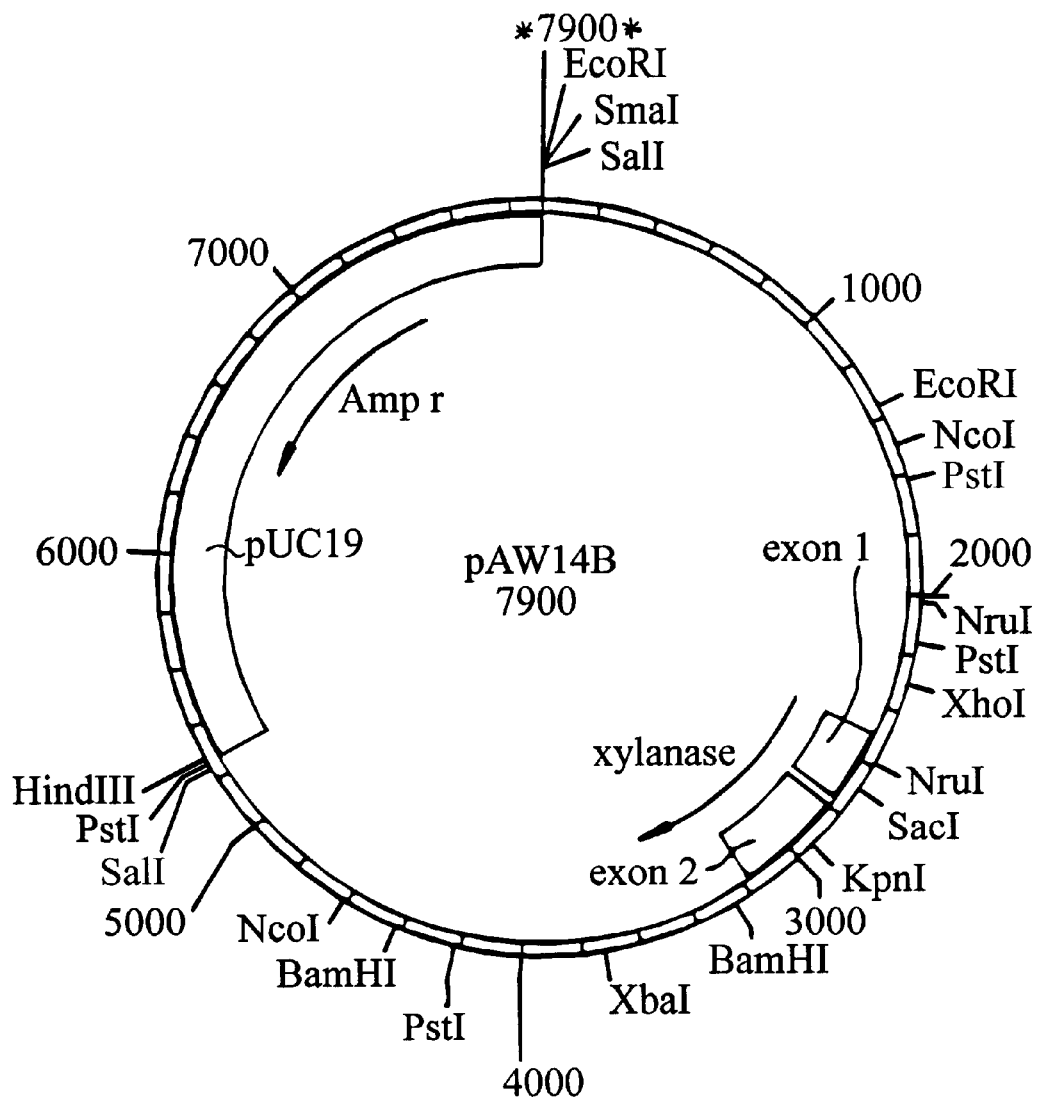
FIG. 3 shows the plasmid pAW14B obtained by an insertion of a 5.3 kb *A. niger* var. *awamori* SalI fragment in pUC19.

Cloning and Characterisation of the Xylanase Gene (xylA) of *Aspergillus niger* var. *awamori*

1.1 Isolation of the *Aspergillus niger* var. *awamori* xylA Gene

In order to isolate the xylA gene from chromosomal DNA of *Aspergillus niger* var. *awamori* different probes were synthesized consisting of mixtures of oligonucleotides (Table B). The composition of these mixtures was derived from the N-terminal amino acid sequence of purified xylanase protein.

mentary to the part of the coding strand encoding the amino acids 2–17.

Xyl03(SEQ ID NO: 4) a mixture of 144 oligonucleotides having a length of 23 desoxynucleotides of which the sequence is complementary to the part of the coding strand encoding the amino acids 10–17.

Xyl06(SEQ ID NO:5) a mixture of 256 oligonucleotides having a length of 47 desoxynucleotides the sequence of which is complementary to the part of the coding strand encoding the amino acids 2–17.

In Xyl05(SEQ ID NO:4) and Xyl06(SEQ ID NO:5) not all of the bases that can possibly occur are introduced at the third position of the codons in order to obtain no more than 256 oligonucleotides in the mixture.

By means of Southern blot analysis it was established that in digests of chromosomal DNA—under stringent conditions—only one band hybridizes with the probes used. In the EcoRI, SalT and BamHI digest of *Aspergillus niger* var. *awamori* DNA one band of respectively 4.4, 5.3 and 9.5 kb hybridizes with both Xyl01, Xyl04 and Xyl06(SEQ ID NO:s 2, SEQ ID NO:3 and SEQ ID NO:5, respectively). With Xyl05(SEQ ID NO:4) no clear signal was found at 41° C. On the basis of this result a λ gene library of *Aspergillus niger* var. *awamori* DNA was hybridized at 65° C. with the oligonucleotide mixture xyl06(SEQ ID NO:8) as a probe. Of the 65000 tested plaques (corresponding to 32 times the genome) three plaques (λ-1, λ-14 and λ-63) hybridized with this probe. After hybridization of digests of λ-1 and λ-14 DNA with Xyl06 a hybridizing band of >10 kb was found in the EcoRI digest of λ-1. The size of the hybridizing band in the λ-14 and the chromosomal EcoRI digest was 4.4. kb. In the SalI digest of λ-1 a 4.6 kb band hybridizes; in the SalI digest of λ-14 this is, like in chromosomal DNA, a 5.3 kb band. Also a 1.2 kp PstI-BamHI fragment (FIG. 2) hybridizes with Xyl06(SEQ ID NO:5). On the basis of restriction patterns with different enzymes and cross-hybridization of λ-1 and λ-14 digests with the 5.3 kb SalI fragment of λ-14 it was confirmed that these λ's contained overlapping fragments of the genome of *Aspergillus niger* var. *awamori*. Also homologous hybridization of total induced RNA with respectively λ-1, λ-14 and the 5.3 kb SAlI fragment of

TABLE B

Probes derived from the N-terminal amino acid sequence of xylanase protein

N-terminal amino acid sequence of xylanase protein: (SEQ ID NO:1)

```
1        5         10            15
SerAlaGlyIleAsnTyrValGlnAsnTyrAsnGlyAsnLeuGlyAspPhe probe              base sequence 3'–5'

Xyl01 (SEQ ID NO:2)    TTAATACAXGTTTTAATATTACC
                        G G     C G G G
Xyl04 (SEQ ID NO:3)            C G G C C G T A G T T G A T G C A G -
GTCTTGATGTTGCCGTTGGACCCGCTGAA
Xyl05 (SEQ ID NO:4)    ATGTTGCCATTAAAXCCACTGAA
                         G  GG  G
                         C  C
Xyl06 (SEQ ID NO:5)    CGGCCGTAGTTGATGCAGGTCTTGATGTTGCCGTTGGAGCCGCTGAA
                         C C C        C T      C    C C
```

X = A, G, C or T
Xyl01:(SEQ ID NO:2) a mixture of 256 oligonucleotides having a length of
23 desoxynucleotides of which the sequence is complementary to the part
of the coding strand encoding the amino acids 5–12.

Xyl04(SEQ ID NO:3): an oligonucleotide having a length of 47 desoxynucleotides of which the sequence is comple- λ1–14 confirmed the presence of xyl A sequences on these λ's. Hybridization was found with a xylan-induced mRNA of ca. 1 kb. The size thereof corresponds to that of the ARNA molecule hybridizing with Xyl06.

1.2 Subcloning of the *A. niger* var. *awamori* xyl A Gene

The SalI fragments hybridizing with Xyl06 of respectively λ-1 (4.6 kb) and λ-14 (5.3 kb) were cloned in two orientations in the SalI site of pUC19, which resulted in plasmid pAW1 (A and B) and plasmid pAW14 respectively (A and B, see FIG. 3). The 1.2 kb PstI-BamHI fragment hybridizing with Xyl06 and the adjacent 1.0 kb BAmHI-PstI fragment from respectively pAW14A and pAW1A were subcloned into M13mp18 and M13mp19 cleaved with BamHI and PstI, resulting in the m18/m19 AW vectors of Table C.

TABLE C

Single-stranded subclones of λ-1 and λ-14 fragments

| fragment | | resulting vectors |
| --- | --- | --- |
| pAW 1A BamHI-PstI* | (1.2 kb) | m18AW1A-1/m19AW1A-1 |
| pAW14A BamHI-PstI* | (1.2 kb) | m18AW14A-1/m19AW14A-1 |
| pAW 1A PstI-BamHI | (1.0 kb) | m18AW1A-2/m19AW1A-2 |
| pAW14A PstI-BamHI | (1.0 kb) | m18AW14A-2/m19AW14A-2 |

1.3 Determination of the Transcription Direction of the xylA Gene

The transcription direction of the xylA gene was established by means of spot blot hybridization of ss-DNA of respectively m18AW14A-1 and m19AW14A-1 with Xyl06 (SEQ ID NO: 5). It was found that ss-DNA of m19AW14A-1 (5'*PstI-BamHi 3') hybridizes with this probe. Because the sequence of Xyl06(SEQ ID NO:5) is equal to that of the non-coding strand, m19AW14A-1 contains the coding strand. On the basis thereof the transcription direction shown in FIG. 2 was determined. This direction is confirmed by the results of a primer extension experiment.

1.4 Identification of the xylA Gene

The DNA sequence of a part of the promoter region was determined by sequence analysis of pAW14 with Xyl06 as a primer (5' part of the gene). In this region a primer Xyl11(SEQ ID NO:6) with the sequence 5'- GCA TAT GAT TAA GCT GC-3' was selected, with which the DNA sequence of complementary strand of m18AW14A-1 and m18AW1A-1 was determined. The results showed that these vectors contained a DNA sequence which was substantially equal to that of Xyl06(SEQ ID NO:5), while the amino acid sequence derived from the base pair sequence was identical to the N-terminal amino acid sequence of the mature xylanase protein. Thus the cloning of at least the 5' end of the xylA gene was proved. The presence of the whole xylA gene in the vectors pAW14 and pAW1 seemed plausible on the basis of the position of the 5' end of the gene on the SalI fragments (FIG. 2) and the size of the xylA mRNA (ca. 1 kb).

1.5 Sequence Analysis

The base sequence of the xylA gene was established in two directions in both the m13AW14 and the m13AW1 subclones by means of the Sanger dideoxy procedure (Sanger et al., Proc. Natl. Acad. Sci. USA 74, 5463–5467, 1977). The sequence around the BamHI site located downstream of the PstI* site (FIG. 2) was established by sequence analysis of double-stranded pAW14 and pAW1 DNA. Compressions are cleared up by using dITP instead of dGTP. In the independent clones λ-1 and λ-14 an identical xylA sequence is established. The complete (coding) sequence of the pre(pro) xylanase gene is As shown in FIG. 1 (SEQ ID NO:7). The mature xylanase protein is preceded by a leader peptide of 27 amino acids. Between the alanine residues at the positions 16 and 17 a cleaving site is probably present for the signal peptidase. From the length of the leader peptide it can be derived that a second processing site is present in the protein. The cleaving of the band between Arg (27) and Ser (28) possibly takes place by a KEX2-like protease.

1.6 Localization of the Intron

In the xylA gene an intron of 49 or 76 bp (231–279 or 231–306, see FIG. 1 (SEQ ID NO:7)) was predicted on the basis of the presence of sequences corresponding to "donor" and "acceptor" sites of introns in Aspergilli. Definite proof of the absence of a 76 bp intron was obtained by isolation of a xylanase peptide with the sequence Tyr-Ser-Ala-Ser-Gly . . . This peptide can only be localized in the protein from position 302 (see FIG. 1 (SEQ ID NO:7)).

1.7 Determination of the 3' End of the xylA Gene

The position of the stop codon of the xylA gene (position 683 in FIG. 1 (SEQ ID NO:7)) was derived from DNA sequence data. This stop codon was confirmed, since the amino acid sequence of a peptide is identical to the C-terminal amino acid sequence derived from DNA sequence data (position 641–682 in FIG. 1 (SEQ ID NO: 7)).

1.8 Evaluation of DNA and Protein Data

On the basis of the above data the gene encoding a xylanase of *Aspergillus niger* var. *awamori* is cloned on a 5.3 kb SalI fragment. The DNA sequence of the gene, the Position of the intron and the length of the mRNA were established. The established N-terminal amino acid sequence of the mature protein was fully confirmed by the DNA sequence. On the basis of the above data it can be concluded that the xylA gene encodes a protein of 211 amino acids and that the first 27 amino acids are post-translationally removed. The amino acid sequence derived from the DNA sequence of the xylA gene demonstrates a high degree of homology with the amino acid sequence of *Bacillus pumilus* (201 amino acids) and *Bacillus circulans* (213 amino acids including signal) xylanases.

2 Expression Vectors

Three expression vectors were constructed containing the genomic xylA gene from the translation start including the xylA terminator. These vectors were derived from pAW14B (FIG. 3).

2.1 Vector pAW14S with *Aspergillus niger* var. *awamori* xylA Promoter

Figure 4:
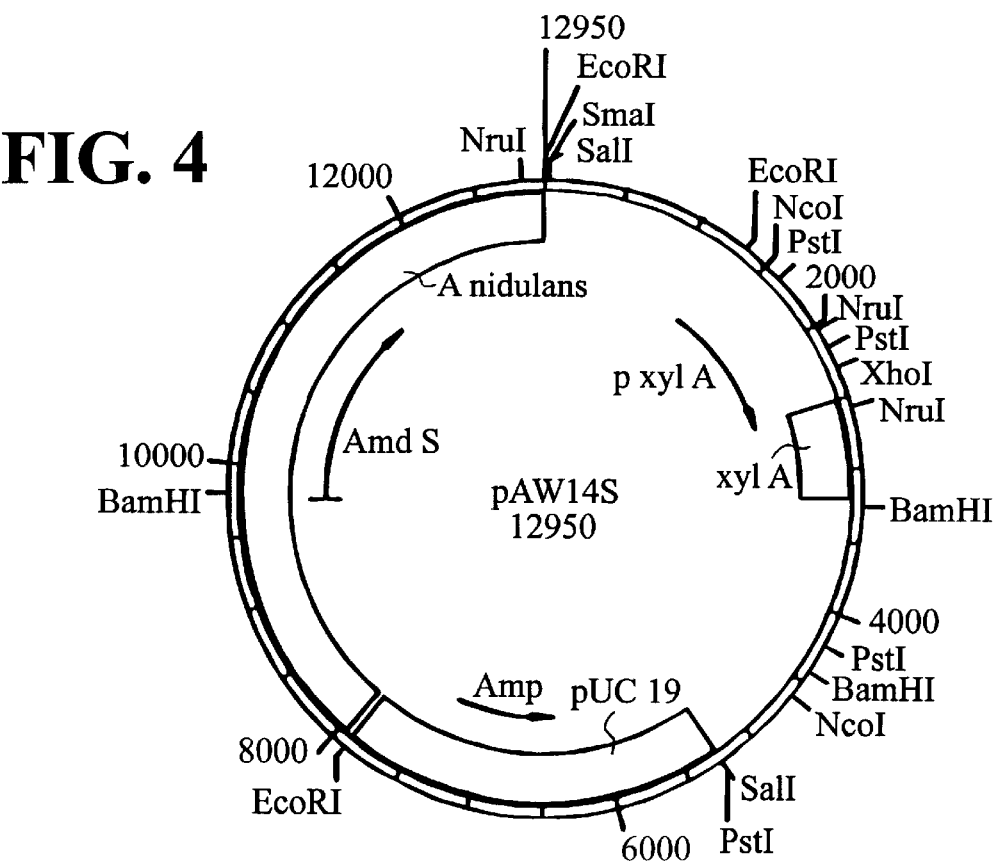
FIG. 4 shows the plasmid pAW14S containing the xylA gene with its own promoter and amds as a selection marker.

The vector pAW14S (FIG. 4) comprises a 5.3 kb chromosomal DNA fragment of *Aspergillus niger* var. *awamori* on which the xylA gene is located with its own expression signals. Further a 5.3 kb fragment of *Aspergillus nidulans* on which the acetamidase (amdS) gene is located is present on this plasmid. In pAW14S the amds and the xylA gene have the same transcription direction.

2.2 Vector RAW14S-2 with

Aspergillus nidulansgpdA Promoter

Figure 5:
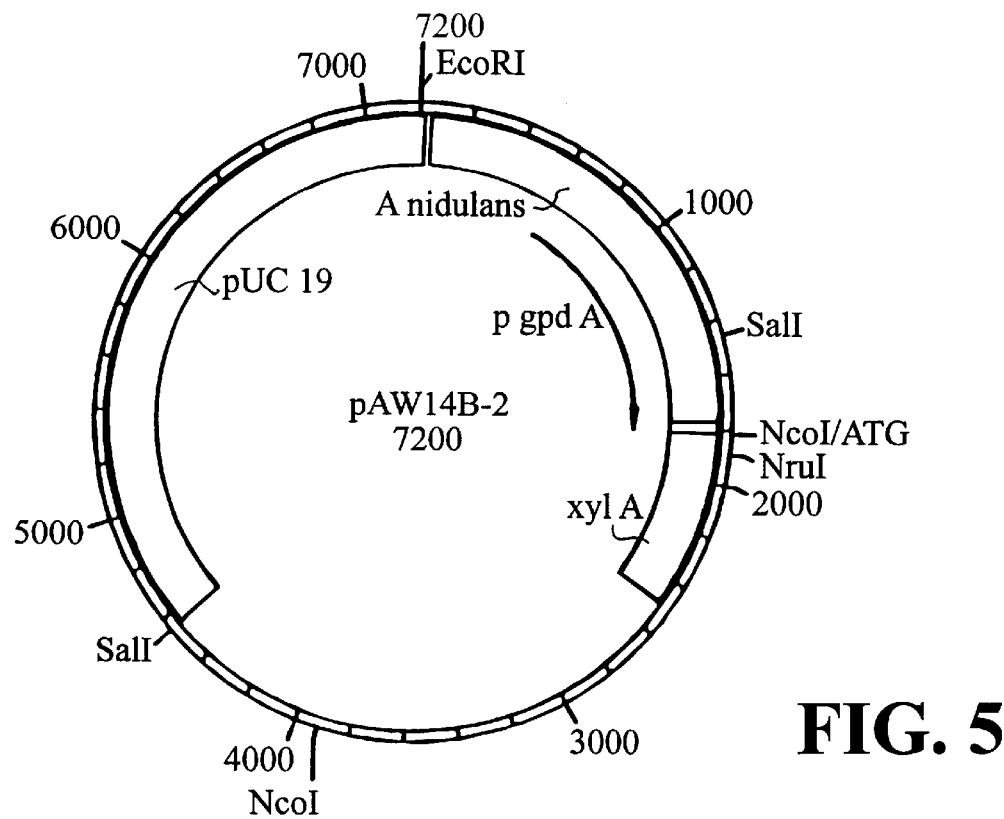
FIG. 5 shows the plasmid pAW14B-2 containing a translation fusion of the xylA gene with the *A. nidulans* gpdA promoter.

The plasmid pAW14S-2 (FIG. 6) differs from pAW14S in that the *Aspergillus niger* var. *awamori* fragment located upstream of the ATG codon of the xylA gene is replaced by the constitutive expression signals (up to the ATC triplet) of the *Aspergillus nidulans* glyceraldehyde-3-phosphate dehydrogenase (gpdA) gene. In the plasmid the amdS and the xylA gene have the same orientation. The right connection between the gpdA promoter and the ATG codon of the xylA gene was obtained by means of a synthetic DNA fragment. During the construction the plasmid pAW14B-2 in which the amdS selection marker is absent was also obtained (FIG. 5).

2.3 Vector pAW14S-3 with *Aspergillus niger* var. *niger* glaA Promoter

The vector pAW14S-3 (FIG. 7) comprises the inducible expression signals of the *Aspergillus niger* var. *niger* glucoamylase (a) gene up to the ATG codon followed by *Aspergillus niger* var. *awamori* sequences, starting at the ATG triplet of the xylA gene. In addition, this plasmid also comprises the *Aspergillus nidulans* amdS gene as a selection marker. The amdS gene and the xylA gene have the same orientation.

By means of the amdS selection marker transformants with the three above mentioned plasmids can be obtained in which the vector, and consequently also the (optionally hybrid) xylA gene, has been integrated into the genome in a large number of copies, in order to increase the production of the xylanase protein.

3 Transformation of Aspergillus

The transformation frequency of

*Aspergillus niger* var. *awamori* varied from 0.03 to 0.23 (AW) transformants per µg vector DNA. In total, this resulted in five AW14S (xylA promoter), forty AW14S-2 (gpdA promoter) and eight AW14S-3 (glaA promoter) transformants. In the continued investigation different transformants prove to have a deviating growth behaviour. One of them, AW14S #1, yielded properly sporulating (AW14S #1A) and poorly sporulating (AW14S #1B) colonies.

Transformation of *Aspergillus niger* var. *niger* N402 proceeded more efficiently than that of *Aspergillus niger* var. *awamori*. With pAW14S, pAW14S-2 and pAW14S-3 0.3, 0.3 and 1 (AB) transformants were found respectively per mg DNA. Twenty pAB14S (xylA promoter), thirty pAB14S-2 (gadA promoter) and sixteen pAB14S-3 (glaA promoter) transformants were streaked.

Co-transformation of *Aspergillus niger* var. *niger* pyrG AB4.1 with pAW14S and the *Aspergillus niger* var. *niger* pyrG gene in pAB4.1 resulted in 0.2 transformants per µg pAW14S DNA when both markers were selected. Upon the first selection for amds 2 transformants per µg DNA were found, while the frequency in the first selection for pyrG was Ca. 20 µg pAW14S DNA. It appeared that ca. 30% of the co-transformants (AB4.1–14S) possessed both markers. Six of them were analyzed further.

4 Analysis of Multicopy Transformants

4.1 Analysis of *A. niger* var. *awamori* "xylA" Transformants (AW14S) After Culturing in Medium with Xylan as an Inducer After culturing AW14S transformants with xylan as an inducer the xylanase production level obtained in the medium after 10 days was significantly higher than with the wild-type *Aspergillus niger* var. *awamori* strain. Upon storage of the media at 4° C. the enzyme is completely stable. The production levels in xylan medium are listed in the following Table D.

TABLE D

Xylanase production levels (in $10^3$ U/ml) of AW14S transformants after various culturing periods in xylan medium at 25° C.

| No. | 3 days | 10 days |
|---|---|---|
| 1 | 28 | 58 |
| 2 | 21 | 56 |
| 3 | 20 | 31 |
| 4 | 25 | 58 |
| 5 | 8 | 22 |
| wt | 5 | 13 |

4.2 Analysis of *Aspergillus niger* var. *niger* N402 "xylA" (co)transformants (AB4.1–14S) After Culturing in Medium with Xylan as an Inducer The xylanase activity was determined in xylan medium of the host strain *Aspergillus niger* var. *niger* pyrG AB4.1 and of seven AB14S-1 Pyr+ co-transformants after 48 and 72 hours of culturing respectively (see Table E). *Aspergillus niger* var. *niger* AB4.1 produces little xylanase (ca. 5000 U). For four out of seven co-transformants a high xylanase activity of ca. 30000 U was found. The other co-transformants produced somewhat less xylanase.

TABLE E

Xylanase production levels (in $10^3$ U/ml) of AB4.1-14S and AB14S transformants after different culturing periods in xylan medium at 25° C.

| AB4.1-14S | 48 hours | 72 hours |
|---|---|---|
| #1 | 36 | 36 |
| #6 | 31 | 20 |
| #12 | 29 | 23 |
| #23 | 10 | 6 |
| #42 | 15 | 10 |
| #44 | 21 | 30 |
| #45 pyrG | 22 | 18 |
| AW.wt | 3 | 7 |
| N402 | 3 | 5 |
| AB4.1 | 4 | 5 |

4.3 Characterisation of Overproduced Xylanase Enzyme

It can be derived from the highly increased xylanase activity in the medium of *Aspergillus niger* var. *awamori* and *Aspergillus niger* var. *niger* N402 multicopy "xylA" transformants that the cloned gene encodes xylanase from *Aspergillus niger* var. *awamori* and that the transformants are capable of overproduction of active xylanase. The presence of the desired product was shown by protein-chemical analysis of the medium of AW14S #1A. One dominant protein was present in the medium. The isoelectric point (pI) and the N-terminal amino acid sequence of this main component were equal to those of purified xylanase from wild-type *Aspergillus niger* var. *awamori*. The pI value found corresponded to the value calculated for the mature protein of 184 amino acids for which the composition has been derived from the DNA sequence. In baking tests the produced xylanase also proved to possess the desired properties.

4.4 Analysis of *A. niger* var. *awamori* (AW14S-2) and *A. niger* var. *niger* (AB14S-2) "gpdA" Transformants After Culturing in Rich Medium Six AW14S-2 transformants were cultured in rich medium (Table F). After two to three days a xylanase activity varying from 15000 to 20000 U was found in the medium of three transformants, while the other three produced less than half said activity. The wild-type strain produces no xylanase in rich medium. In addition, ten AB14S-2 transformants were tested. Three of them produced ca. 11000 U xylanase after 40 hours, which level was maintained for at least up to 72 hours. The other five produced less xylanase enzyme, while the activity in the medium of #21B fell from 9000 to 0 U within 24 hours.

It was shown that the production maximum of the best producing AW14S-2 and AB14S-2 transformants is in general reproducible. However, the maximum is not reached when the mycelium grows in large globules, while a higher maximum was found (19000 instead of 11000 U) in one culture of AB14S-2 #5 in duplicate. The production levels are listed in Table F.

The results show that it is possible to produce active xylanase by means of a translation fusion of the gpdA promoter and the xylA gene. However, the production bymeans of both AW14S-2 and AB14S-2 transformants regulated by the gpdA promoter in rich medium is lower than the xylanase production of "xylA" transformants in medium with xylan.

TABLE F

Xylanase production levels (in $10^3$ U/ml) of AW14S-2 and AB14S-2 transformants after various culturing periods in rich medium at 25° C.

| AW14S-2 | 24 hours | 48 hours | 72 hours | | |
|---|---|---|---|---|---|
| #1 | <1 | 3 | >3 | | |
| #4 | 1 | 2 | 2 | | |
| #10 | 11 | 15 | 13 | | |
| #22 Δ | * | 4 | 20 | 20 | |
| #36 | | 3 | 7 | 7 | |
| #39 | * | 10 | 16 | 12 | |

| AB14S-2 | 24 hours | 40 hours | 48 hours | 66 hours | 72 hours |
|---|---|---|---|---|---|
| #2 | | 4 | 4 | 9 | |
| #5 Δ | 3 | 11 | 11 | 11 | 12 |
| double | | 15 | 16 | 19 | |
| #7 Δ | 1 | 5 | 5 | 5 | 4 |
| #8 | | 4 | 3 | 4 | |
| #11 | <1 | <1 | 1 | 1 | 0 |
| #14 | | 2 | 2 | 3 | |
| #16 Δ | 3 | 10 | 10 | 11 | 10 |
| #17 Δ | 3 | 10 | 11 | 10 | 10 |
| #18 | 1 | 5 | 8 | 10 | 8 |
| #21B | | 4 | 8 | 9 | 00 |

Δ maxima, found when repeating the culture; a culture of AB14S-2 #5 in duplicate gave a higher maximum. In rich medium *A. niger* var. *awamori* and transformant AW14S #4 produce no xylanase.

4.5 Analysis of *Aspergillus niger* var. *awamori* (AW14S-3 and *Aspergillus niger* var. *niger* (AB14S-3) "glaA" transformants After Culturing in Medium with Starch as an Inducer Some AW14S-3 transformants and the *Aspergillus niger* var. *awamori* wild-type strain were cultured in starch medium (Table G). A xylanase activity of 67000 U/ml was found in the medium of one transformant after 90 hours of culturing, while two other transformants produced up to 36000 U/ml. The production maximum of six analyzed AB14S-3 transformants lies one day earlier than of AW14S-3 transformants. An activity of 51000 U/ml was found in the medium of one transformant two others produced about 43000 U/ml, after 63 hours of culturing. The results show that the translation fusion between the glaA promoter and the xylA gene is effected in the right manner. Both AW14S-3 and AB14S-3 transformants produce substantially as much xylanase enzyme in starch medium, regulated by the glaA promoter, as "xylA" transformants in medium with xylan.

TABLE G

Xylanase production levels (in $10^3$ U/ml) of "glaA" transformants AW14S-3 and AB14S-3 after different culturing periods (hours) in starch medium at 25° C.

| | 40 hour | 63 hour | 90 hour |
|---|---|---|---|
| AW14S-3 | | | |
| #1 | | 37 | 37 |
| #2 | 4 | 14 | 15 |
| #4 | 8 | 31 | 36 |
| #7 | 16 | 49 | 67 |
| AB14S-3 | | | |
| #4 | 23 | 51 | 29 |
| #5 | 19 | 37 | 21 |
| #7 | 23 | 44 | 18 |
| #8 | 17 | 28 | 32 |
| #14 | 21 | 43 | 19 |
| #16 | 6 | 21 | 10 |

4.6 Analysis of "xylA" Transformants After Culturing in Medium with Wheat Bran

It is apparent from the results (Tables H and I) that the production level observed for AW14S #4 when culturing in medium with wheat bran is higher than that in xylan medium. A high production level was obtained with AB4.1–14S (#1 and #44) and AB14S (#5 and #14) transformants. The xylanase activity obtained with said transformants was determined as being as high as 140000 U/ml. This means a considerable increase with respect to the production in xylan medium (30000 U/ml). It further appears that the production level of these *Aspergillus niger* var. *niger* transformants is also maintained upon prolonging the culturing period, as was found earlier with *Aspergillus niger* var. *awamori* "xylA" transformants in xylan medium.

4.7 Analysis of "gpdA" Transformants After Culturing in Medium with Wheat Bran

AW14S-2 #22 and 139 produced up to 28000 U/ml xylanase. The AB14S-2 #5 and #17 transformants produced relatively little xylanase (activity up to 15000 U/ml) with wheat bran, as was also found in rich medium. The production levels are listed in Tables H and I.

4.8 Analysis of "glaA" Transformants After Culturing in Medium with Wheat Bran

The tested AW14S-3 (#1 and #7) transformants produced up to 25000 and 45000 U/ml xylanase respectively in medium with wheat bran, which for both is ca. 60–65% of the values found in starch (Table I). With AB14S-3 (#4 and #14) transformants, however, a higher production was determined with wheat bran than in starch. The production levels determined are 1.5 times higher than in starch. A production of 72000 U/ml was obtainer with AB14S-3. A value of 66000 U/ml was found with AB14S-3 #14 (Table I).

TABLE H

Xylanase production levels (in $10^3$ U/ml) of some AW and AB "xylA" and "gpdA" transformants after various culturing periods in medium containing bran at 25° C.

| | | 40 hours | 63 hours | 4 days | 7 days | 12 days |
|---|---|---|---|---|---|---|
| Aw wt | | | 1 | 2 | 16 | 17 |
| AW14S | #4 | 8 | 20 | 27 | 61 | 80 |
| AB14S | #14 | 6 | 74 | 114 | 126 | 122 |
| AB4.1-14S | #1 | 17 | 87 | 123 | 135 | 145 |
| AW14S-2 | #22 | 17 | 22 | 22 | 34 | 33 |
| AW14S-2 | #39 | 18 | 22 | 21 | 24 | 20 |

TABLE H-continued

Xylanase production levels (in $10^3$ U/ml) of some AW and AB "xylA" and "gpdA" transformants after various culturing periods in medium containing bran at 25° C.

|  |  | 40 hours | 63 hours | 4 days | 7 days | 12 days |
|---|---|---|---|---|---|---|
| AB14S-2 | #5 | 13 | 15 | 11 | 8 | 8 |
| AB14S-2 | #17 | 9 | 13 | 11 | 7 | 7 |

TABLE I

Xylanase production levels (in $10^3$ U/ml) of AW and AB transformants after various culturing periods in wheat bran medium at 25° C.

|  | 2 days | 3 days | 4 days | 7 days | 9 days | 14 days |
|---|---|---|---|---|---|---|
| AW wt |  |  | 2 | 8 | 10 | 11 |
| N402 wt |  |  | 4 | 2 | 1 |  |
| AW14S |  |  |  |  |  |  |
| #1A |  |  | 18 | 39 | 51 |  |
| #4 |  |  | 34 | 67 | 76 | 76 |
| AB14S |  |  |  |  |  |  |
| #5 | 45 | 80 | 100 | 111 | 109 | 118 |
| #14 | 45 | 77 | 79 | 100 | 92 |  |
| AB4.1-14S |  |  |  |  |  |  |
| #1 |  | 95 |  | 90 | 73 |  |
| #44 |  |  | 121 | 144 | 148 | 145 |
| AW14S-2 |  |  |  |  |  |  |
| #22 |  |  | 22 | 29 | 29 |  |
| #39 |  |  | 17 | 26 | 28 |  |
| AB14S-2 |  |  |  |  |  |  |
| #5 | 15 | 14 |  | 12 | — |  |
| #17 | 10 | 11 |  | 9 | — |  |
| AW14S-3 |  |  |  |  |  |  |
| #1 |  |  | 18 | 26 | 25 |  |
| #7 |  |  | 37 | 45 | 45 | 41 |
| AB14S-3 |  |  |  |  |  |  |
| #4 | 72 | 54 | 44 | 23 | 17 |  |
| #14 | 64 | 66 | 69 | 55 | 55 | 55 |

4.9 Evaluation of the Results

The results as summarized in Table A show that multicopy transformants of *Aspergillus niger* var. *awamori* (AW14S) and *Aspergillus niger* var. *niger* (AB14S) are capable of overproduction of active xylanase after induction of their own xylA promoter with respectively xylan and wheat bran as an inducer. Expression of xylanase by multicopy transformants of *Aspergillus niger* var. *awamori* and *Aspergillus niger* var. *niger* N402 with the xylA gene under control of the gpdA promoter (respectively AW14S-2 and AB14S-2) and the glaA promoter (respectively AW14S-3 and AB14S-3) indicates that xylanase can be produced in a wide range of substrates. Variability in the productivities between the different transformants may be the result of differences in copy number and/or of differences in the site of integration into the genome. Of course, the testing conditions may also have a significant effect on the xylanase production. For optimization of the production, however, preference will be given to strains showing a relatively high productivity.

5 Materials and Methods 5.1 Strains and Plasmids

In the experiments the following strains and plasmids were used:

*Aspergillus niger* var. *awamori* strain CBS 115.52, ATCC11358;

*Aspergillus niger* var. *niger* strain N402, a cspA1 (short conidiophores) mutant of *Aspergillus niger* var. *niger* ATCC9029, CBS 120.49;

*Aspergillus niger* var. *niger* AB4.1, a pyrG mutant of *Aspergillus niger* var. *niger* N402, described by Van Hartingsveldt et al., Mol.Gen.Genet. 206, 71–75, 1987;

*Escherichia coli* strain JM109 (for plasmid isolation, see Yanisch-Perron et al., Gene 33, 103–119, 1985);

*Escherichia coli* strain NM539 (for construction and amplification of the lambda-gene library);

plasmid pGW325, containing the amds gene of *Aspergillus nidulans* see K. Wernars, "DNA-mediated transformation of the filamentous fungus *Aspergillus nidulans*", Thesis, Agricultural University of Wageningen, 1986;

plasmid pAB4.1, containing the p=gene of *Aspergillus niger* var. *niger* N402, see Van Hartingsveldt et al., Mol. Gen-.Genet. 206,71–75, 1987;

plasmid pAN52–1, described by Punt at al., Gene 56, 117–124, 1987; and plasmid pAN52–6, described by P. J. Punt, J. Biotechn., in press;

vector λ-EMBL3 (for construction of an *Aspergillus niger* var. *awamori* gene library), obtainable from Promega Biotec.

An *Escherichia coli* JM109 strain containing the plasmid pAW14B was deposited with the Centraalbureau voor Schimmel-cultures (CBS) of Baarn, The Netherlands, under number CBS 237.90, on May 31, 1990.

5.2 Aspergillus Transformation

*Aspergillus niger* var. *awamori* protoplasts were made from mycelium by means of Novozym 234 (NOVO). The yield of protoplasts was 1–5×$10^7$/g mycelium and the viability was 3–8%. Per transformation 3–8×$10^5$ viable protoplasts were incubated with 5, 10 or 20 mg, plasmid DNA that had twice undergone CsCl purification. Transformed protoplasts were plated on osmotically stabilized selection plates (acetamide as a nitrogen source) and incubated at 25° C. After 6–10 days colonies were visible. Transformation of *Aspergillus niger* var. *niger* N402 and *A. niger* var. *niger* AB4.1 respectively was in principle carried out as described above. In the case of *Aspergillus niger* var. *niger* pyrG AB4.1, however, uridine was added to the medium. In the co-transformation of *A. niger* var. *niger* AB4.1, pAW14S and pAB4.1 DNA were mixed in a weight ratio of 4:1; transformants were selected on acetamide plates with uridine (amdS selection), without uridine (amdS and pyrG selection) and on minimal medium plates with nitrate (pyrG selection) respectively. After 4–5 days colonies became visible. (Co-)transformants were streaked twice onto acetamide plates. In order to obtain large amounts of spores, spores from the second streak were streaked through onto plates with rich medium and incubated for 5–6 days at 25–28° C. The resulting spores were stored as a suspension ($10^8$–$10^9$ spores/ml) or adsorbed to silica gel so that the spores can be stored for a long time.

5.3 Construction of *A. niger* var. *awamori* Gene Library

Chromosomal DNA was isolated from myceliun of *Aspergillus niger* var. *awamori*. The high molecular DNA was partially cleaved with Sau3AI, followed by isolation of fragments of 13–17 kb After electrophoresis on a 0.4% agarose gel. Of these fragments 0.4 mg were ligated with 1.2 mg λ-DML3 DNA which was cleaved with BamHI and EcoRI. The ligation mixture was provided with phage coats by means of an in vitro packing system (Amersham). By transduction to *E. Coli* NM539 a gene library of ca. 154 000 plaques was obtained. These presented ca. 75×the genome of *A. niger* var. *awamori*. 65000 Plaques were transferred to nitrocellulose filters (in plicate).

5.4 Hybridisation Experiments

Southern blot analysis: hybridisation of digests of chromosomal A. niger var. awamori DNA with radioactively labelled oligonucleotide mixtures Xyl04 and Xyl06 (SEQ ID NO:s 3 and 5) (47 mers) was carried out in 6×SSC at respectively 68° C., 62° C. and 56° C.; for Xyl01 and Xyl05 (SEQ ID NO:s 2 and 4, respectively) (23 mers) a hybridization temperature of 41° C. was used. The selected hybridization temperature was at least 5° C. below the calculated melting temperature. Blots were washed at the hybridization temperature with 5×and 3×SSC respectively. Hybridization was carried out at 68° C. in 6×SSC, while the last washing steps were carried out at the same temperature with 2× and 0.4×SSC respectively.

Northern blot analysis: total, non-induced RNA of A. niger var. awamori was isolated from mycelium of rich medium cultures (after 3 days of culturing at 25° C.). Induced RNA originated from cultures in which 1% xylan or 4% wheat bran was used as an inducer. Mycelium was collected from the last-mentioned cultures after different culturing periods. After 3 and 6 days respectively mycelium was isolated from medium with wheat bran. Mycelium of xylan medium was collected after 6 and 11 days of culturing respectively. Hybridization conditions were equal to those in the Southern blot analysis.

5.5 Culturing Conditions

Media: xylan medium contains 1% xylan, 0.67% yeast extract with amino acids (Difco) and 0.1% cas. amino acids. Medium with wheat bran consists of 4 g wheat bran in 50 ml mains water, to which 50 ml of a salt solution (pH 5.0) is added up to a final concentration of 0.5% (NH4)2SO4, 0.15% KH2PO4, 0.025% MgSO4 AND 0.025% KCl. Rich medium for expression tests is minimal medium (0.05% MgSO4, 0.6% NaNO3, 0.05% KCl, 0.15% KH2PO4 and trace elements), with 1% glucose, 0.2% trypticase (BBL), 0.5% yeast extract, 0.1% cas. amino acids and vitamin. Starch medium contains 5% starch and 0.1% glucose in minimal medium. Media were sterilized for 30 min. at 120° C. Medium (100 ml in a 500 ml flask) was inoculated with 2×105 spores/ml, followed by culturing in an air incubator (300 rpm) at 25° C. for different periods. Cultures with wheat bran as an inducer (Table I) were inoculated with 4×105 spores/ml.

5.6 Determination of Xylanase Activity in Medium of Aspergillus Cultures

The xylanase activity was established by determining the formation of reducing sugars. Procedure: a (diluted) medium sample was added to 125 μl 2% xylan (Sigma) in 0.5 M Na acetate pH 5.0 at 40° C., followed by incubation of the reaction mixture for 30 min. at 40° C. The reaction was immediately stopped with 0.5 ml 2-hydroxy-3,5-dinitrobenzoic acid (DNS) reagent, followed by supplementing the volume with water up to 1 ml. The reaction mixture was heated for 5 min. at 100° C. and cooled to room temperature. The OD was determined at 534 nm against a blank. The xylanase activity determination of one sample was carried out at least twice. 0.5 M Na acetate pH 5.0 was used for diluting the media

5.7 Selection of Transformants

In the analysis of the many transformants the host strains and ca. 6 transformants from one series were cultured in rich or selective medium, followed by determination of the xylanase production level. Two transformants from each series, with the highest xylanase production, were analyzed again in the same medium. In addition, the production level of these transformants was determined in medium with wheat bran.

Figure 6:
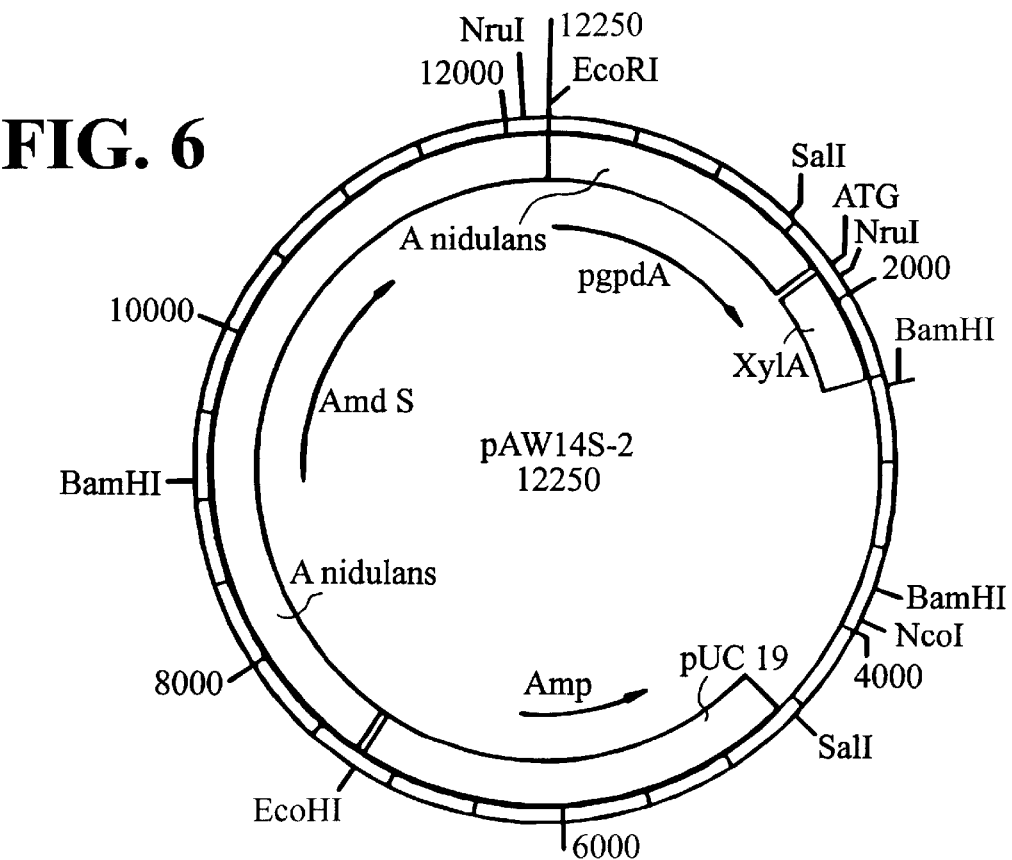
FIG. 6 shows the plasmid pAW14S-2 containing a translation fusion of the xylA gene with the *Aspergillus nidulans* gpdA promoter and amdS as a selection marker.
Figure 7:
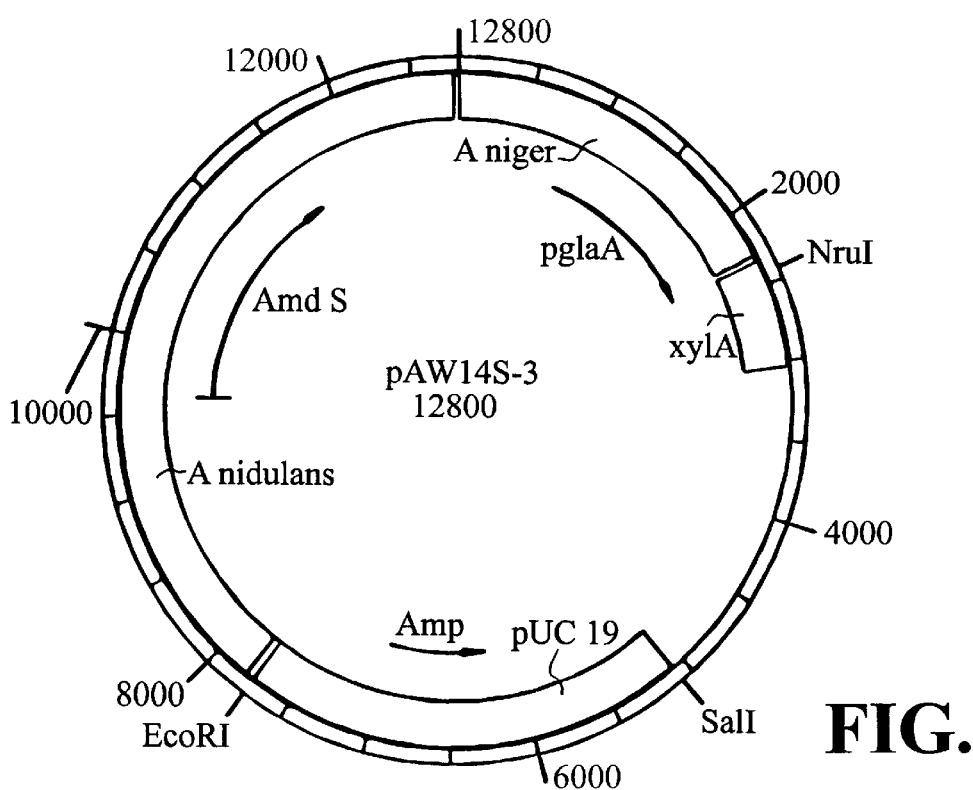
FIG. 7 shows the plasmid pAW14S-3 containing a translation fusion of the xylA gene with the *Aspergillus niger* glaA promoter and amds as a selection marker.

5.8 Construction of Expression Vectors pAW14S (with the Aspergillus niger var. niger xylA promoter): the expression vector pAW14S (FIG. 4) was constructed by insertion of a 5.0 kb EcoRI fragment of plasmid pGW325, on which the Aspergillus nidulans amdS gene is located, into the EcoRI site of the polylinker of pAW14B (FIG. 3). In pAW14S the amdS and xylA gene have the same transcription direction.

pAW14S-2 (with the A. nidulans gpdA promoter): the linear 1.8 kb StuI-NcoI fragment of pAN52-1, on which the A. nidulans gpdA promoter (up to the ATG triplet) is located, was ligated with the 7.2 kb NcoI*-SmaI fragment of pAW14B, obtained by partial digestion with NcoI and complete digestion with SmaI. Transformation of E. coli JM109 resulted in isolation of plasmid pAW14B-1 (9.0 kb1). The 7.2 kb NruI*-NcoI* fragment of pAW14B-1, obtained by partial digestion with NcoI and complete digestion with NruI, was ligated with a synthetic fragment (79 bp, nucleotides Nos. 1–78 of the coding strand and nucleotides Nos. 4–78 of the template strand), consisting of xylA sequences from the ATG triplet, resulting in pAW14B-2 (FIG. 5). The 5.0 kb EcoRI fragment of pGW325 (Aspergillus nidulans amdS gene) was introduced into the unique EcoRI site of pAW14B-2, resulting in pAW14S-2 (FIG. 6). The amdS and the xylA gene have the same orientation in this plasmid. The connection of the gpdA promoter to the ATG codon of the xylA gene as well as the sequence of the synthetic fragment was verified by means of DNA sequence analysis.

pAW14S-3 (with the A. niger var. niger N402 glaA promoter): pAN52-6 was partially cleaved with XmnI (3 sites). The linear 7.5 kb fragment, on which the A. niger var. niger N402 glaA promoter is located, was isolated. After cleaving this fragment with BssHII a 7.35 kb BssHII-XmnI fragment was ligated with a synthetic DNA fragment (ca. 150 bp) containing the 3' end of the alaA promoter up to the ATG triplet, followed by the xylA gene from the ATG triplet to the NruI site located in the gene with a BssHII terminus behind that. The plasmid pAN52–6.URL that was thus obtained was cleaved with NcoI and with NruI, after filling in the NcoI site. The DNA sequence of the synthetic fragment in pAN52–6.URL was checked. The glaA promoter was placed before the xylA gene by ligation of the 2.5 kb "filled NcoI"-NruI fragment from pAN52–6.URL with the ca. 10 kb NruI fragment of pAW14S. Insertion of this fragment in the right orientation resulted in pAW14S-3 (FIG. 7).

EXAMPLE II

Baking Tests

The bread improving activity of the xylanase, obtained after isolation from fermentation broth, was tested by measuring the volume increase of Belgian bread rolls baked after addition of increasing amounts of enzyme and dough. The xylanase was isolated as follows.

Aspergillus niger var. awamori transformant AW14S.1A was cultured for 7 days on medium with 4% wheat bran in a fermentor having an operating volume of 8 liter. The xylanase production was ca. 85000 U/ml. The fungal cells were removed by a filtration over a cloth. Ammonium sulphate was then added to 6 liters of filtrate, with stirring, up to 50% by weight. The precipitate was centrifuged in a Sorvall GSA rotor at 10000 g for 20 minutes. The pellet was suspended in 500 ml aqua dest. and then centrifuged again at 10000 g. The supernatant was then concentrated by ultrafiltration by means of an Amicon PM10 ultrafiltration membrane up to a volume of 60 ml. In order to remove the ammonium sulphate the ultrafiltration was repeated twice after dilution with aqua dest. to 300 and 600 ml respectively. The finally obtained material that was present in a volume of 50 ml was then freeze dried. The yield was 4.8 g with a specific activity of 60000 U/mg (56% overall). For use in baking tests the xylanase was mixed with starch to a concentration of 240 U/mg.

600 ml Water, 20 g salt, 20 g sugar (sucrose), 50 g yeast (Koningsgist from Gist Brocades) and 0, 50, 100 or 200 mg/kg xylanase (240 U/mg) were added to 1000 g wheat flour Banket Extra (from Wessanen). The dough species were kneaded in an Eberhardt kneader for ten minutes at a dough temperature of 24° C. After 20 minutes of fermentation at 28° C. the dough was beaten, divided into small dough portions of ca. 50 g and once again fermented in a raising cabinet for 60 minutes at 35° C. to 38° C. The dough portions were then baked at 230° C. for 20 minutes. The specific volumes (in ml/g) were determined by dividing the volume (in ml), determined by means of the seed displacement method, by the weight (in g).

For an average of 10 bread rolls the following results were found:

| enzyme level | 0 | 50 ppm | 100 ppm | 200 ppm |
|---|---|---|---|---|
| specific volume | 6.8 | 7.9 | 8.7 | 8.9 |

The same trends can be established if, moreover, other bread improving ingredients such as vitamin C, fat, emulsifiers and α-amylase are added. Other properties such as dough processing and crumb structure are also positively affected by adding the xylanase enzyme.

EXAMPLE III

Production of *Aspergillus niger* var. *awamori* Xylanase by *Saccharomyces cerevisiae*

As an example of the heterologous production of *Aspergillus niger* var. *awamori* xylanase by microorganisms, expression vectors were constructed for the expression of the xylanase in *Saccharomyces cerevisiae* regulated by the inducible GAL7 promoter (Nogi and Fukasawa, 1983). The GAL7 promoter effects production of enzyme under inducing conditions: growth on medium with galactose as the only carbon source (Hopper and Rowe, 1978). The use of this promoter for induced production of heterologous proteins has already been described (Tajima et al., 1985). The fungal gene encoding xylanase was first rendered suitable for expression in *Saccharomyces cerevisiae* by removing the intron (non-coding sequence) by means of a synthetic DNA fragment. The same technique has been used to provide a correct connection of the xylanase gene to the *Saccharomyces cerevisiae* GAL7 promoter. Optionally, a *Saccharomyces cerevisiae* signal sequence, the invertase signal sequence, was also introduced to realize the secretion of the fungal enzyme xylanase by the yeast *Saccharomyces cerevisiae*. Autonomously replicating vectors as well as (multicopy) integrating vectors have been used in the production of the *Aspergillus niger* var. *awamori* xylanase by the yeast *Saccharomyces cerevisiae*. All cloning procedures were carried out in *E. coli* strain JM109 (Yanisch-Perron et al., 1985) and all methods and techniques according to Maniatis et al. (1982).

Construction of Vector pUR2901

Figure 9:
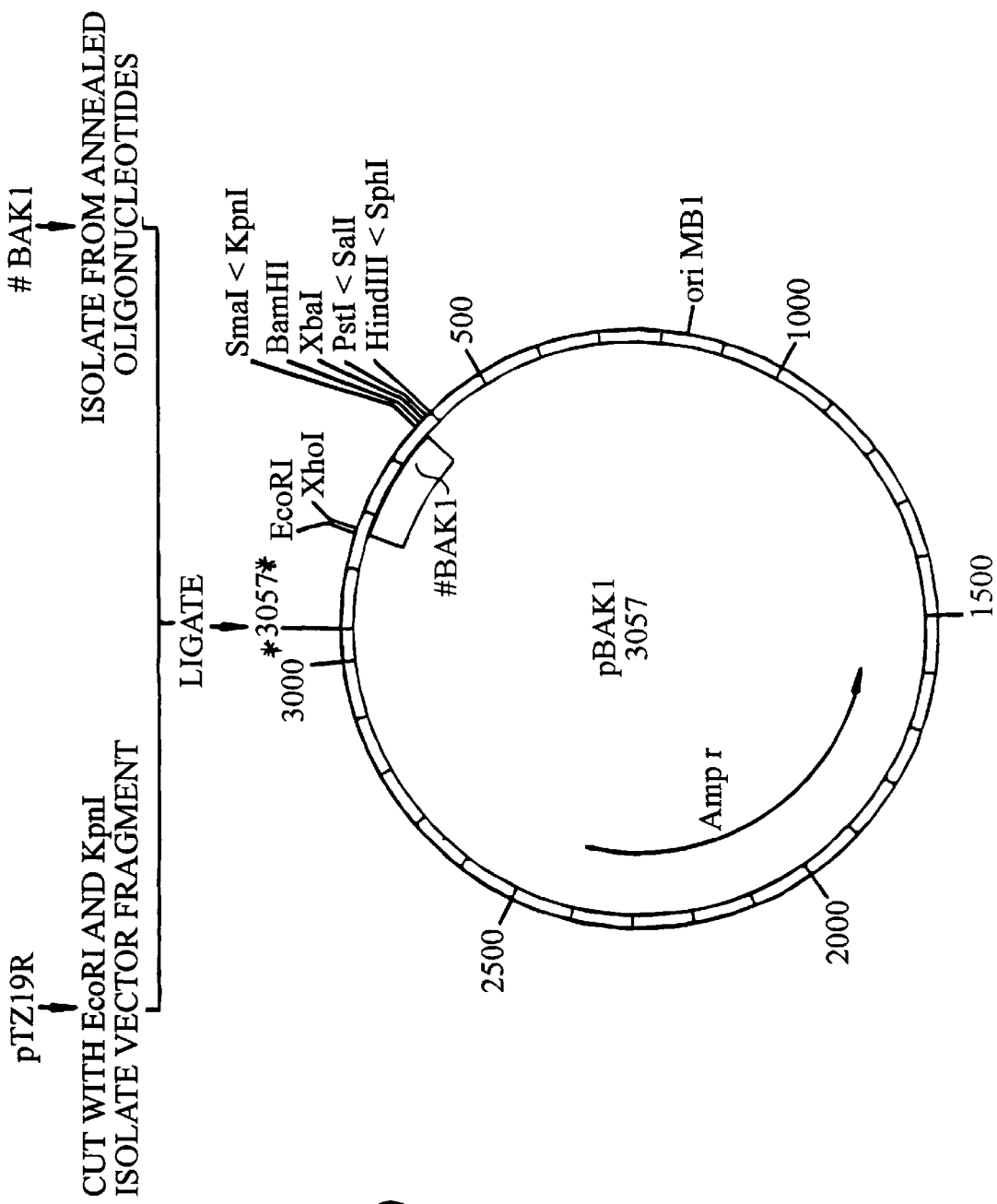
FIG. 9 (SEQ ID NO:s 10 and 13–27) is a schemaic representation of the construction of the plasmid pBAK1.

The first intermediate construction was directed at the correct removal of the intron from the xylanase gene, i.e. without changing or disturbing the coding sequence. The synthetic DNA oligonucleotides shown in FIG. 8 (BAK 02, 03, 04, 05, 06, 07, 08, 09, 10, 23 and 24 (SEQ NO ID NO:s 34–37,43,42,41,40,39,33 and 38, respectively)) were annealed and ligated together resulting in the fragment BAK1(SEQ ID NO:9). The fragment BAK1 measures 205 bp and comprises the SacI—KpnI xylanase fragment (bp 185-bp 427) from which the intron has been removed. The synthetic DNA oligonucleotides have been designed in such a manner that upon removal of the intron a correct connection to the fragments has been made so that the open reading frame (encoding xylanase) is not disturbed. In order to simplify the continued construction the SacI site was changed to an XhoI site. On the 5' side the fragment was provided with an EcoRI site. The ligation mixture was digested with the restriction enzymes KpnI and EcoRI and the correct 205 bp fragment was isolated by means of agarose gel electrophoresis for the separation of the fragment and gel elution for the isolation of the fragment from the agarose gel. The KpnI-EcoRI BAX1 fragment was cloned into the KpnI and the EcoRI site of vector pTZ19R (obtained from Pharmacia) resulting in pBAK1 (see FIG. 9). The inserted fragment in the constructed plasmid pBAK1 was checked by means of sequence analysis.

Figure 11A:
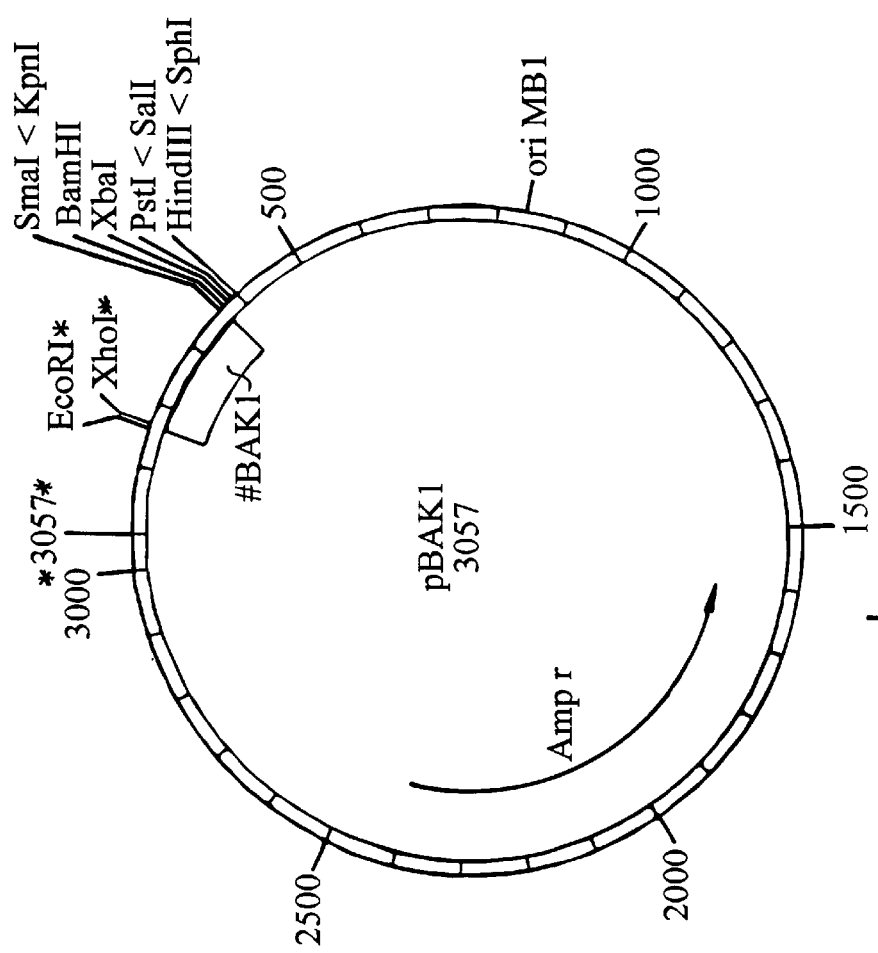
FIGS. 11A and 11B are a schematic representation of the construction of the plasmid pBAK21.
Figure 11B:
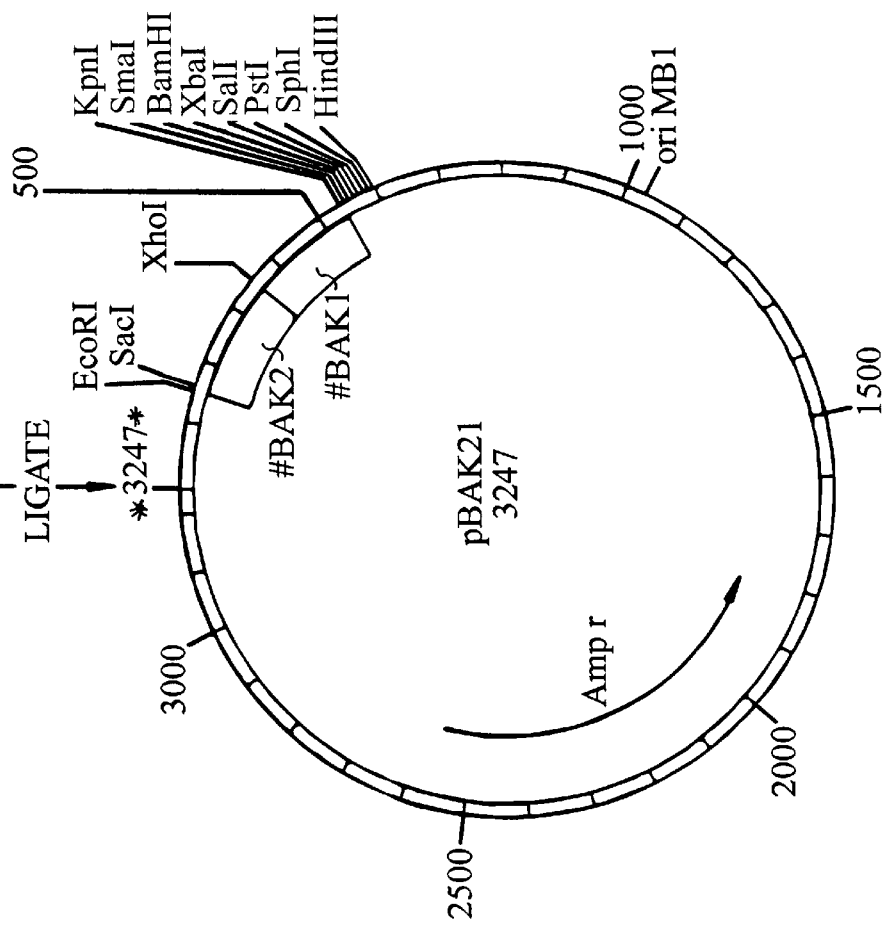

The continued constructions were directed at the realization of a correct connection of the *Aspergillus niger* var. *awamori* xylanase gene to the *Saccharomyces cerevisiae* GAL7 promoter. For this purpose the synthetic DNA oligonucleotides shown in FIG. 10 (BAK13, 14, 15, 18, 19, 20, 21, 25, 26, 27 and 28 (SEQ ID NO:s 17–19, 25,24, 23,22, 21,20,26 and 21, 39 respectively) were annealed and ligated resulting in fragment BAK2 (SEQ ID NO:10). Fragment BAK2 measures 202 bp and comprises the synetic transition from the SacI site of the GAL7 promoter via the invertase signal sequence to the mature xylanase gene up to the SacI (bp 185) site. In order to simplify the continued construction the SacI site was changed to an XhoI site, in a manner identical to the one used in the construction of pBAK1. An additional EcoRI site was provided on the 5' side of the fragment. The ligation mixture was digested with EcoRI and XhoI and the correct 202 bp BAK2 fragment was isolated. Plasmid pRAK1 was digested with EcoRI and XhoI and the BAK2 (SEQ ID NO:10) fragment with the same termini was cloned in the vector fragments, resulting in plasmid pBAK21 (see FIG. 11). The inserted BAK2 (SEQ ID NO:10) fragment was checked by means of sequence analysis. In plasmid pBAK21 the connection of fragments BAK1 and BAK2 (SEQ ID NO:s 9 and 10, respectively) to the XhoI site was effected in such a manner that the open reading frame encoding xylanase was correctly restored. Plasmid pBAK21 therefore contains the *Saccharomyces cerevisiae* GAL7 promoter transition from the SacI site, the *Saccharomyces cerevisiae* invertase signal sequence (including an ATG start codon) and the *Aspergillus niger* var. *awamori* xylanase (encoding mature xylanase) from which the fungal intron (non-coding sequence) has been correctly removed up to the KpnI site (the 5' part of the xylanase gene).

Figure 12A:
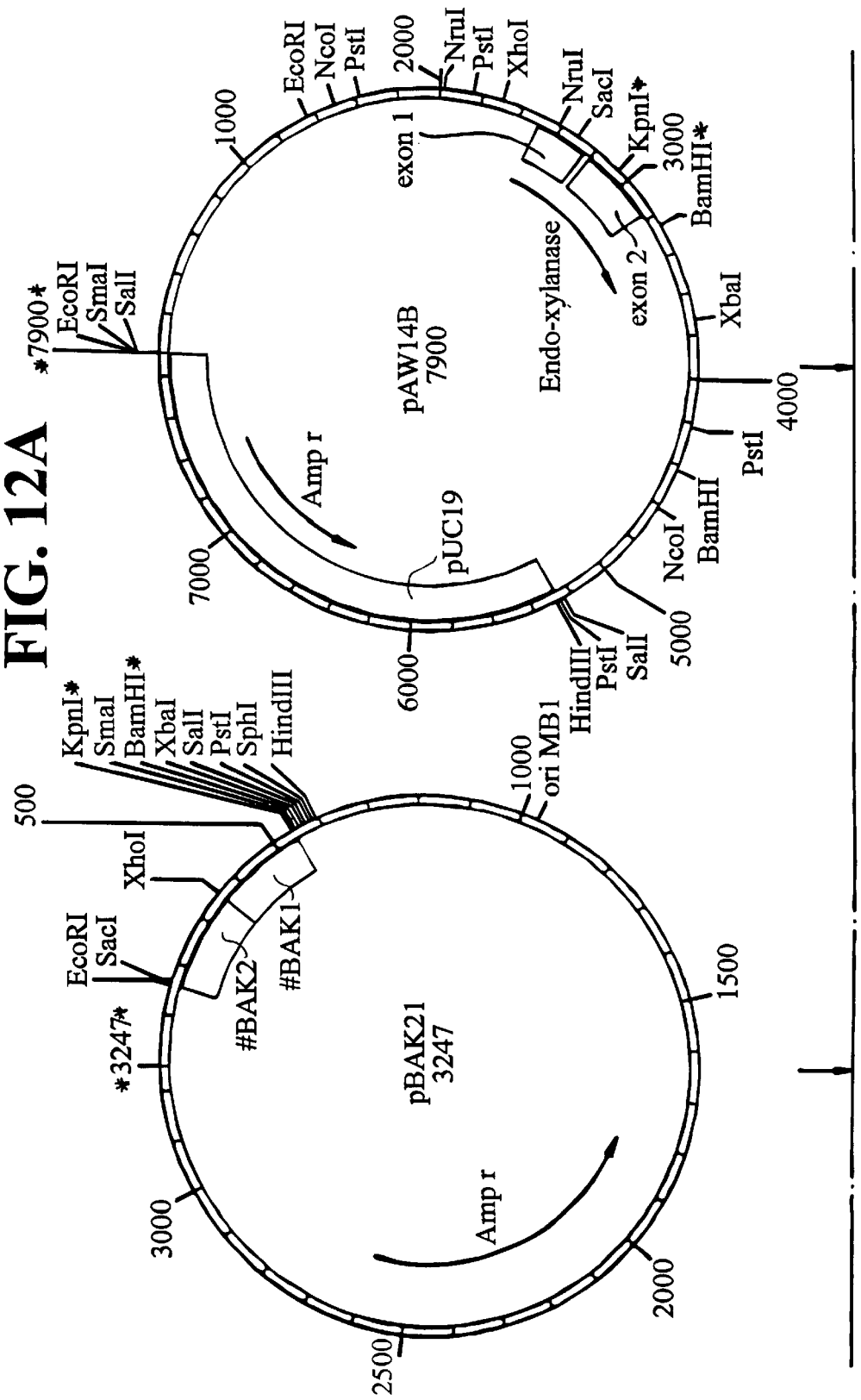
FIGS. 12A and 12B are a schematic representation of the construction of the plasmid pUR2901.
Figure 12B:
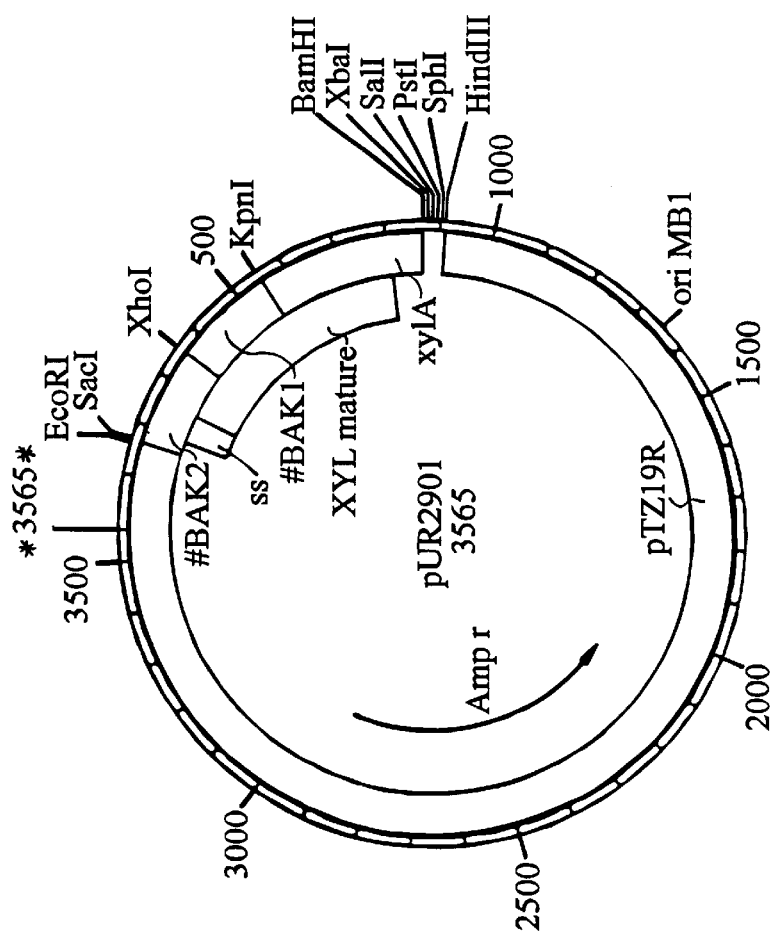

Plasmid pAW14B was digested with KpnI and BamHI and the 327 bp KpnI-BamHI fragment, containing the 3' part of the xylanase gene, was isolated. Plasmid pBAK21 was also digested with KpnI and BamHI and the vector fragment was isolated. The isolated 327 bp fragment and the vector fragment were ligated together resulting in plasmid pUR2901 (see FIG. 12). Plasmid pUR2901 was checked by means of restriction enzyme analysis. Plasmid pUR2901 contains the *S. cerevisiae* GAL7 promoter fusion site at the SacI site, the *S. cerevisiae* invertase signal sequence (including an ATG start codon), and the complete *Aspergil-* lus niger var. awamori xylanase gene (encoding mature xylanase) from which the fungal intron (non-coding sequence) has correctly been removed.

Construction of the S. cerevisiae Expression Vector pUR2904

Figure 13A:
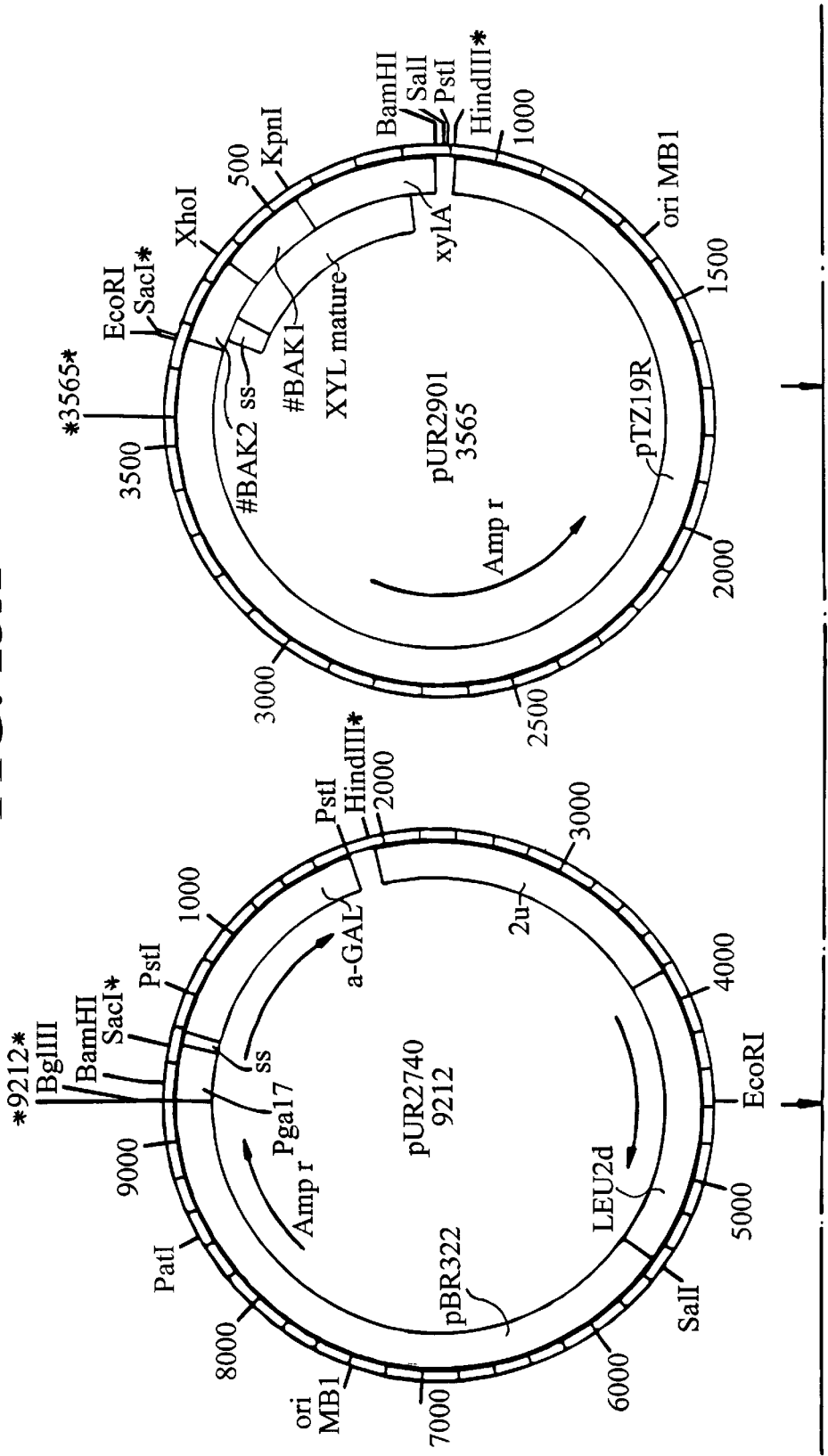
FIGS. 13A and 13B are a schematic representation of the construction of the plasmid pUR2904.
Figure 13B:
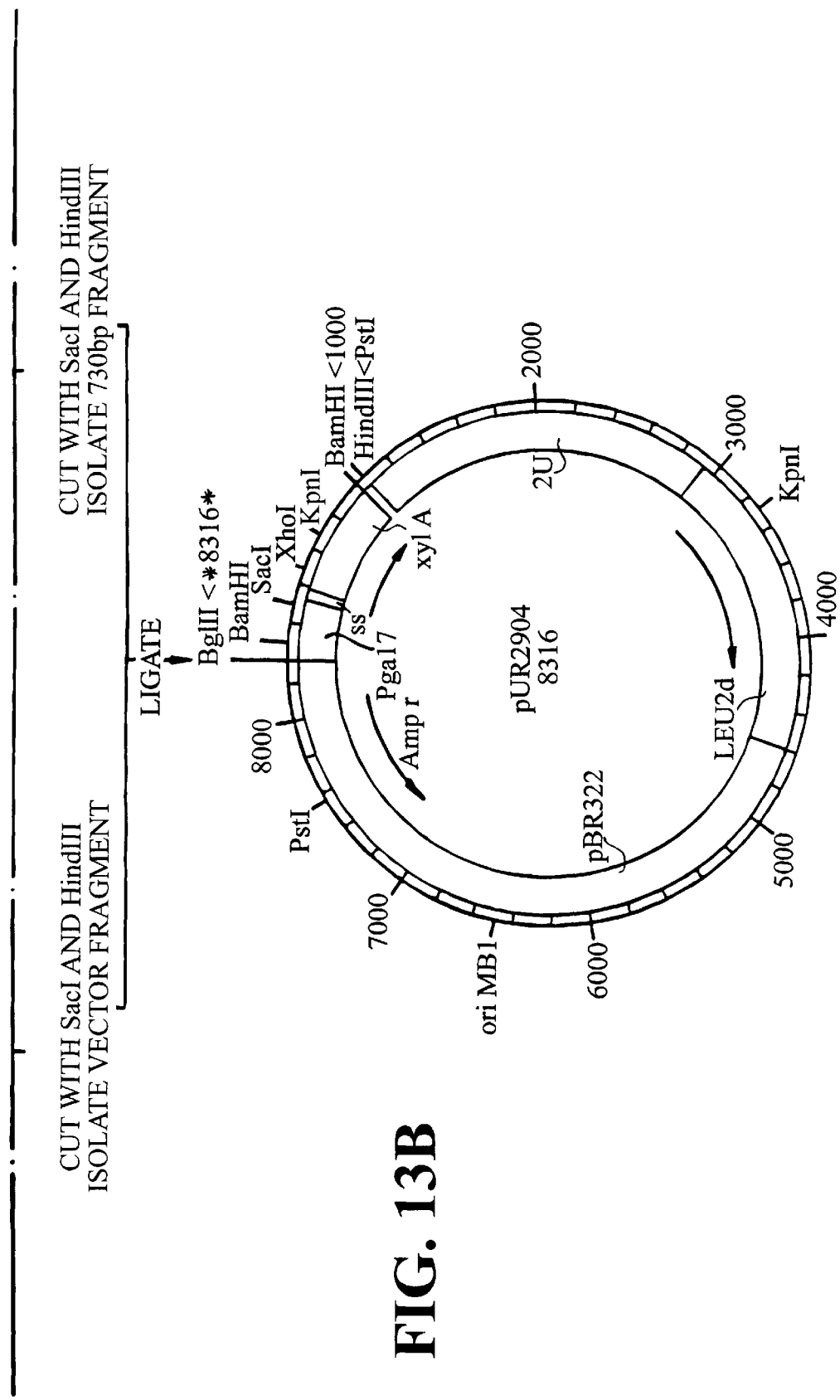

The construction of expression vector pUR2904 started from plasmid pUR2740. Plasmid pUR2740 is a derivative of pUR2730 (Overbeeke 1987) used for the production of α-gal-actosidase in S. cerevisiae. Plasmid pUR2740 is not essentially different from pUR2730, some superfluous sequences in the non-functional part of the vector have been removed. Plasmid pUR2740 is an E coli/S. cerevisiae shuttle vector. Use was made of the 2 μm origin of replication, and the S. cerevisiae LEU2d gene served as a selection gene for the replication in S. cerevisiae. Plasmid pUR2740 was digested with SacI and HindIII, and the vector fragment was isolated. As a result of this digestion, the α-galactosidase gene was removed. Plasmid pUR2901 was also digested with SacI and HindIII, and the 730 bp fragment comprising the S. cerevisiae GAL7 promoter fusion site at the ZacI site, the S. cerevisiae invertase signal sequence (including an ATG start codon), and the complete A. niger var. awamori xylanase gene (encoding mature xylanase) was isolated. The pUR2740 vector fragment and the 730 bp fragment of pUR2901 were ligated together, resulting in pUR2904 (see FIG. 13). Plasmid pUR2904 was checked by means of astriction enzyme analysis. Plasmid pUR2904 is the expression vector for the production of the Aspergillus niger var. awamori xylanase by the yeast Saccharomyces cerevisiae Plasmid pUR2904 is an E. coli/S. cerevisiae shuttle vector. It contains the DNA sequence encoding xylanase with the invertase signal sequence fused to it; the invertase signal sequence will provide the secretion of the xylanase. The DNA sequence in pUR2904 encodes exactly the same xylanase as the wild-type A. niger var. awamori strain. During secretion the resulting fusion protein will, in principle, undergo processing by the Saccharomyces cerevisiae signal peptidase resulting in secreted mature xylanase enzyme. The expression of the xylanase is regulated by the Saccharomyces cerevisiae galactose inducible GAL7 promoter.

Analysis of the Production of A. niger var. awamori Xylanase by S. cerevisiae

Yeast cells of the Saccharomyces strain SU10 (α, leu2, ura3, his3, cir+; deposited with the Centraalbureau voor Schimmelcultures, P.O. Box 273, 3740 AG Baarn, The Netherlands, under number CBS 323.87) were transformed with plasmid pUR2904 via the spheroplast method (Beggs, 1978). The resulting leu+ transformed yeast cells were analyzed for the presence of xylanase. The yeast cells were twice grown overnight on MM medium (0.67% Yeast Nitrogen Base w/o amino acids, 2% glucose) supplemented with uracil and histidine. Subsequently, the yeast cells were transferred to a ten times larger volume of YPG medium (1% Yeast Extract, 2% Bacto peptone, 5% galactose) and grown until the yeast cells had reached the stationary phase. The yeast cells were cultured under agitation at 30° C. The yeast cells were separated from the medium by centrifugation. The medium was analyzed for the presence of the xylanase with the enzyme assay as described in Example I. The expression level of xylanase was about 10000 units in 1 ml medium. By means of isoelectric focussing (see Example I) it was demonstrated that the xylanase produced by Saccharomyces cerevisiae is identical to the xylanase produced by wild-type Aspergillus niger var. awamori. The functionality of the xylanase, produced and secreted by Saccharomyces cerevisiae was shown in baking tests carried out as described in Example II. The results described above show that the yeast Saccharomyces cerevisiae is capable of efficiently producing and secreting Aspergillus niger var. awamori xylanase.

Construction of the S. cerevisiae Expression Vector PUR2921 (multi-copy Integration)

The expression of the xylanase gene of Aspergillus niger var. awamori in Saccharomyces cerevisiae was also studied by an integrative vector system. For this purpose the high-copy integration system was used (Lopes, 1989).

Figure 14A:
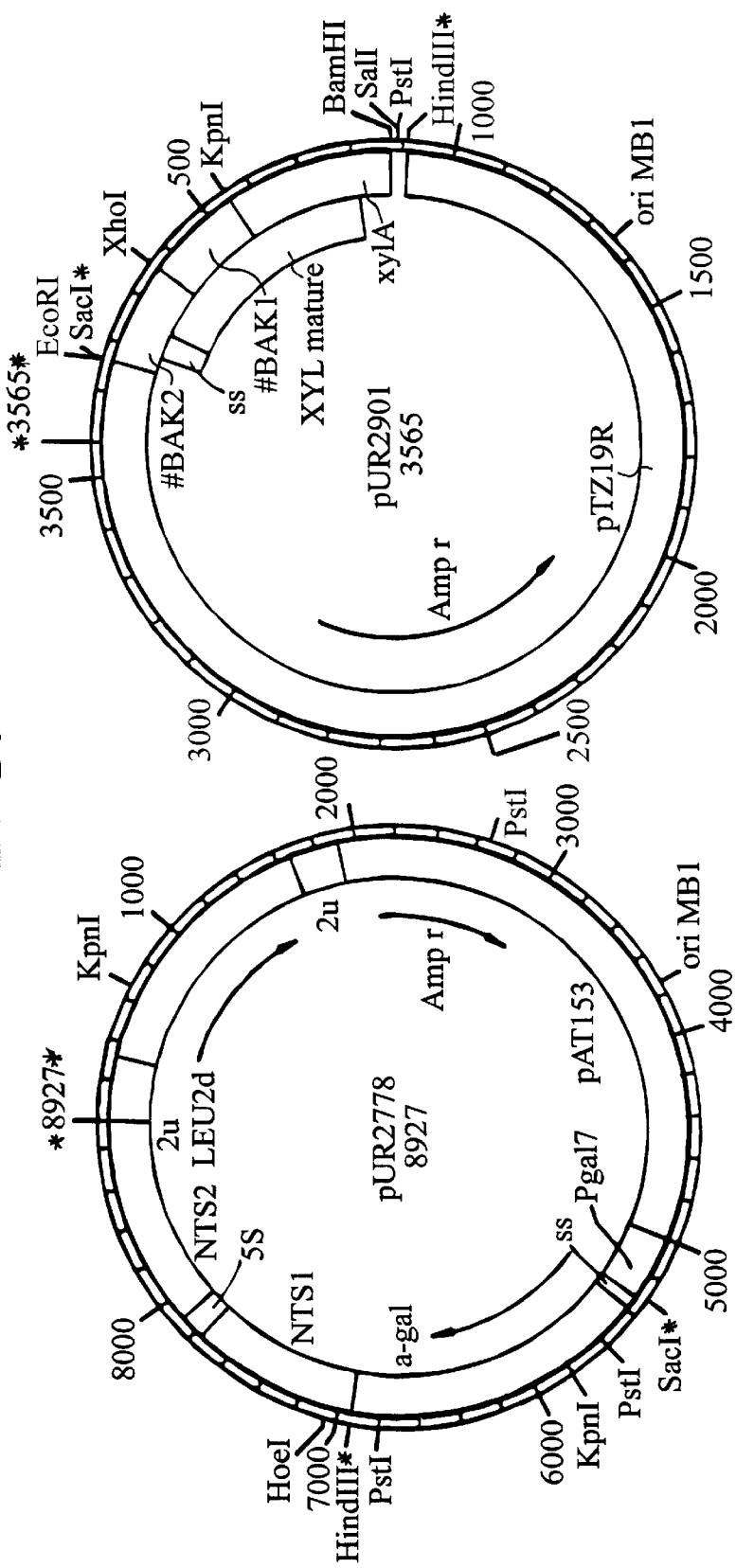
FIGS. 14A and 14B are a schematic representation of the construction of the plasmid pDUR2921.
Figure 14B:
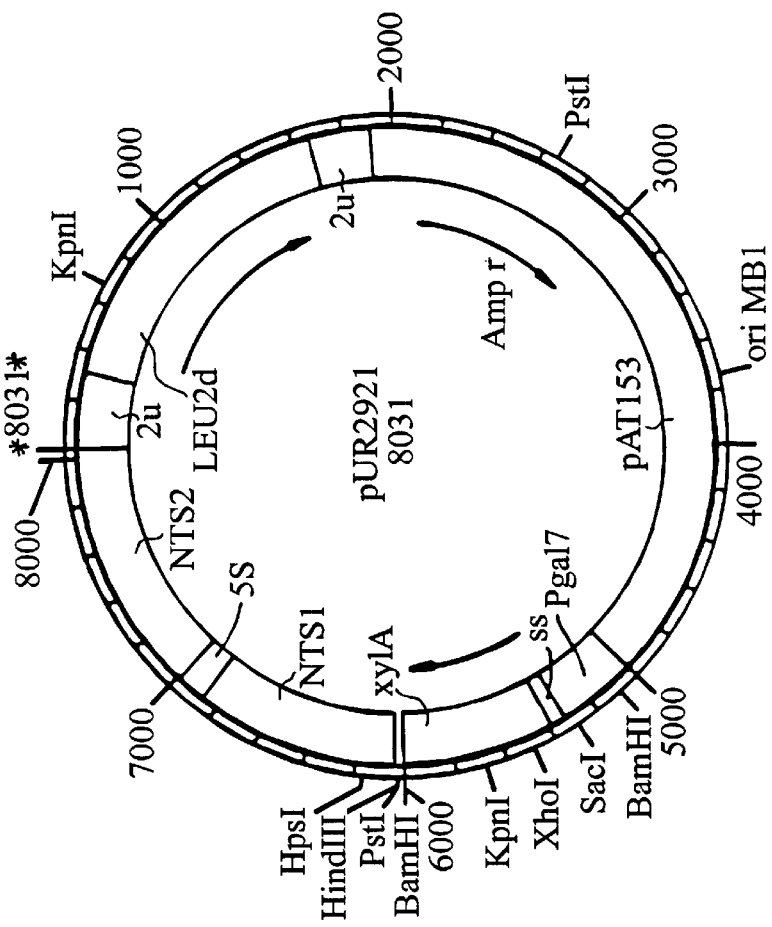

The construction of expression vector pUR2921 started from plasmid pUR2778. Plasmid pUR277 is a multi-integrative plasmid integrating in the ribosomal DNA locus of S. cerevisiae. It was used for stable multi-copy integration of the α-galactosidase expression cassette in S. cerevisiae. It also contains vector sequences for replication and selection in E. coli and the S. cerevisiae LLU2d gene as a selection gene for yeast. Plasmid pUR2778 is a derivative of pMIRY2 (Lopes, 1989), from which the SmaI-BglII fragment containing the Spirodella oligorhiza DNA has been removed, and the BamHI-HindIII fragment containing a part of the rDNA sequences has been replaced by the BglII-HindIII fragment of pUR2730 (Overbeeke, 1987) containing the α-galactosidase expression cassette. Plasmid pUR2778 was digested with SacI and HindIII, and the vector fragment was isolated from agarose gel. As a result of this digestion the α-galactosidase coding sequence including the invertase signal sequence was removed. This vector fragment was ligated with the 730 bp SacI-HindIII fragment from pUR2901, which was also used for the construction of pUR2904, resulting in plasmid pUR2921 (see FIG. 14). The 730 bp SacI-HindIII fragment of pUR2901 comprises the S. cerevisiae GAL7 promoter fusion site at the SacI site, the S. cerevisiae invertase signal sequence (including ATG start codon), and the complete A. niger var. awamori xylanase gene (encoding mature xylanase) from which the fungal intron (non-coding sequence) has correctly been removed. Plasmid pUR2921 was checked by means of restriction enzyme analysis. Plasmid pUR2921 is an expression vector for the production of the Aspergillus niger var. awamori xylanase by the yeast Saccharomyces cerevisiae. Plasmid pUR2921 contains sequences of the ribosomal DNA locus of the S. cerevisiae chromosomal DNA. As it does not contain any yeast replication origins the vector will integrate at the ribosomal DNA locus upon transformation to S. cerevisiae. When the pUR2921 plasmid is transformed to a S. cerevisiae leu2 strain, under selective conditions multiple copies of the vector will integrate, due to the low expression of the LEU2 marker gene of the pUR2921 plasmid. As a result of this process, the xylanase expression cassette will be present in multiple copies in the yeast chromosome. As the xylanase expression cassette is exactly the same as in the pUR2904 plasmid, this S. cerevisiae strain will secrete the mature xylanase enzyme in the same way as the S. cerevisiae strain with the pUR2904 plasmid.

Analysis of the Production of A. niger var. awamori Xylanase by S. cerevisiae

Yeast cells of the Saccharomyces strain SU50 (YT6-2-1, a, leu2, his4, can1, cir°; Erhart and Hollenberg, 1981) were transformed by the spheroplast method with plasmid pUR2921, linearized with HpaI. The resulting leu+ transformed yeast cells were analyzed for xylanase production as described for the SU10 yeast cells transformed with the pUR2904 plasmid. For these yeast cells the MM medium was only supplemented with histidine. The expression level was about 60,000 units secreted in 1 ml medium.

REFERENCES

Beggs, J. D. (1978), Nature 275: 104–109.
Erhart, Hollenberg (1981), Curr. Genet. 3:83–89.

Hopper, J. E. and Rowe, L. B. (1978), J. Biol. Chem. 253:7566–7569.

Lopes, T. S., Klootwijk, J., Veenstra, A. E., van der Aar, P. C., van Heerikhuizen, H., Raué, H. A. and Planta, R. J. (1989), Gene 79:199–206.

Maniatis, T., Fritsch, E. F. and Sambrook, J. (1982), Molecular Cloning. A laboratory manual, Cold Spring Harbor Laboratory.

Nogi, Y. and Fukasawa, T. (1983), Nucleic Acids Res. 11:8555–8568.

Overbeeke, N., Fellinger, A. J. and Hughes, S. G. (1987), PCT International. WO 87/07641.

Tajima, M., Nogi, Y. and Fukasawa, T. (1985), Yeast 1:67–77.

Yanisch-Perron, C., Viera, J. and Messing, J. (1985) Gene 33:103–119.

EXAMPLE IV

Production of *Aspergillus niger* var. *awamori* Xylanase by *Bacillus subtilis*

As an example of the heterologous production of *Aspergillus niger* var. *awamori* xylanase by a prokaryotic microorganism, expression vectors were constructed for the production of xylanase by *Bacillus subtilis*. Various vector systems, promoters and signal sequences are known for the production of heterologous proteins. For this example the SPO2 promoter and α-amylase signal sequence were used for the expression of the xylanase enzyme. This approach has been successful for the expression of the plant α-galactosidase in *B. subtilis* (Overbeeke et al, 1990).

For the construction of a vector for the expression of *Aspergillus niger* var. *awamori* xylanase by *Bacillus subtilis*, plasmids constructed for the expression of xylanase in *Saccharomyces cerevisiae* (see example III), in which the intron (non-coding sequence) of the xylanase gene was correctly removed, were used as a starting point. Removal of the intron is essential, because a prokaryotic microorganism such as *Bacillus subtilis* is not capable, unlike the eukaryote *Aspergillus niger* var. *awamori*, of removing introns by a process called splicing.

Construction of Vector pUR2950

Figure 16A:
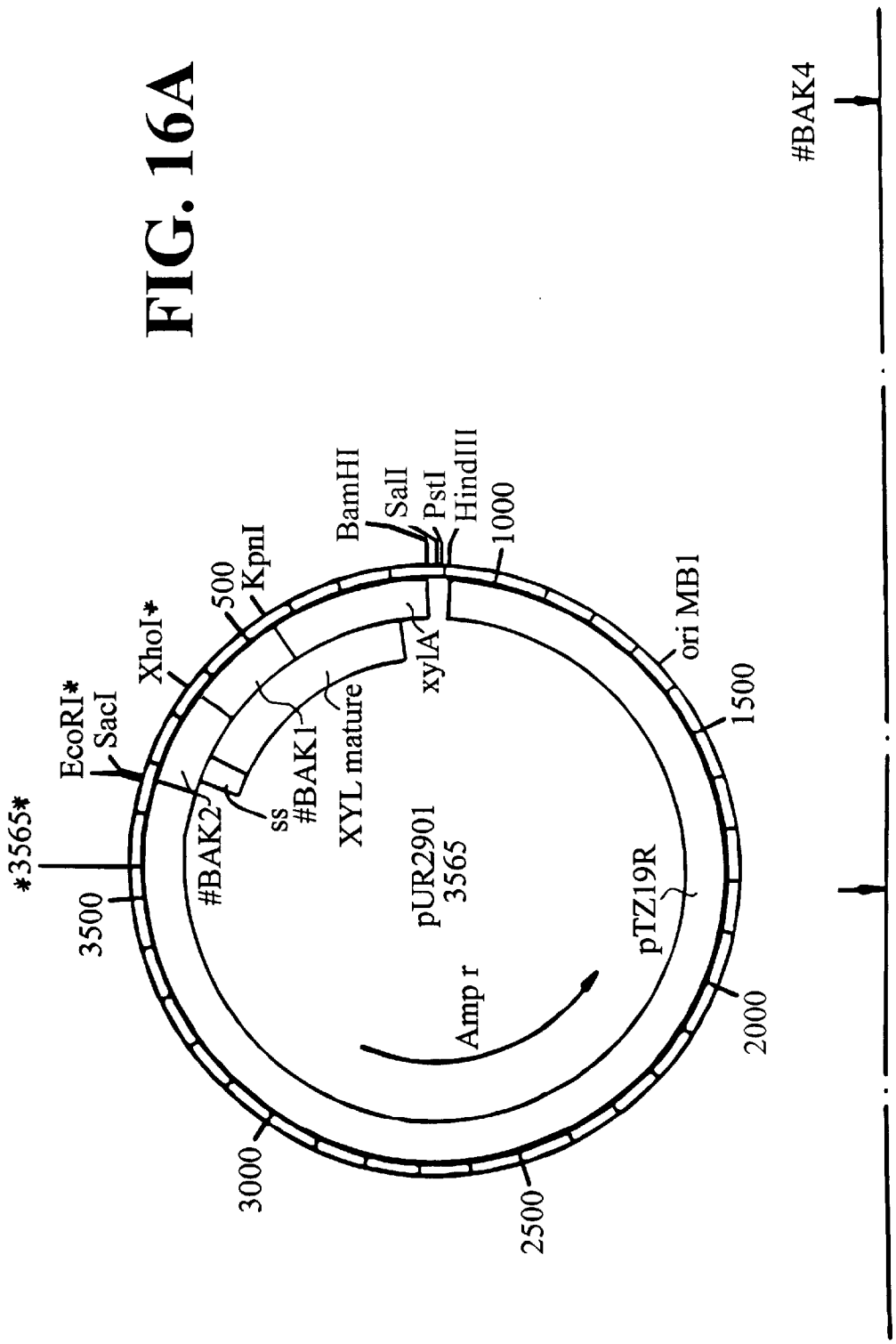
FIGS. 16A and 16B is a schematic representation of the construction of the plasmid pUR2950.
Figure 16B:
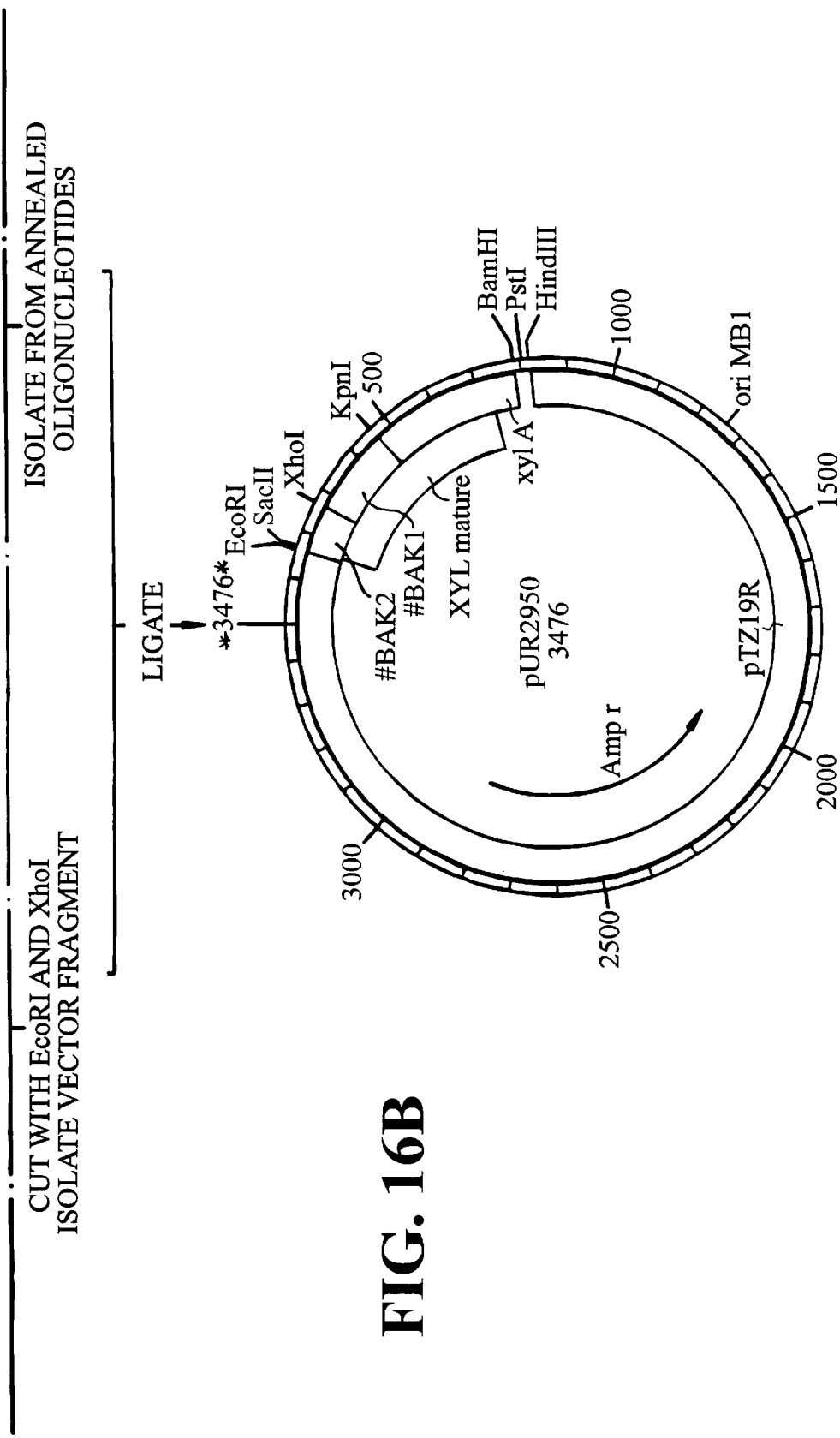

The synthetic DNA oligonucleotides shown in FIG. 15 (BAX 15, 18, 26, 27, 41 and 42(SEQ ID NO:s 19, 25,20, 26,28 and 27, respectively)) were annealed and ligated together resulting in fragment BAX4(SEQ ID NO:11). Fragment BAK4 (SEQ ID NO:11) measures 107 bp and comprises the DNA sequence encoding mature xylanase up to the SacI site (bp 185 in FIG. 1). In order to simplify the continued construction, the SacI site was changed to a XhoI site without changing the derived amino acid sequence. Moreover, in order to obtain a correct connection of the mature xylanase to the α-amylase signal sequence in the continued construction, the first codon of the mature xylanase encoding alanine was changed. The codon GCT was changed to GCC, also encoding alanine. Thus a SacII site was created on the 5' side of the BAK4 (SEQ ID NO:11) fragment. Continuous with this SacII site the BAK4 (SEQ ID NO:11) fragment was provided with an EcoRI site. The ligation mixture was digested with EcoRI and XhoI and the 107 bp EcoRI-XhoI fragment was isolated from agarose gel. Plasmid pUR2901 (see example III) was digested with EcoRI and XhoI and the BAK4 (SEQ ID NO:11) fragment was cloned in the vector fragment with the same restriction enzyme termini, resulting in pUR2950 (see FIG. 16). The inserted fragment BAK4 (SEQ ID NO:11) pUR2950 was checked by means of sequence analysis. In plasmid pUR2950 the connection of fragment BAK4 (SEQ ID NO:s 11 and 9, respectively) and BAK1 by means of the XhoI site was carried out in such a manner that the open reading frame encoding the 5' part of xylanase was correctly restored. Moreover, as described in Example III, the intron of the xylanase gene was correctly removed. Accordingly, plasmid pUR2950 contains the DNA sequence from the first alanine codon of mature xylanase, in which a SacII site has been made at that location, and the *Aspergillus niger* var. *awamori* xylanase gene encoding mature xylanase from which the fungal intron (non-coding sequence) has been correctly removed.

Construction of *B. subtilis* Expression Vector pUR2951

Figure 17A:
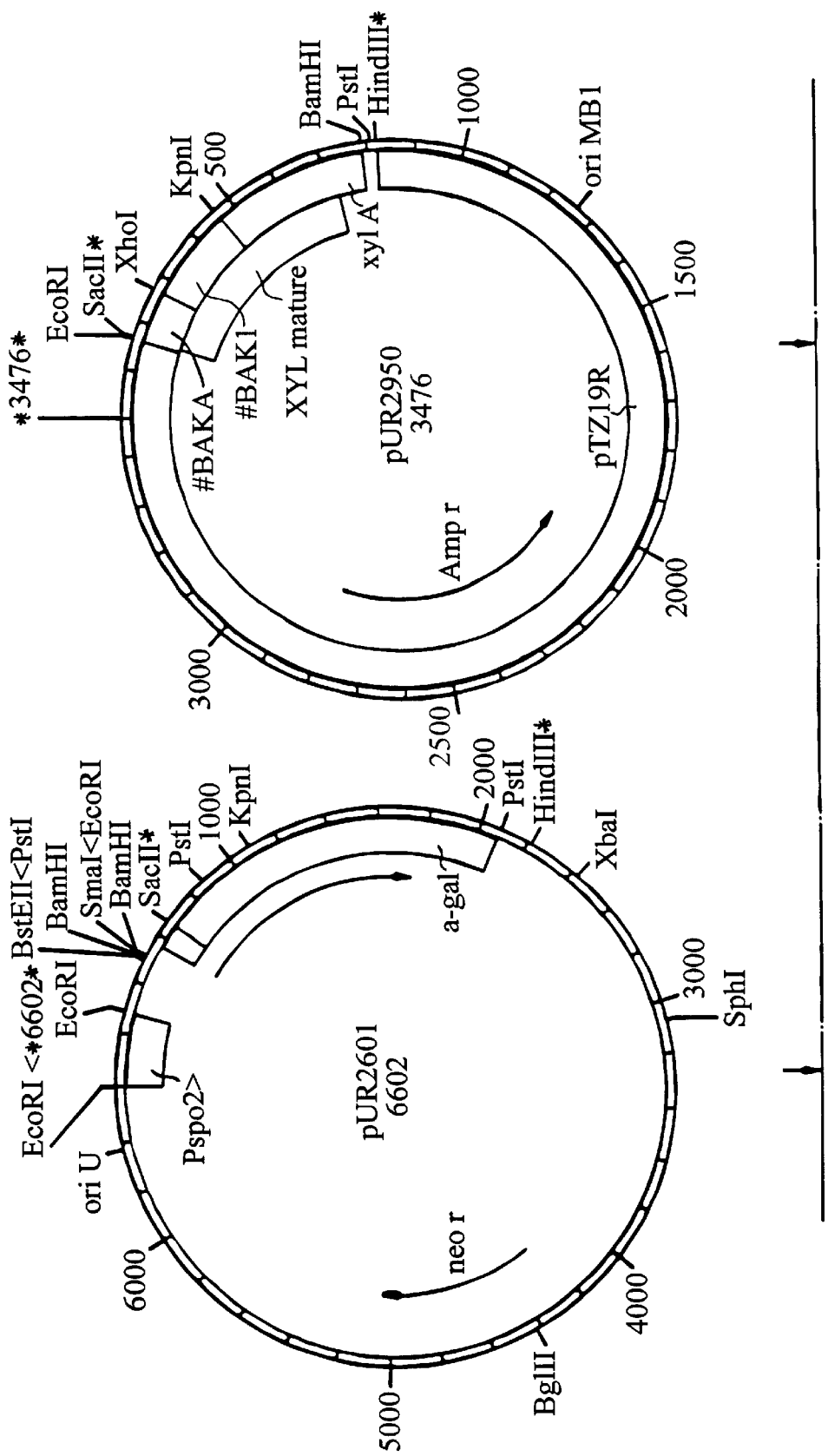
FIGS. 17A and 17B are a schematic representation of the construction of the plasmid pUR2951.
Figure 17B:
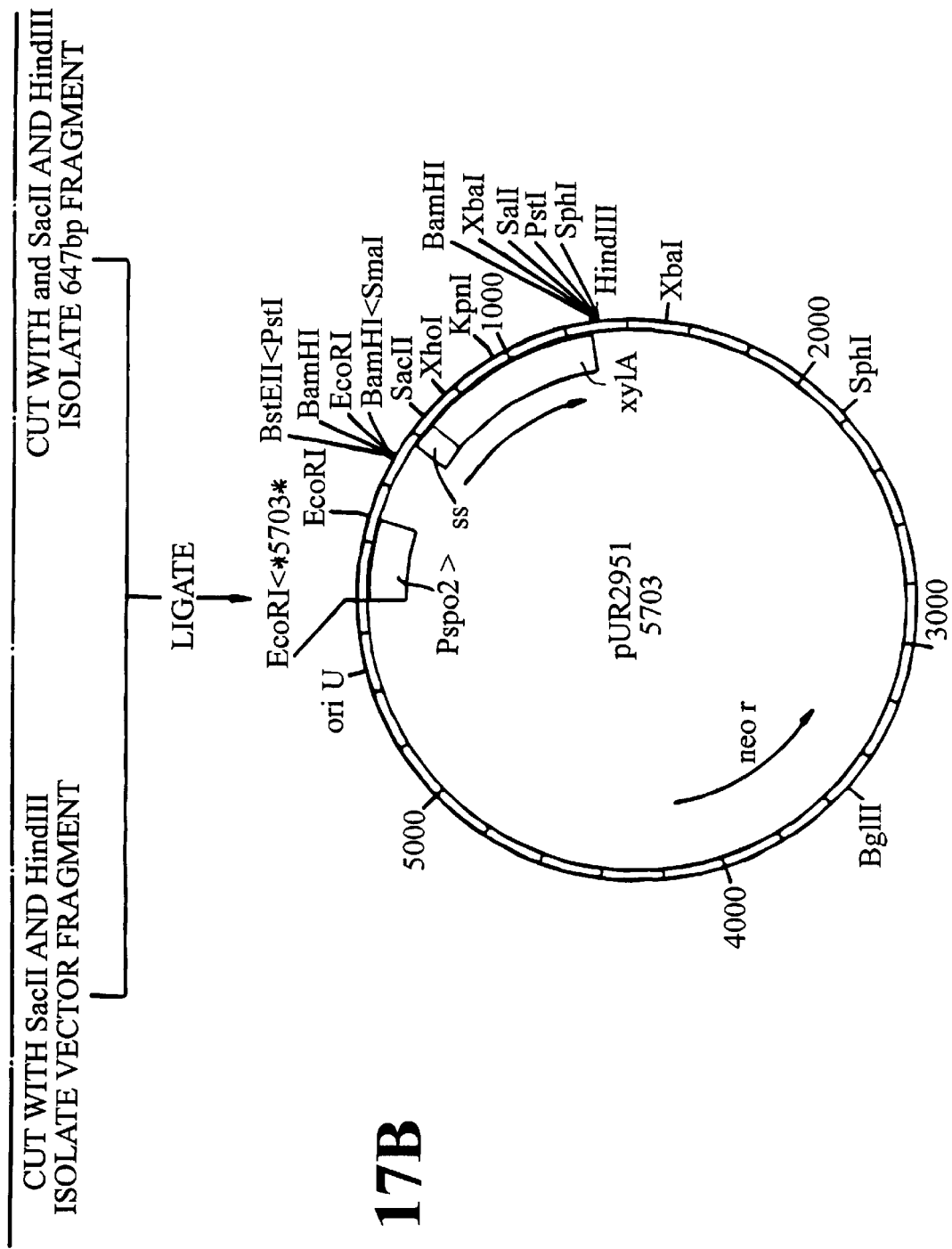

Plasmid pUR2601 (Overbeeke, 1990) was used as a base for the construction in which the mature *Aspergillus niger* var. *awamori* xylanase gene present in pUR2950 has been fused to the α-amylase signal sequence for secretion of the enzyme to be produced, while this fusion gene is regulated by the SPO2 promoter. Plasmid pUR2601 was digested with SacII and HindIII and the vector fragment with the SPO2 promoter and the α-amylase signal sequence was isolated. The SacII-HindIII fragment of pUR2950 with the mature xylanase gene was isolated and ligated to the pUR2601 vector fragment, resulting in plasmid pUR2951 (FIG. 17). In plasmid pUR2951 the α-amylase signal sequence has been fused in exactly the correct manner to the mature xylanase gene. The ligation mixture was transformed to the *Bacillus subtilis* strain DB104 (Kawamuri and Doi, 1984) using the protoplast/PEG method (Chang and Cohen, 1979) with kanamycin for selection. The plasmid pUR2951 was checked with restriction enzyme analysis.

Analysis of the Production of *A. niger* var. *awamori* Xylanase by *B. subtilis*

Because the DB104 strain has some residual protease activity, fermentation of DB104 with pUR2951 under controlled conditions is necessary to avoid proteolysis of the secreted enzyme. The approach described by Overbeeke et al. (1990) for the production of plant α-galactosidase by *B. subtilis*, can be used as starting point for the production of Aspergillus conditions is necessary to avoid proteolysis of the secreted enzyme. The approach described by Overbeeke et al. (1990) for the production of plant α-galactosidase by *B. subtilis*, can be used as starting point for the production of *Aspergillus niger* var. *awamori* xylanase by *Bacillus subtilis*. In this fermentation special attention is paid to the glucose and ammonium levels during fermentation.

REFERENCES

Chang, S., and Cohen, S. N. (1979), Mol. Gen. Genet. 182:77–81.

Kawamura, F., and Doi, R. H (1984), J. Bacteriol. 160:442–444.

Overbeeke, N., Termorshuizen, G. H. M., Giuseppin, M. L. F., Underwood, D. R., and Verrips, C. T. (1990), Appl. Environ. Microbiol. 56:1429–1434.

EXAMPLE V

Production of *Aspergillus niger* var. *awamori* Xylanase by *Saccharomyces cerevisiae* During Fermentation of Lean Bread Dough As an example of the direct use of cells which produce the *Aspergillus niger* var. *awamori* xylanase in foodstuffs, a *Saccharomyces cerevisiae* strain which produces the xylanase during fermentation of lean bread dough has been constructed. For this purpose the *S. cerevisiae* strain must secrete the xylanase under conditions present during the fermentation of wheat dough. In lean wheat dough no sugar is added and therefore the main carbon sources for the fermenting bakers yeast are glucose and maltose. The xylanase gene should therefore be regulated by a promoter which is not affected by glucose repression. Promoters of the genes of the glycolytic pathway (GAPDH, PGK, ADH1, PYK, etc.) of yeast are extremely useful for this purpose. Just by way of example the promoter of the phosphoglycerate kinase (PGK) gene of Saccharomyces cerevisiae was used. This promoter is used for the expression by S. cerevisiae of numerous heterologous proteins, for example the production of human interferon-alpha (Tuite et al., 1982).

The preferred way to achieve the expression of an enzyme during bread making is to use an integrative vector (single-copy or multi-copy integration), although autonomously replicating vectors can also be used.

The GAL7 promoter from the pUR2921 plasmid, used for the expression of the Aspergillus niger var. awamori xylanase in Saccharomyces cerevisiae (see example III), was replaced by the PGK promoter. S. cerevisiae strains transformed with this new vector, and which secretes the xylanase enzyme in culture media containing glucose, could be used in bread making. Addition of this yeast to dough before mixing results in secretion of the xylanase enzyme during bread making, and thus exhibits the positive effect of this bread improving enzyme, resulting in an increased specific volume of the bread.

Construction of Plasmid pUR2918

Figure 19:
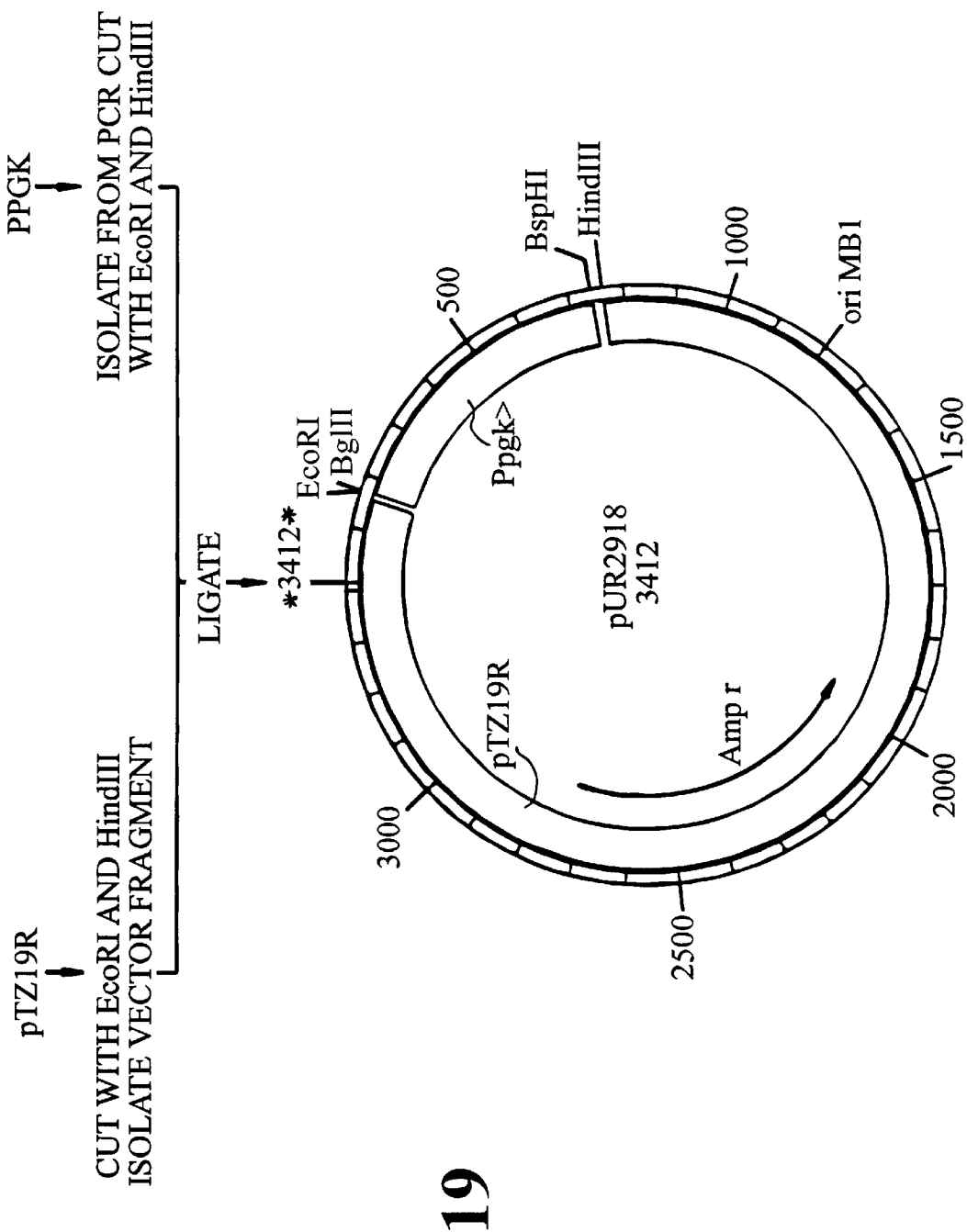
FIG. 19 is a schematic representation of the construction of the plasmid pUR2918.

For the fusion of the Saccharomyces cerevisiae PGK promoter sequences to the Aspergillus niger var. awamori xylanase gene several approaches were possible. Among others the creation of a suitable restriction endonuclease site at the end of the promoter by means of site directed mutagenesis that could yield a DNA molecule which, for example, could be fused to the SacI site between the GAL7 promoter and invertase signal sequence of pUR2904, the plasmid used for the expression of the mature xylanase by Saccharomyces cerevisiae. Another way of creating suitable restriction sites at the end of a DNA molecule is by way of an in vitro amplification technique of DNA known as Polymerase Chain Reaction. This PCR technique was used to generate a DNA molecule containing all important sequences of the Saccharomyces cerevisiae phosphoglycerate kinase promoter up to the ATG startcodon, with an EcoRI and a BglII site at its 5' end and a BspMI recognition sequence and a HindIII site (see FIG. 18 (SEQ ID NO: 12)) 3' to the ATG start3codon. The primers used for the amplification were PGP01 (SEQ ID NO: 13): 5'-GA ATT CAG ATC TTG AAT TGA TGT TAC CCT CAT AAA GCA CGT G-3' and PGP02 (SEQ ID NO: 14): 5'-CCC AAG CTT ACC TGC TGC GCA TTG TTT TAT ATT TGT TGT AAA AAG TAG ATA ATT ACT TCC-3'. Template DNA was pUR2802, a yeast expression vector with the complete Saccharomyces cerevisiae PGK promoter. The reaction mixture (total volume 100 μl) was composed as follows: Aprox. 1 ng pUF2801 cleaved with SalI, 100 pmoles of PGP01 (SEQ ID NO: 13) and 100 pmoles of PGP02, 1 U Amplitaq polymerase (Perkin Elmer), 0.2 mmol/l of each dNTP: dATP, dCTP, dGTP and dTTP, 1.5 mmol/l MgCl$_2$, 50 mmol/l KCl, 10 mmol/l Tris HCl pH 8.3 (at 25° C.), 0.001% (w/v) gelatine. After 2 minutes of incubation at 95° C., 25 cycles of the following temperature steps were carried out: 1 min at 95° C., 1:45 min at 52° C., 2 min at 72° C. After these cycles the reaction mixture was maintained at 72° C. for 5 min before cooling to 4° C. All temperature cycles were performed in a Perkin Elmer DNA Thermal Cycler. 60 μl was precipitated from the reaction mixture with ethanol and subsequently the band of approximately 600 bp was isolated from agarose gel. The isolated DNA was then cleaved with EcoRI and HindIII and isolated again from agarose gel. This DNA fragment starts with an EcoRI sticky end followed by a BglII site and the sequence from position—568 relative to the ATG codon up to the ATG codon of the Saccharomyces cerevisiae phosphoglycerate kinase promoter. The ATG codon is followed by a BspMI site and a HindIII sticky end. The multi-purpose cloning plasmid pTZ19R (obtained from Pharmacia) was cleaved with EcoRI and HindIII and ligated with the PGK promoter fragment, yielding pUR2918 (see FIG. 19). The plasmid was checked by means of sequence analysis.

Construction of plasmid PUR2920

Figure 21A:
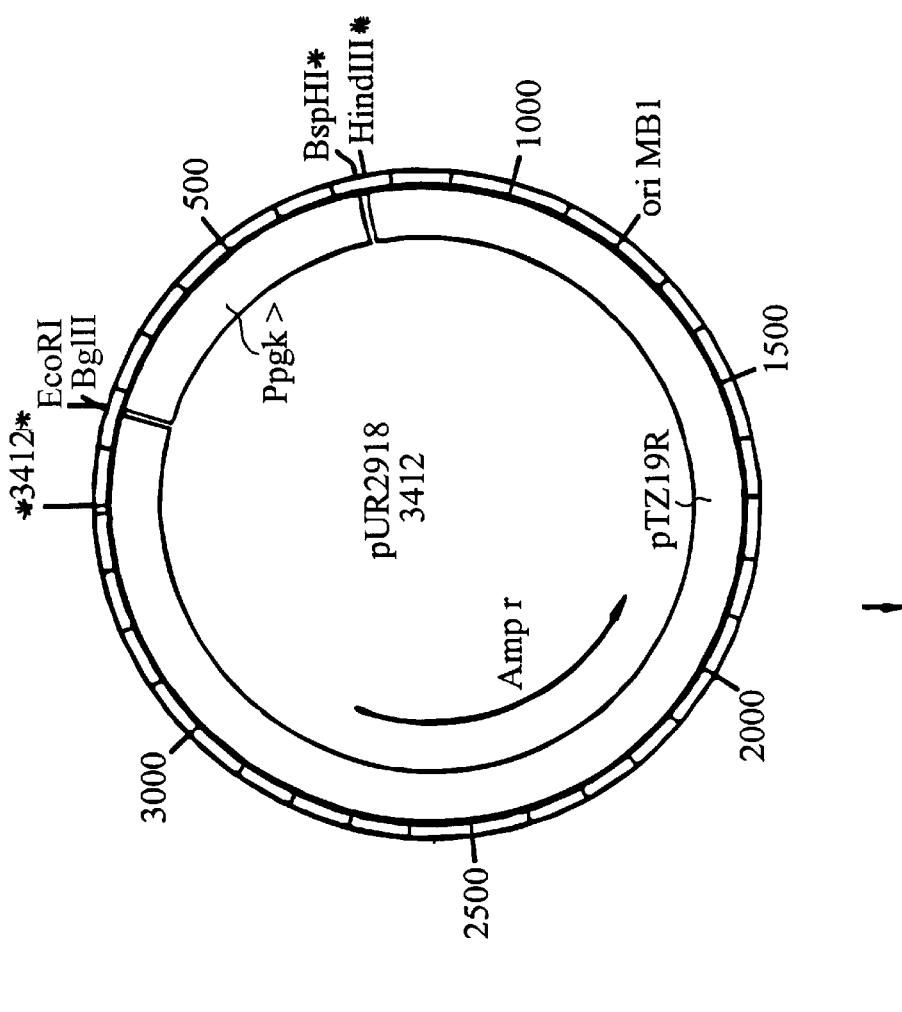
FIGS. 21A and 21B are a schematic representation of the construction of the plasmid pUR2920.
Figure 21B:
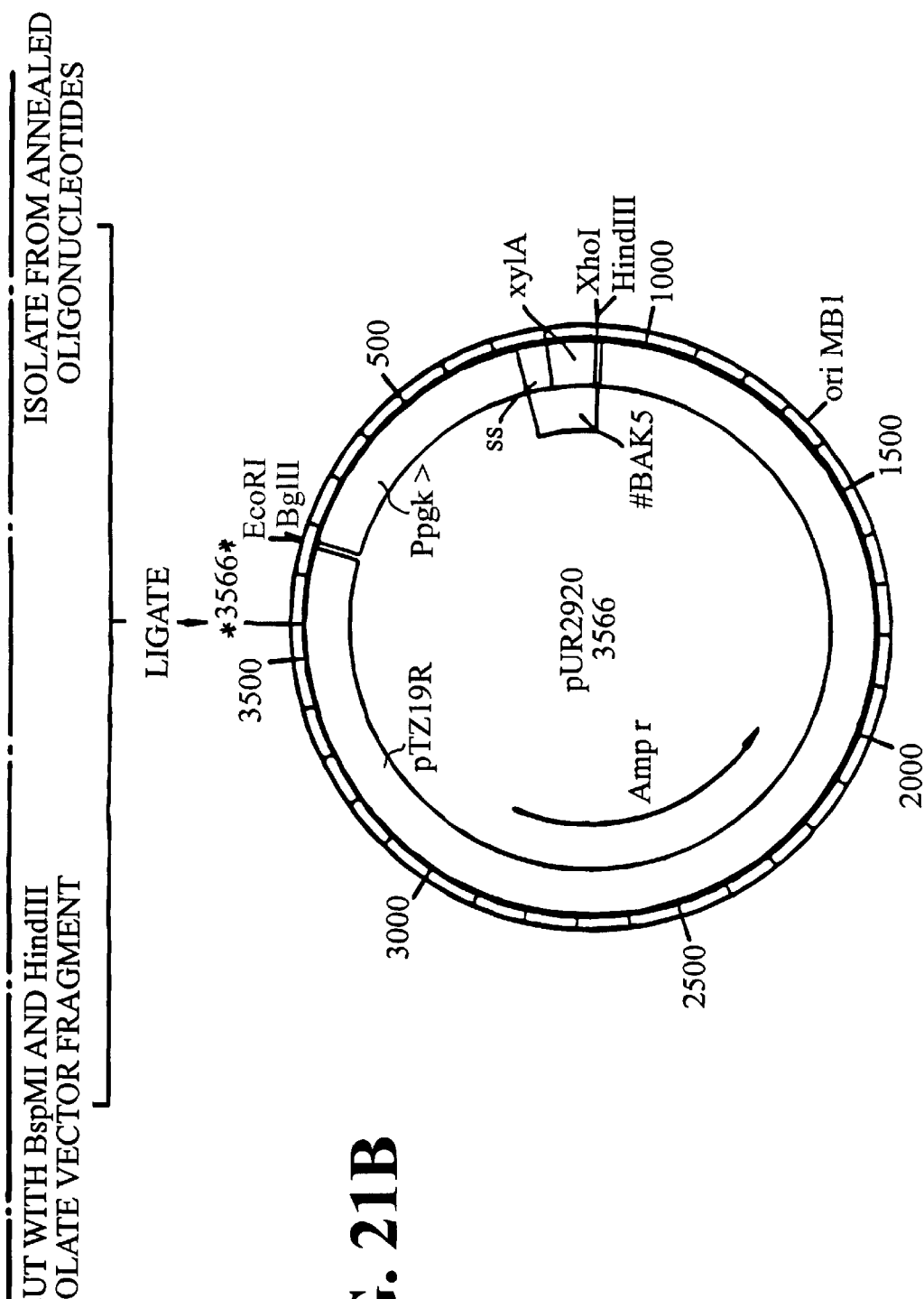

For the fusion of the PGM promoter of pUR2918 to the xylanase gene the synthetic DNA oligonucleotides shown in FIG. 20 (BAK14, 15, 18, 19, 20, 21, 51, 52 and 53(SEQ ID NO:s 18,19,25,24,23,22,30, 31 and 32, respectively)) were annealed and ligated together resulting in the fragment BAK5. The oligonucleotides BAK51 and BAK53 (SEQ ID NO:s 30 and 32, respectively) were not phosphorylated to prevent self-ligation of the resulting fragment, and the fragment was subsequently isolated from agarose gel. The fragment BAK5 measures 169 bp and comprises the invertase signal sequence and the mature xylanase gene up to the XhoI site for a correct fusion to fragment BAK1 (SEQ ID NO:9) (see example III). It differs from the earlier mentioned fragment BAK2 (SEQ ID NO:10) (example III) at both ends. At the 5' end it contains a sticky end just before the second codon of the invertase signal sequence to obtain an exact fusion to the PGK promoter sequence in pUR2918. At the 3' side of the XhoI site it contains an additional HindIII sticky end. The plasmid pUR2918 is cut with BspMI and HindIII and ligated to fragment BAK5 (SEQ ID NO:15) resulting in plasmid pUR2920 (see FIG. 21). The inserted fragment BAK5 was checked by means of sequence analysis. Plasmid pUR2920 contains the Saccharomyces cerevisiae phosphoglycerate kinase (PGK) promoter, from nucleotide –568 relative to the ATG start codon, up to the ATG start codon, the Saccharomyces cerevisiae invertase signal sequence correctly fused to this ATG codon, and the Aspergillus niger var. awamori xylanase gene up to the SacI site. In order to simplify the continued construction the SacI site was changed to a XhoI site as described in example III.

Construction of Plasmid pUR2922 and pUR2923

Figure 22A:
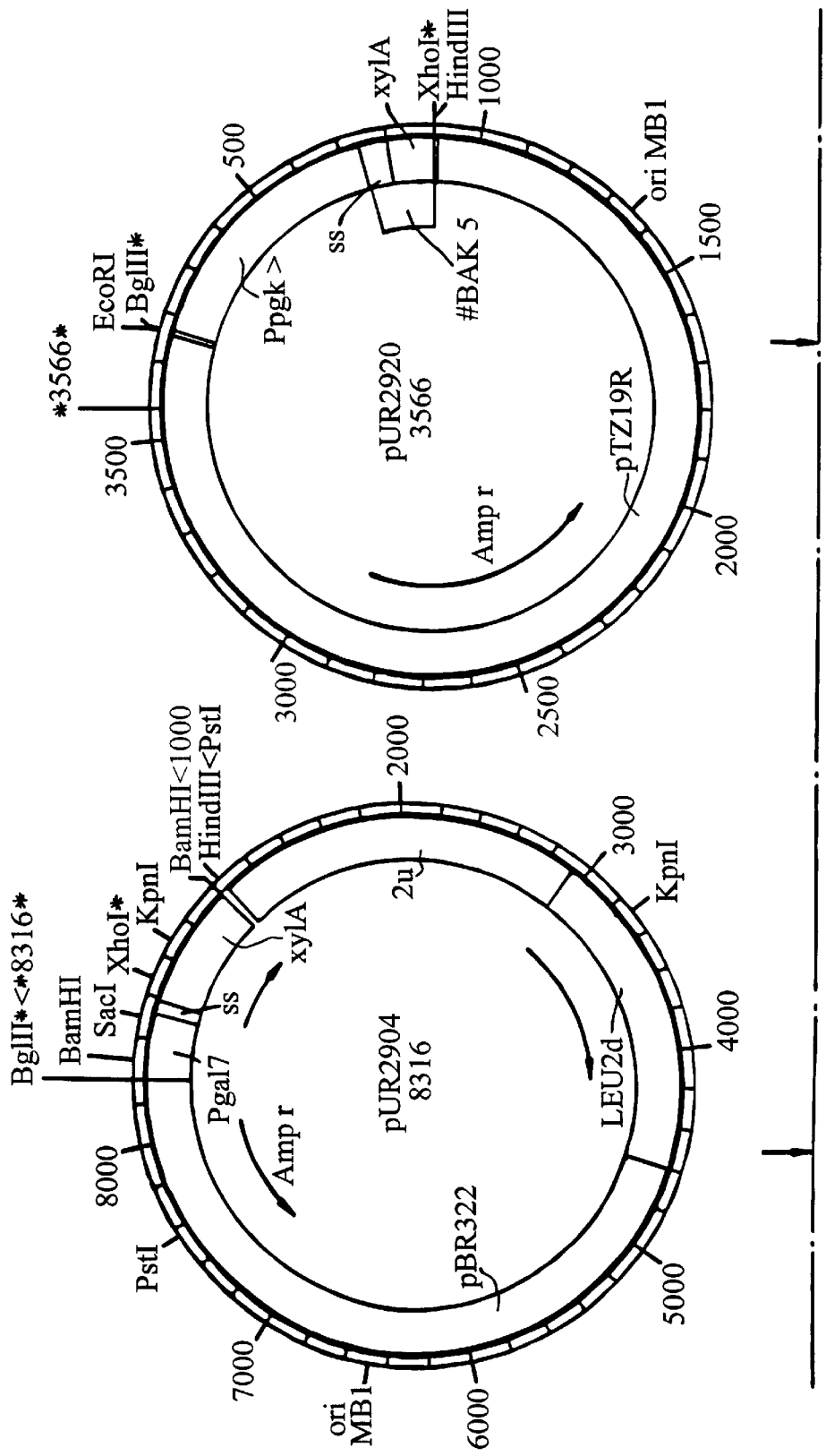
FIGS. 22A and 22B are a schematic representation of the construction of the plasmid pUR2922.
Figure 22B:
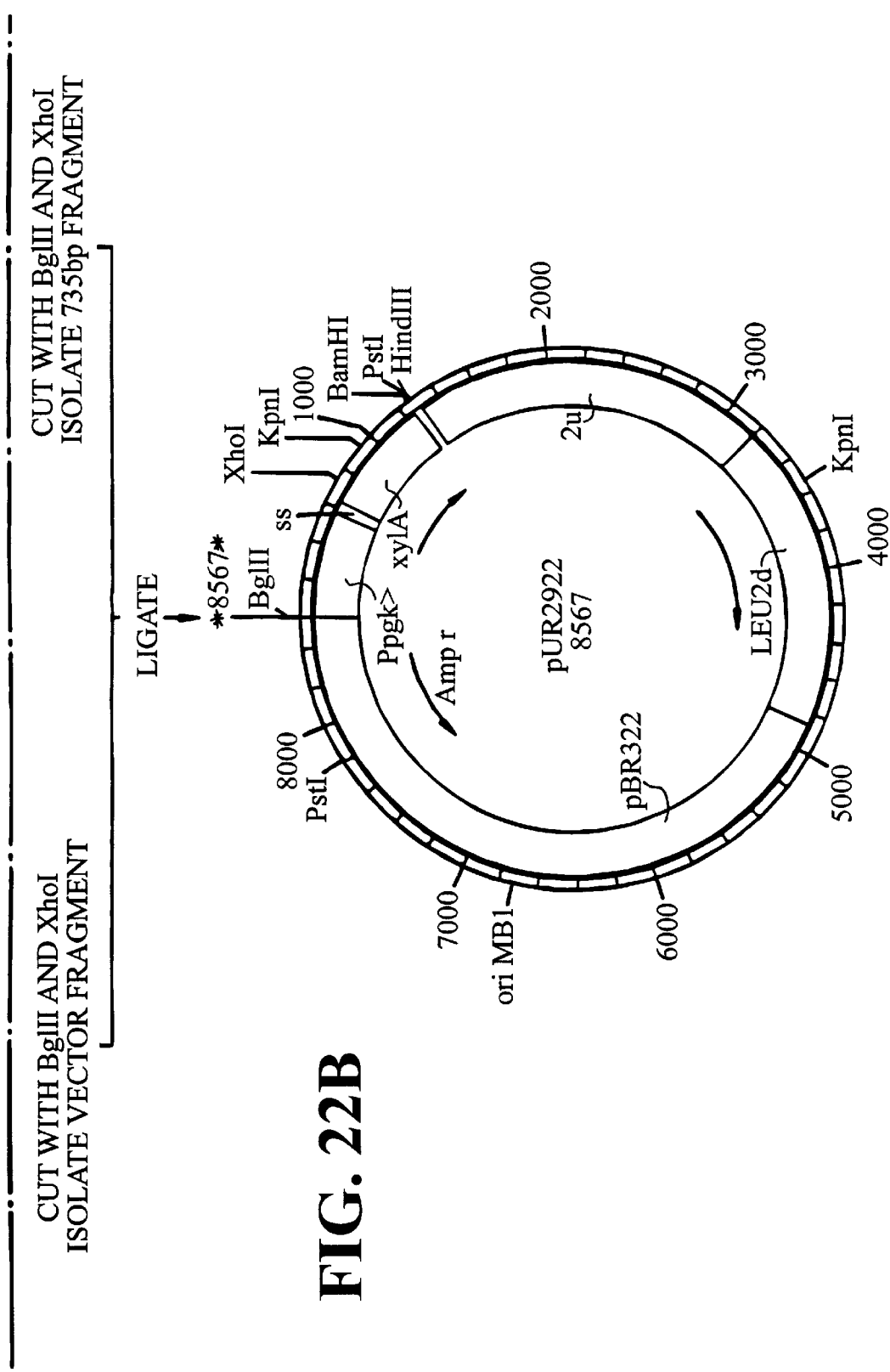

The 2 micron based episomal expression vector pUR2904 (see example III) was used to construct a plasmid vector for the expression of the xylanase gene regulated by the PGK promoter in S. cerevisiae. Plasmid pUR2920 was cleaved with BglII and XhoI and the 735 bp fragment containing the PGK promoter, the invertase signal sequence and the xylanase gene up to the XhoI site was isolated from agarose gel. Plasmid pUR2904 was also cleaved with BglII and XhoI and the large vector fragment was isolated. As a result of this digestion, the GAL7 promoter and invertase signal sequence were removed. This pUR2904 vector was ligated with the BglII-XhoI fragment of pUR2920, yielding pUR2922 (see FIG. 22). Plasmid pUR2922 differs from the Saccharomyces cerevisiae expression vector pUR2904 (example III) as it contains the Saccharomyces cerevisiae phosphoglycerate kinase promoter before the invertase signal sequence instead of the GAL7 promoter.

Figure 23A:
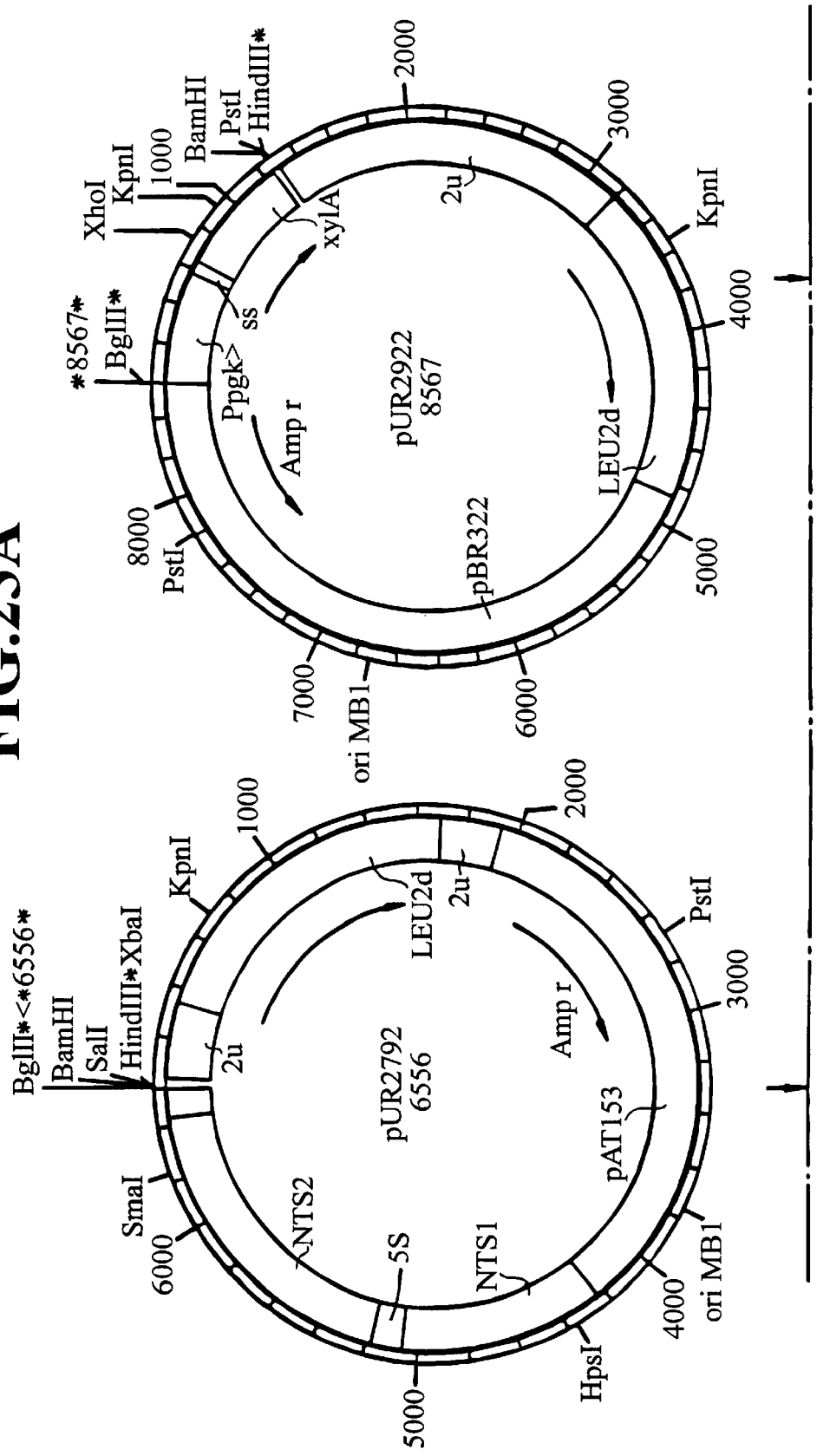
FIGS. 23A and 23B are a schematic representation of the construction of the plasmid pUR2923.
Figure 23B:
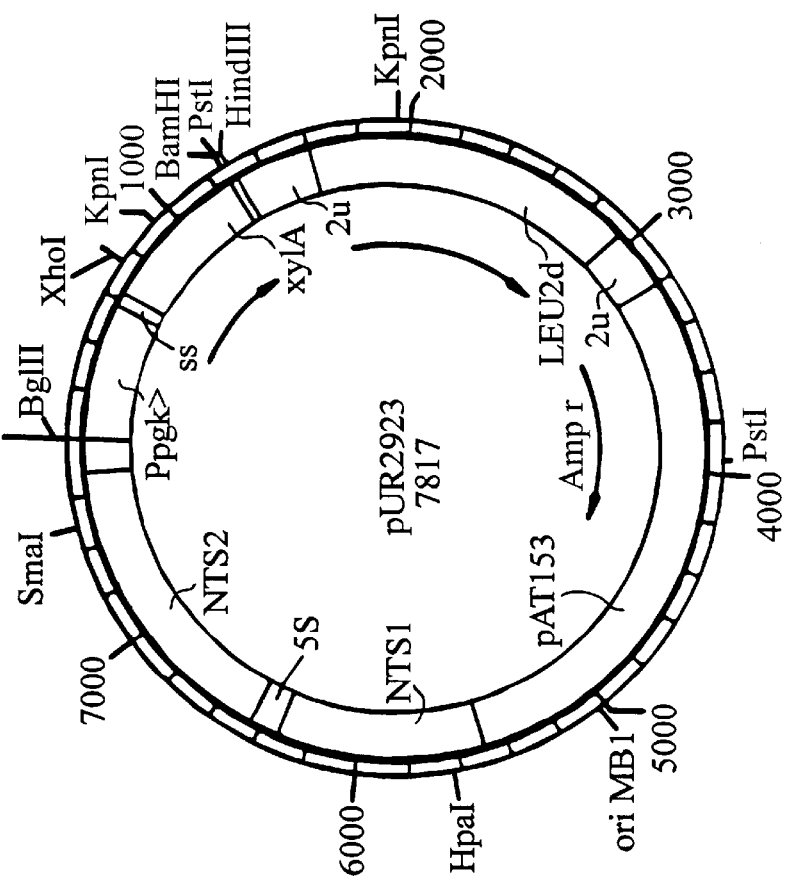

For the construction of a multi-copy integration vector with the PGK-xylanase expression cassette, plasmid pUR2792 served as starting point. Plasmid pUR2792 is a derivative of pMIRY2 (Lopes, 1989). It contains a BglII-HindIII polylinker instead of the BglII-HindIII part containing the S. oligorhiza DNA, and the part between the BalI site in the pAT153 sequence and the HindIII site in the rDNA sequence has been deleted. Plasmid pUR2792 was cleaved with BglII and HindIII and the vector band was isolated from agarose gel. The BglII-HindIII fragment containing the PGK controlled xylanase expression cassette was isolated from plasmid pUR2922 and ligated to pUR2792 vector that had been cleaved with BglII-HindIII. The resulting plasmid pUR2923 (see FIG. 23) is a Saccharomyces cerevisiae multi-copy integration plasmid which contains the Saccharomyces cerevisiae phosphoglycerate kinase promoter up to the ATG start codon, the *Saccharomyces cerevisiae* invertase signal sequence fused to this promoter and the *Aspergillus niger* var. *awamori* mature xylanase gene fused in frame to the invertase signal sequence. The intron (non-coding sequence) has been correctly removed from the xylanase gene.

Yeast cells of the *Saccharomyces cerevisiae* strain SU50 were transformed by the spheroplast method with plasmid pUR2923, linearized with HpaI (see example III). The resulting its+ transformed yeast cells were analyzed for xylanase production as described for the SU50 yeast cells with the pUR2921 plasmid, with one alteration, the use of YPD medium (1% Yeast Extract, 2% Bacto peptone, 2% glucose) instead of YPG at the final culturing stage. The expression level was about 10,000 units secreted in 1 ml medium.

Production of Xylanase by PUR2923 Containing Yeast in Dough

*Saccharomyces cerevisiae* SU50 cells containing the pUR2923 plasmid multi-copy integrated in the yeast chromosome were used in a baking test as described below. The increase in bread volume by the addition of xylanase is caused by an enzymatic alteration of the starch tailings, through which the dough is capable of taking more advantage of the gassing activity of the yeast in the dough. A yeast with a high gassing power is therefore required to obtain the full benefit of the addition of the xylanase enzyme. As the SU50 strain is a laboratory strain, it does not possess good gassing properties. For a baking experiment with the xylanase producing SUSO yeast strain, supplementation with a good gassing yeast strain is thus necessary.

The baking test described below was based on the 10 grams micro-loaf test (Shogren and Finney, 1984). The formulation of the dough was 10 g wheat flour (Columbus: MENEBA, The Netherlands); 0.15 g NaCl; 5.9 ml water; 0.2 g pressed yeast (Koningsgist; Gist-Brocades, The Netherlands). Supplementations to this formulation (xylanase producing and nonproducing yeast, xylanase enzyme) were dissolved in water just before mixing of the dough. Mixing took place for 5 minutes in a 10-gram mixograph from National Manufacturing Co. Lincoln, Nebr. After mixing, the dough was fermented for 80 min. at 30° C. with two punches, one punch at 40 min. and one at 80 min. Sheeting rolls used for the punching were spaced 2.0 mm. After fermentation the dough was moulded and proofed for 70 din at 30° C. before baking. Baking took place for 12 min at 240° C. After weighing, the volume of the loaves was measured by means of dwarf rapeseed displacement.

Supplementations to the dough were: *Saccharomyces cerevisiae* SU50 with pUR2923 (xylanase producing yeast), *Saccharomyces cerevisiae* SU50 (parent strain) and purified xylanase enzyme. The SU50 yeast strains used, were first grown on selective media: YNB w.o. amino acids (Difco) and 20 g/l glucose, supplemented with 60 mg/l leucine (SU50 parent only) and 20 mg/l histidine. These cultures were grown for 40 hours at 30° C. and then 5 ml was used to inoculate 45 ml of YPD (see above), and grown for 16 hours at 30° C. Yeast cells were collected by centrifugation, washed once with fresh YPD, and centrifugated again. Various amounts of the (wet) pellet were resuspended in 5.9 ml of water just before mixing the dough. When applied, the amount of purified xylanase added was 5 µl of a 40 U/µl solution (200 U). The effect of the various supplementations on the specific volume (S.V) of the bread is shown in the table below:

| Supplementation | S.V. | (ml/g) |
|---|---|---|
| none | | 3.31 |
| none | | 3.40 |
| 5 mg SU50 | 3.40 | |
| 15 mg SU50 | 3.39 | |
| 50 mg SU50 | 3.66 | |
| 5 mg SU50; 200 U xylanase | | 3.78 |
| 15 mg SU50; 200 U xylanase | | 3.97 |
| 50 mg SU50; 200 U xylanase | | 4.01 |
| 5 mg SU50:pUR2923 | | 3.88 |
| 15 mg SU50:pUR2923 | | 4.03 |
| 50 mg SU50:pUR2923 | | 4.31 |

From the results shown in this table it is clear that the yeast strain producing the xylanase (SU50:pUR2923) has a positive effect on the specific volume of the bread, comparable to that of the addition of purified xylanase enzyme. The parent strain, when added in equivalent amounts, does not exhibit this effect. Of course this effect is accomplished by blending of a bakers yeast with good gassing power characteristics, and an engineered laboratory yeast. The same positive effect, however, can be obtained when a bakers yeast with good gassing power is engineered in a comparable way to produce the fungal xylanase. Furthermore, these yeast strains can be engineered to produce other enzymes with bread improving capabilities ($\alpha$-amylases, hemicellulases etc.).

REFERENCES

Lopes, T. S., Klootwijk, J., Veenstra, A. E., van der Aar, P. C., van Heerikhuizen, H., Raué, H. A. and Planta, R. J. (1989), Gene 79:199–206.

Shogren, M. D. and Finney, K. F. (1984), Cereal Chem. 61:418–423.

Tuite, M. F., Dobson, M. J., Roberts, N. A., King, R. M., Burke, D. C., Kingsman, S. M. and Kingsman, A. J. (1982), EMBO Journal 1:603–608.

What is claimed is:

1. A purified recombinant DNA material comprising a nucleotide sequence encoding a ripening from of a β-1,4 endoxylanase of fungal origin having bread improving activity, said nucleotide sequence being selected from the group consisting of the nucleotide sequence of SEQ ID NO:7, a nucleotide sequence encoding the amino acid sequence encoded by SEQ ID NO:7, a nucleotide sequence which hybridizes to the nucleotide sequence of SEQ ID NO:7, said hybridization being performed in 6×SSC at 68° C. followed by wash steps in 2×SSc and 0.4×SSC, respectively at 68° C., a nucleotide sequence containing SEQ ID NO:7 which encodes a mature form of β-1,4 endoxylanase, a nucleotide sequence containing SEQ ID NO:7 which encodes a preform of β-1,4 endoxylanase, a nucleotide sequence containing SEQ ID NO:7 which encodes a proform of β-1,4 endoxylanase and a nucleotide sequence containing SEQ ID NO:7 which encodes a preproform of β-1,4 endoxylanse.

2. The recombinant DNA material according to claim 1, wherein said nucleotide sequence encoding a ripening form of a β-1,4 endoxylanase is of Aspergillus origin.

3. The recombinant DNA material according to claim 1, wherein said nucleotide sequence encoding a ripening form of a β-1,4 endoxylanase is of *Aspergillus niger* origin.

4. The recombinant DNA material according to claim 1, wherein said nucleotide sequence encoding a ripening form of a β-1,4 endoxylanase is a *Aspergillus niger* var. awamori origin.

5. The recombinant DNA material according to claim 1, wherein said nucleotide sequence encoding a ripening form of β-1,4 endoxylanase encodes SEQ ID NO:8.

6. The recombinant DNA material according to claim 1 comprising DNA with a nucleotide sequence encoding the mature form of β-1,4 endoxylanase.

7. The recombinant DNA material according to claim 1, further encoding at least one other enzyme having amylolytic or hemicellulolytic of cellololytic activity.

8. A transformed host cell comprising recombinant DNA material according to claim 1, such that said host cell expresses and secretes the ripening form of β-1,4 endoxylanase encoded by said recombinant DNA material.

9. The transformed host cell according to claim 8, wherein said host cell is selected from the group consisting of a bacterial cell, a fungal cell, a yeast cell and a plant cell.

10. The transformed host cell according to claim 9, wherein said host cell is a fungal cell selected from the genera Aspergillus and Trichoderma.

11. The transformed host cell according to claim 9, wherein said host cell is a fungal cell selected from the species *Aspergillus niger* var. *awamori, Aspergillus niger* var. *niger, Aspergillus nidulans* and *Aspergillus oryzae*.

12. The transformed host cell according to claim 9, wherein said host cell is a bacterial cell selected from the genera Bacillus, Lactobacillus and Streptococcus, or a yeast cell of the genera Saccharomyces, Kluyveromyces, Hansenula and Pichia.

13. The transformed host cell according to claim 9, wherein said host cell is selected from a yeast cell of species *Saccharomyces cerevisiae, Saccharomyces carlsbergensis, Kluyveromyces lactis, Kluyveromyces marxianus, Hansenula polymorpha* and *Pichia pastoris*.

14. A purified form of a β-1,4 endoxylanase encoded by the recombinant DNA material according to claim 1.

15. A process for producing a ripening form of a β-1,4 endoxylanase, said ripening form comprising SEQ ID NO:8, said process comprising:
  culturing a transformed host cell according to claim 8 in a nutrient medium such that said endoxylanase is produced, and
  optionally isolating said endoxylanase.

16. A bread improver composition comprising the β-1,4 endoxylanase according to claim 14.

17. A bread improver, flour or dough composition comprising a cell according to claim 8.

18. A bread improver, flour or dough composition comprising a cell according to claim 9.

19. A bread improver, flour or dough composition comprising a cell according to claim 10.

20. A flour or dough composition comprising a ripening form of β-1,4 endoxylanase according to claim 14.

21. A bakery product comprising the composition according to claim 20.

22. A process for preparing a bakery product by baking a flour composition wherein the improvement is adding the composition according to claim 20.

23. A method of processing a cellulose-containing raw material to prepare beer, paper, starch, or gluten, or to decompose cellulose- or hemicellulose-containing waste which comprises contacting said raw material with a ripening form of the β-1,4-endoxylanase according to claim 14.

24. The method of claim 23, wherein the ripening form of β-1,4 endoxylanase which is used is a mature form.

25. The method of claim 23, wherein the ripening form of β-1,4 endoxylanase which is used is of Aspergillus origin.

26. The method of claim 23 wherein the cellulose-containing raw material is agricultural waste which is contacted with said β-1,4 endoxylanase to produce animal feed.

27. The method of claim 23 wherein said cellulose-containing raw material is waste from paper mills.

28. A method of processing a cellulose-containing material to prepare beer, paper, starch or gluten or to decompose cellulose- or hemi-cellulose containing waste which comprises contacting said material with the transformed host cell according to claim 8 such that said cell secretes a ripening form of the β-1,4 endoxylanase in situ.

29. The method of claim 28 wherein the said ripening form of β-1,4 endoxylanase is a mature form.

30. The method of claim 28 wherein said ripening form of β-1,4 endoxylanase is of Aspergillus origin.

31. The method of claim 28 wherein said cellulose-containing material is agricultural waste which is contacted with the β-1,4 endoxylanase to produce animal feed.

32. The method of claim 28 wherein said cellulose-containing material is waste from paper mills.

33. A recombinant DNA material comprising a nucleotide sequence encoding a ripening form of a polypeptide having β-1,4 endoxylanase activity wherein said nucleotide sequence is selected from the group consisting of SEQ ID NO:7 and a nucleotide sequence encoding the polypeptide encoded by SEQ ID NO:7.

34. A purified form of β-1,4 endoxylanase encoded by the recombinant DNA material according to claim 33.

35. An isolated polypeptide comprising SEQ ID NO:8.

36. The recombinant DNA material according to claim 33, further encoding at least one other enzyme having amylolytic, hemicellulolytic or cellulolytic activity.

37. A transformed host cell comprising the recombinant DNA material of claim 33.

38. A bread improver, flour or dough composition comprising at least one of the purified forms of β-1,4 endoxylanase of claim 34 or a transformed host cell comprising a recombinant material comprising a nucleotide sequence encoding a ripening form of a polypeptide having β-1,4 endoxylanase activity wherein said nucleotide sequence is selected from the group consisting of SEQ ID NO:7 and a nucleotide sequence encoding the polypeptide encoded by SEQ ID NO:7.

39. A bakery product comprising the composition according to claim 38.

40. The method of processing a cellulose-containing raw material to prepare beer, paper, starch, or gluten, or to decompose cellulose- or hemicellulose-containing waste which comprises contacting said raw material with a ripening form of the β-1,4 endoxylanase according to claim 34.

41. A method of processing a cellulose-containing material to prepare beer, paper, starch or gluten or to decompose cellulose- or hemi-cellulose containing waste which comprises contacting said material with the transformed host cell according to claim 37 such that said cell secretes a ripening form of the β-1,4 endoxylanase in situ.

* * * * *